(12) United States Patent
White et al.

(10) Patent No.: US 10,835,265 B2
(45) Date of Patent: Nov. 17, 2020

(54) SURGICAL TEMPLATES

(71) Applicant: Xiros Limited, Leeds (GB)

(72) Inventors: Derrick White, Leeds (GB); Bahaa Seedhom, Harrogate (GB); Kenneth Langat Chelule, Nairobi (KE)

(73) Assignee: Xiros Limited, Leeds (GB)

( * ) Notice: Subject to any disclaimer, the term of this patent is extended or adjusted under 35 U.S.C. 154(b) by 0 days.

(21) Appl. No.: 15/985,564

(22) Filed: May 21, 2018

(65) Prior Publication Data

US 2019/0117237 A1    Apr. 25, 2019

Related U.S. Application Data

(63) Continuation of application No. 15/491,853, filed on Apr. 19, 2017, now Pat. No. 9,974,551, which is a
(Continued)

(51) Int. Cl.
*A61B 17/58* (2006.01)
*A61B 17/60* (2006.01)
(Continued)

(52) U.S. Cl.
CPC ........ *A61B 17/1764* (2013.01); *A61B 17/154* (2013.01); *A61B 17/155* (2013.01);
(Continued)

(58) Field of Classification Search
CPC combination set(s) only.
See application file for complete search history.

(56) References Cited

U.S. PATENT DOCUMENTS

| 4,718,413 A | 1/1988 | Johnson |
| 4,736,737 A | 4/1988 | Fargie et al. |
| (Continued) | | |

FOREIGN PATENT DOCUMENTS

| EP | 0558789 A1 | 9/1993 |
| EP | 0592750 B1 | 1/1999 |
| (Continued) | | |

OTHER PUBLICATIONS

Search Report from the United Kingdom Patent Office in corresponding U.K. Application No. GB0705613.8, dated Jul. 24, 2007, 3 pages.
(Continued)

*Primary Examiner* — Sameh R Boles
(74) *Attorney, Agent, or Firm* — Klarquist Sparkman, LLP

(57) ABSTRACT

A surgical template system for use in working on a bone comprises: a tool guide block comprising at least one guide aperture for receiving and guiding a tool to work on a bone; locating means comprising a plurality of locating members, each member having a respective end surface for positioning against a surface of the bone; and attachment means for non-adjustably attaching the tool guide block to the locating means such that, when attached, the member end surfaces are secured in fixed position with, respect to each other, for engaging different respective portions of the surface of the bone, and the at least one guide aperture is secured in a fixed position with respect to the end surfaces. Corresponding methods of manufacturing a surgical template system, methods of manufacturing locating means for a surgical template system, methods of fitting a prosthesis to a bone, surgical methods, and surgical apparatus are described.

37 Claims, 34 Drawing Sheets

Related U.S. Application Data continuation of application No. 15/012,550, filed on Feb. 1, 2016, now abandoned, which is a continuation of application No. 14/531,825, filed on Nov. 3, 2014, now Pat. No. 9,265,511, which is a continuation of application No. 13/937,079, filed on Jul. 8, 2013, now Pat. No. 9,125,675, which is a continuation of application No. 12/532,817, filed as application No. PCT/GB2008/000988 on Mar. 20, 2008, now Pat. No. 8,496,663.

(51) Int. Cl.

| | | |
|---|---|---|
| A61F 2/00 | (2006.01) | |
| A61B 17/17 | (2006.01) | |
| A61B 17/15 | (2006.01) | |
| A61B 90/94 | (2016.01) | |
| A61B 17/56 | (2006.01) | |
| A61F 2/28 | (2006.01) | |
| A61F 2/46 | (2006.01) | |
| B33Y 80/00 | (2015.01) | |
| A61B 17/00 | (2006.01) | |

(52) U.S. Cl.
CPC ............ *A61B 17/157* (2013.01); *A61B 17/17* (2013.01); *A61B 17/1703* (2013.01); *A61B 17/56* (2013.01); *A61B 90/94* (2016.02); *A61F 2/28* (2013.01); *A61F 2/461* (2013.01); *A61B 2017/00526* (2013.01); *A61B 2017/568* (2013.01); *B33Y 80/00* (2014.12); *Y10T 29/49826* (2015.01)

(56) References Cited

U.S. PATENT DOCUMENTS

| | | |
|---|---|---|
| 5,122,144 A | 6/1992 | Bert et al. |
| 5,569,260 A | 10/1996 | Petersen |
| 5,817,097 A | 10/1998 | Howard et al. |
| 5,935,128 A | 8/1999 | Carter et al. |
| 6,096,043 A | 8/2000 | Techiera et al. |
| 6,193,723 B1 | 2/2001 | Cripe et al. |
| 6,468,280 B1 | 10/2002 | Saenger et al. |
| 6,740,092 B2 | 5/2004 | Lombardo et al. |
| 7,153,327 B1 | 12/2006 | Metzger |
| 7,520,880 B2 | 4/2009 | Claypool et al. |
| 7,572,262 B1 | 8/2009 | Hoeppner et al. |
| 7,704,253 B2 | 4/2010 | Bastian et al. |
| 7,736,367 B2 | 6/2010 | Kuczynski |
| 7,758,652 B2 | 7/2010 | Engh et al. |
| 7,794,467 B2 | 9/2010 | McGinley et al. |
| 7,935,150 B2 | 5/2011 | Carignan et al. |
| 8,075,566 B2 | 12/2011 | Canonaco et al. |
| 8,122,582 B2 | 2/2012 | Burdulis et al. |
| 8,128,630 B2 | 3/2012 | Goodwin |
| 8,160,345 B2 | 4/2012 | Pavlovskaia et al. |
| 8,323,288 B2 | 12/2012 | Zajac |
| 8,343,159 B2 | 1/2013 | Bennett |
| 8,357,166 B2 | 1/2013 | Aram et al. |
| 8,361,076 B2 | 1/2013 | Roose et al. |
| 8,377,068 B2 | 2/2013 | Aker et al. |
| 8,398,645 B2 | 3/2013 | Aker et al. |
| 8,398,646 B2 | 3/2013 | Metzger et al. |
| 8,419,740 B2 | 4/2013 | Aram et al. |
| 8,425,523 B2 | 4/2013 | Aram et al. |
| 8,425,524 B2 | 4/2013 | Aker et al. |
| 8,551,103 B2 | 10/2013 | Fitz et al. |
| 8,585,708 B2 | 11/2013 | Fitz et al. |
| 8,594,395 B2 | 11/2013 | Roose et al. |
| 8,623,026 B2 | 1/2014 | Wong et al. |
| 8,628,560 B2 | 1/2014 | Moore et al. |
| 8,740,906 B2 | 6/2014 | Haines |
| 8,784,495 B2 | 7/2014 | Bonutti |
| 8,821,500 B2 | 9/2014 | Roger |
| 9,241,725 B2 | 1/2016 | Lang et al. |
| 9,326,780 B2 | 5/2016 | Wong et al. |
| 9,492,186 B2 | 11/2016 | Ghijselings |
| 9,795,399 B2 | 10/2017 | Metzger et al. |
| 2003/0225413 A1 | 12/2003 | Sanford et al. |
| 2004/0236424 A1 | 11/2004 | Berez et al. |
| 2005/0228393 A1 | 10/2005 | Williams et al. |
| 2007/0226986 A1 | 10/2007 | Park et al. |
| 2007/0288030 A1 | 12/2007 | Metzger et al. |
| 2009/0087276 A1 | 4/2009 | Rose |
| 2009/0088753 A1 | 4/2009 | Aram et al. |
| 2009/0088754 A1 | 4/2009 | Aker et al. |
| 2009/0088760 A1 | 4/2009 | Aram et al. |
| 2009/0088763 A1 | 4/2009 | Aram et al. |
| 2009/0093816 A1 | 4/2009 | Roose et al. |
| 2009/0131942 A1 | 5/2009 | Aker et al. |
| 2010/0087829 A1 | 4/2010 | Metzger et al. |
| 2012/0041446 A1 | 2/2012 | Wong et al. |
| 2012/0072185 A1 | 3/2012 | Lang et al. |
| 2014/0236305 A1 | 8/2014 | Olgiati et al. |

FOREIGN PATENT DOCUMENTS

| | | |
|---|---|---|
| EP | 1669033 A | 6/2006 |
| EP | 2959848 B1 | 4/2019 |
| FR | 2819168 A | 7/2002 |
| WO | WO1993/025157 | 12/1993 |
| WO | WO1995/13034 A1 | 5/1995 |
| WO | WO2004/017842 | 3/2004 |
| WO | WO2006/060795 A | 6/2006 |
| WO | WO2007/013959 A2 | 2/2007 |
| WO | WO2009/001083 A1 | 12/2008 |
| WO | WO2009/045960 | 4/2009 |

OTHER PUBLICATIONS

International Search Report of the International Searching Authority, for corresponding International Application No. PCT/GB2008/000988, dated Jun. 13, 2008, 4 pages.

Written Opinion of the International Searching Authority, for corresponding International Application No. PCT/GB2008/000988, dated Jun. 13, 2008, 7 pages.

International Preliminary Report on Patentability of the International Searching Authority, for corresponding International Application No. PCT/GB2008/000988, dated Oct. 8, 2009, 9 pages.

Radermacher, et al., "Computer-Integrated Orthopaedic Surgery: Connection of Planning and Execution in Surgical Intervention," *Computer-Integrated Surgery, Technology and Clinical Applications*, Massachusetts Institute of Technology, Chapter 33, pp. 451-463, 1996.

Radermacher, et al., Technique for Better Execution of CT Scan Planned Orthopaedic Surgery on Bone Structures, pp. 933-938, Jun. 1995.

Radermacher, et al., "Computer Assisted Orthopaedic Surgery with Image Based Individual Templates," *Clinical Orthopaedics and Related Research*, No. 354, pp. 28-38, Sep. 1998.

Office Action from the United States Patent & Trademark Office in co-pending U.S. Appl. No. 12/532,817, dated Nov. 13, 2012.

Notice of Allowance from the United States Patent & Trademark Office in co-pending U.S. Appl. No. 12/532,817, dated Apr. 25, 2013.

Office Action from the United States Patent & Trademark Office in co-pending U.S. Appl. No. 13/937,007, dated Feb. 20, 2015.

Office Action from the United States Patent & Trademark Office in co-pending U.S. Appl. No. 13/937,079, dated Feb. 20, 2015.

Notice of Allowance from the United States Patent & Trademark Office in co-pending U.S. Appl. No. 13/937,079, dated Apr. 30, 2015.

Notice of Allowance from the United States Patent & Trademark Office in co-pending U.S. Appl. No. 13/937,007, dated May 1, 2015.

Office Action from the United States Patent & Trademark Office in co-pending U.S. Appl. No. 14/531,825, dated Jul. 6, 2015.

Notice of Allowance from the United States Patent & Trademark Office in co-pending U.S. Appl. No. 14/531,825, dated Oct. 13, 2015.

(56) References Cited

OTHER PUBLICATIONS

Office Action from the United States Patent & Trademark Office in co-pending U.S. Appl. No. 15/012,550, dated Aug. 1, 2016.
Office Action from the United States Patent & Trademark Office in co-pending U.S. Appl. No. 15/012,550, dated Oct. 19, 2016.
Notice of Allowance from the United States Patent & Trademark Office in co-pending U.S. Appl. No. 15/491,853, dated Jan. 19, 2018.
Mahmoud Alm El-din Abdel Hafez, "Computer Assisted Total Knee Arthroplasty Using Patient Specific Templates," Medical School, The University of Leeds, pp. 1-159, Jun. 2006.
Hafez et al., "Computer-assisted Total Knee Arthroplasty Using Patient-specific Templating," *Clinical Orthopaedics and Related Research*, No. 444, pp. 184-192, 2006.
Hafez et al., "Computer-Assisted Total Knee Arthroplasty Using Patient-Specific Templates: the Custom-made Cutting Guides," Chapter 24 of Part II A—Navigation: Total Knee Arthroplasty, *Navigation and MIS in Orthopedic Surgery*, pp. 182-188, 2007.
Wolfram H. Kluge, "(iv) Computer-assisted knee replacement techniques," Mini-symposium: Computer-assisted Surgery in Orthopaedics, *Current Orthopaedics*, vol. 21, pp. 200-206, 2006.
Owen et al., "Rapid prototype patient-specific drill template for cervical pedicale screw placement," *Computer Aided Surgery*, vol. 12, No. 5, pp. 303-308, 2007.
Wolf et al., MBARS: mini bone-attached robotic system for joint arthroplasty, *Int J. Medical Robotics and Computer Assisted Surgery*, vol. 1(2), pp. 101-121, 2005.
Wolf et al., "Computer-Guided total Knee Arthroscopy," Section V Computer Navigation, Chapter 24, MIS Techniques in Orthopedics, pp. 390-391, 2006.

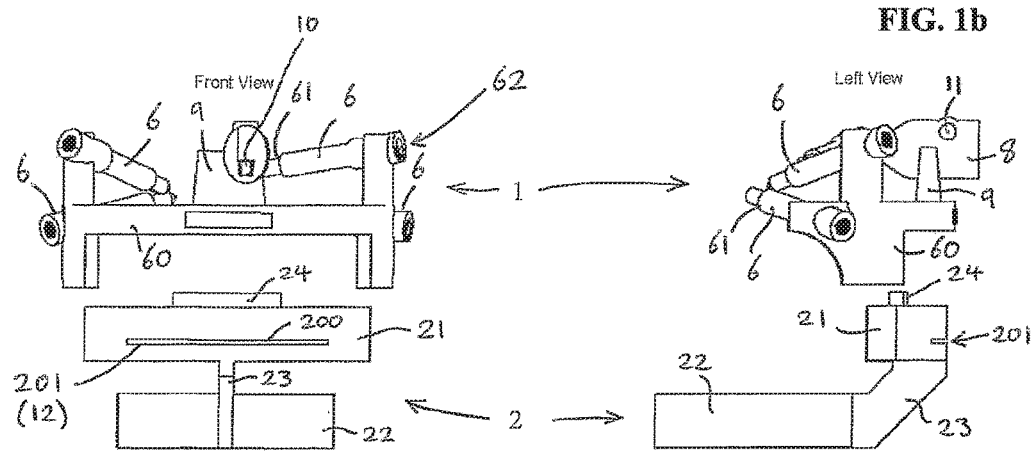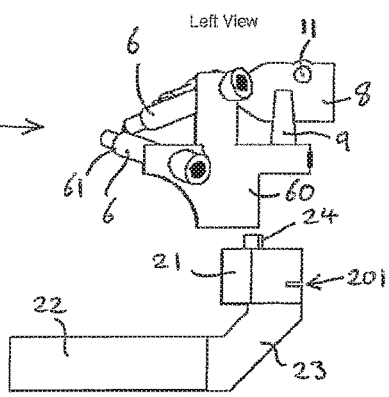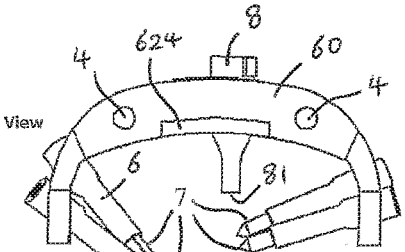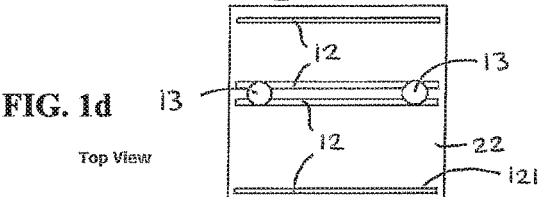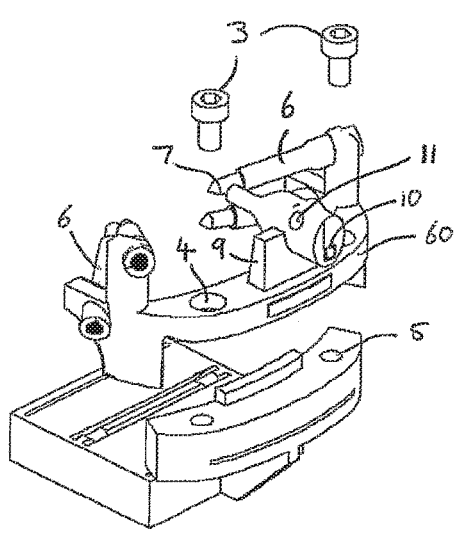

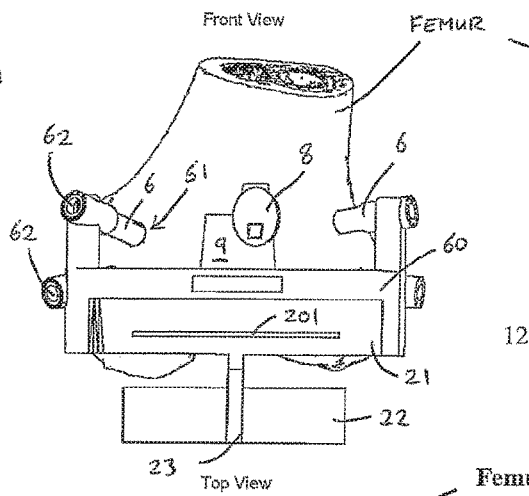
FIG. 2a
FIG. 2b
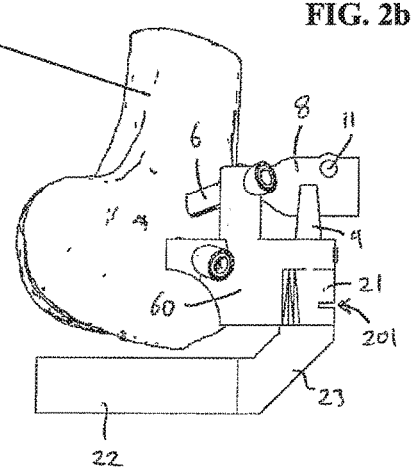
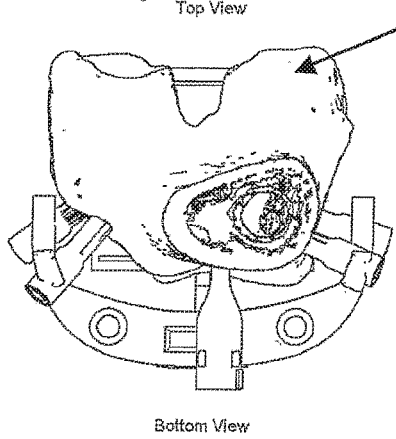
FIG. 2c
FIG. 2e
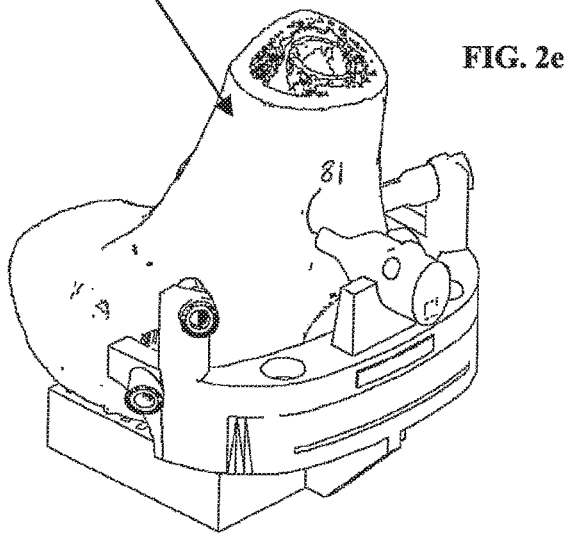
FIG. 2d
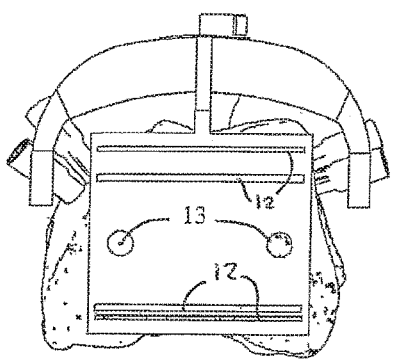

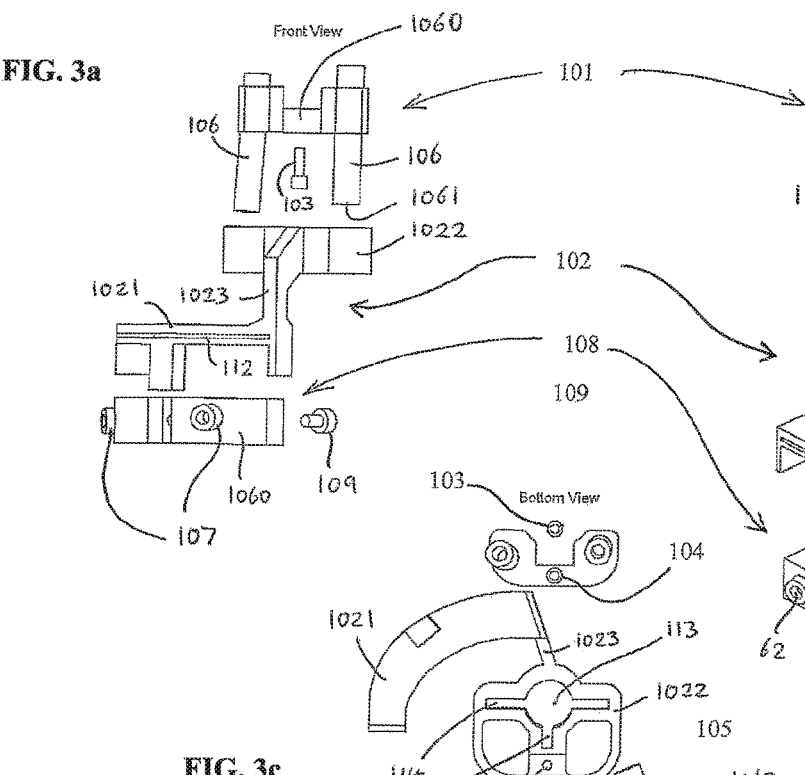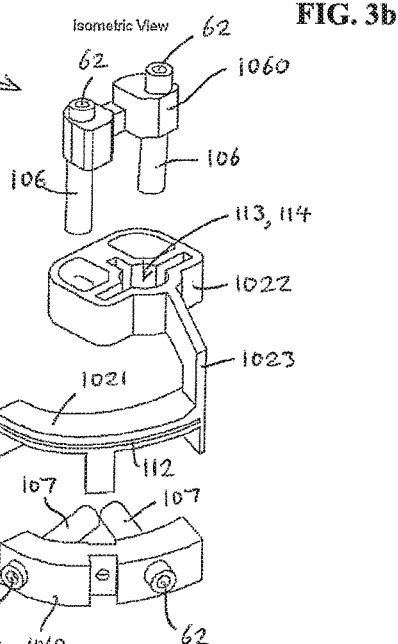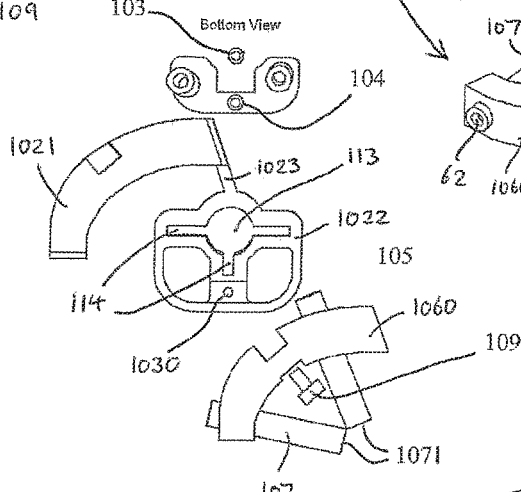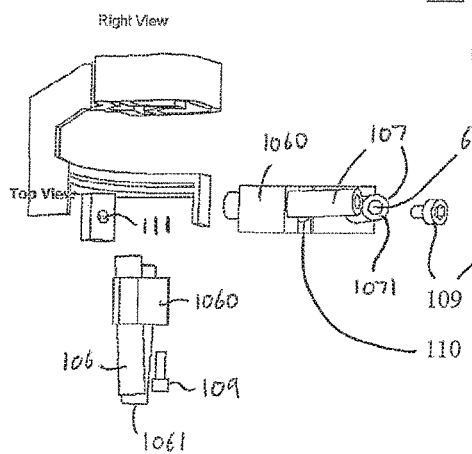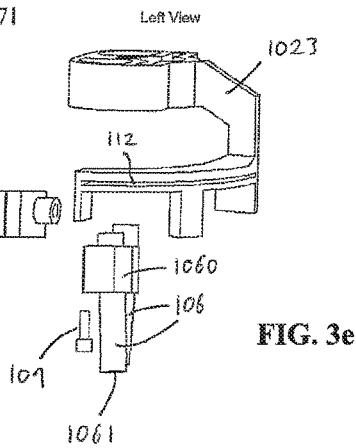

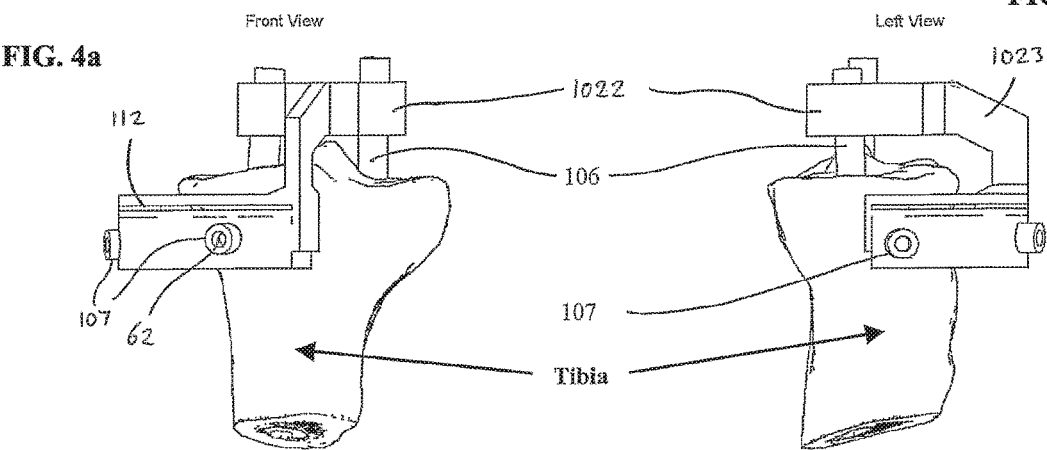
FIG. 4a
FIG. 4b
FIG. 4c
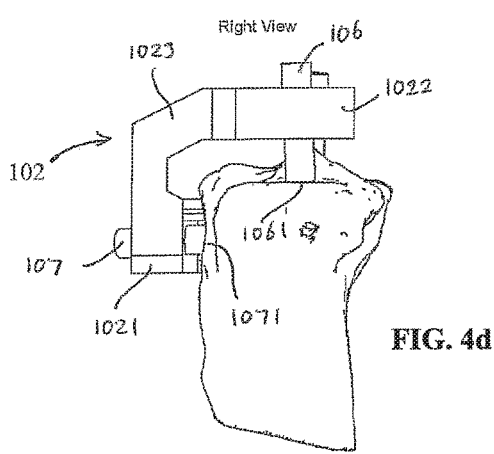
FIG. 4d
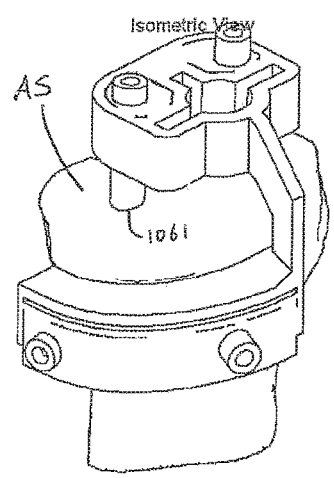
FIG. 4e

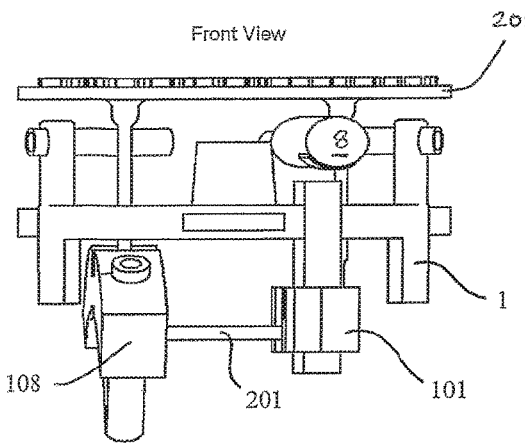
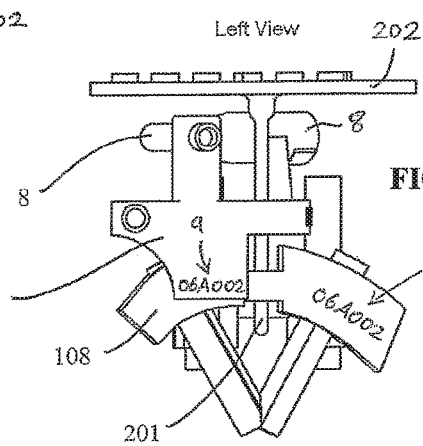
FIG. 5a
FIG. 5b
FIG. 5c
FIG. 5d

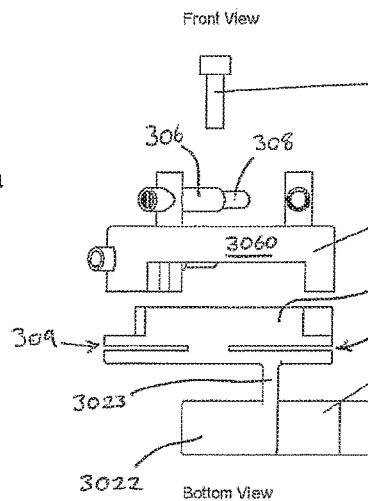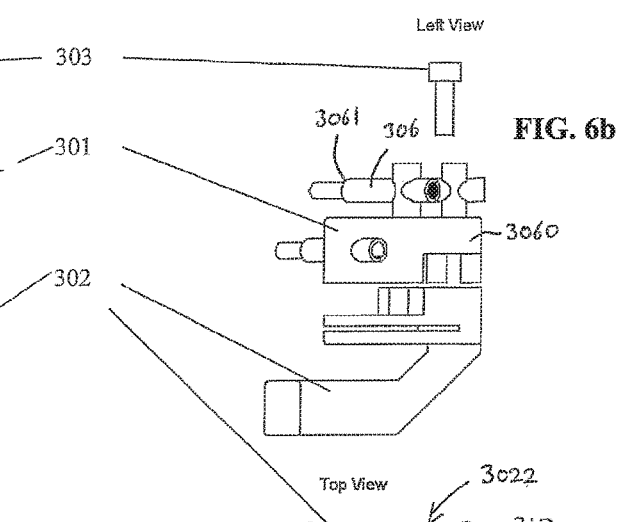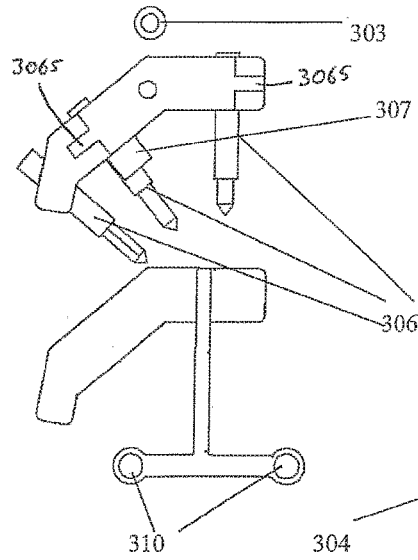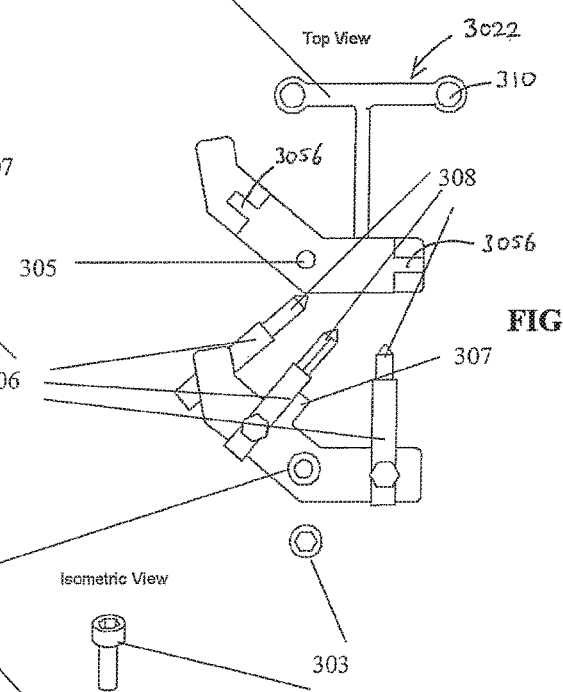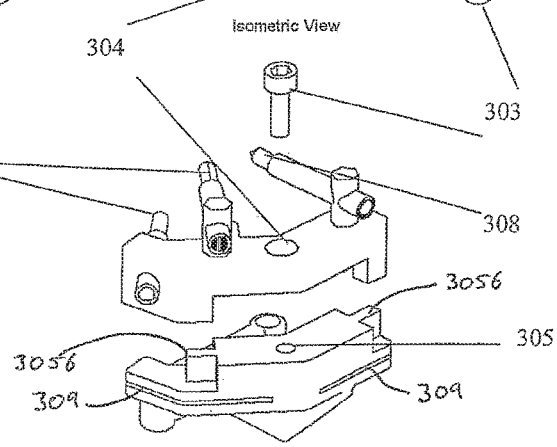

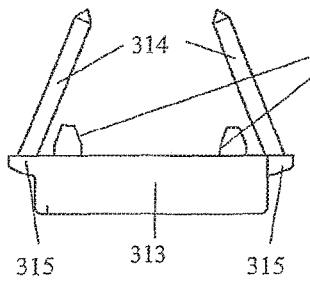
FIG. 8a
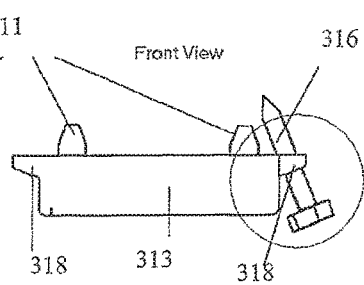
FIG. 8b
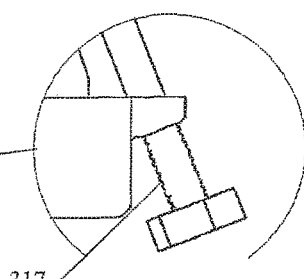
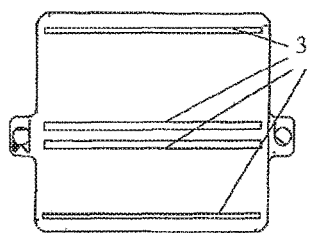
FIG. 8c
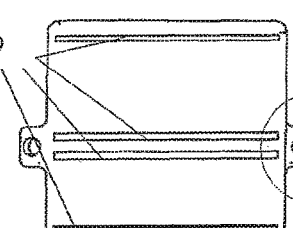
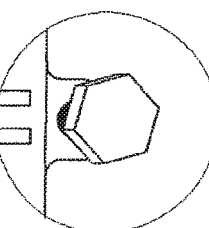
FIG. 8d
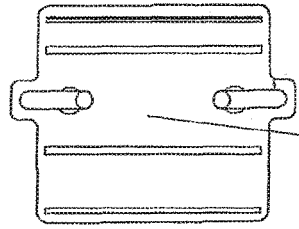
FIG. 8e
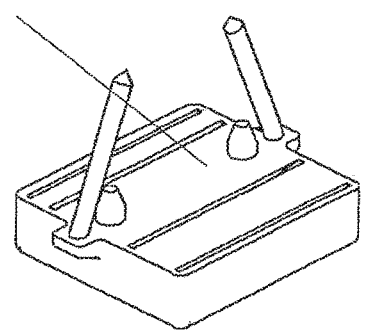
FIG. 8f

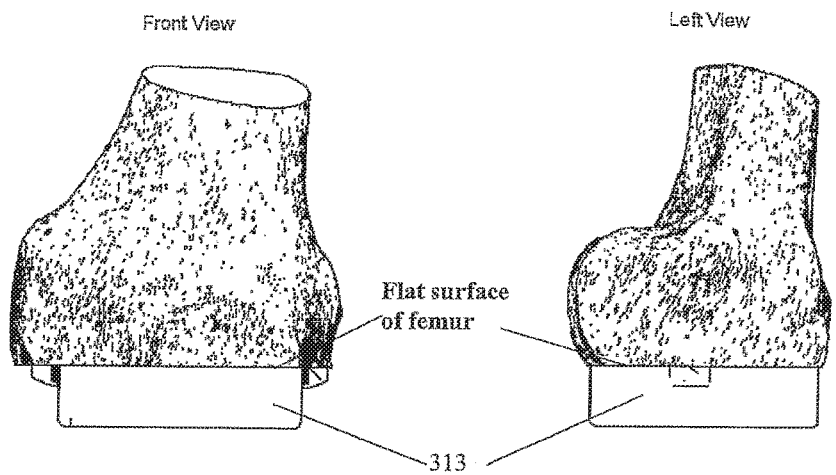
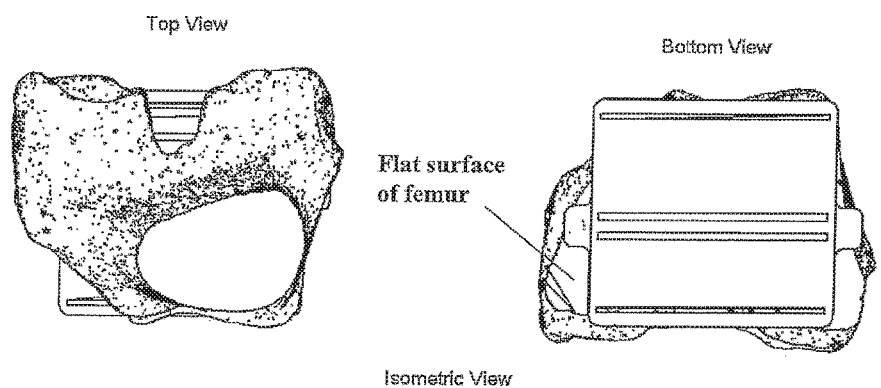
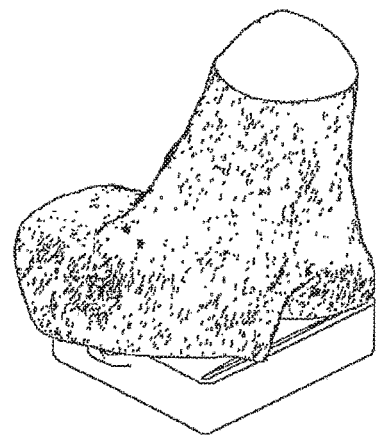
FIG. 9a
FIG. 9b
FIG. 9c
FIG. 9d
FIG. 9e

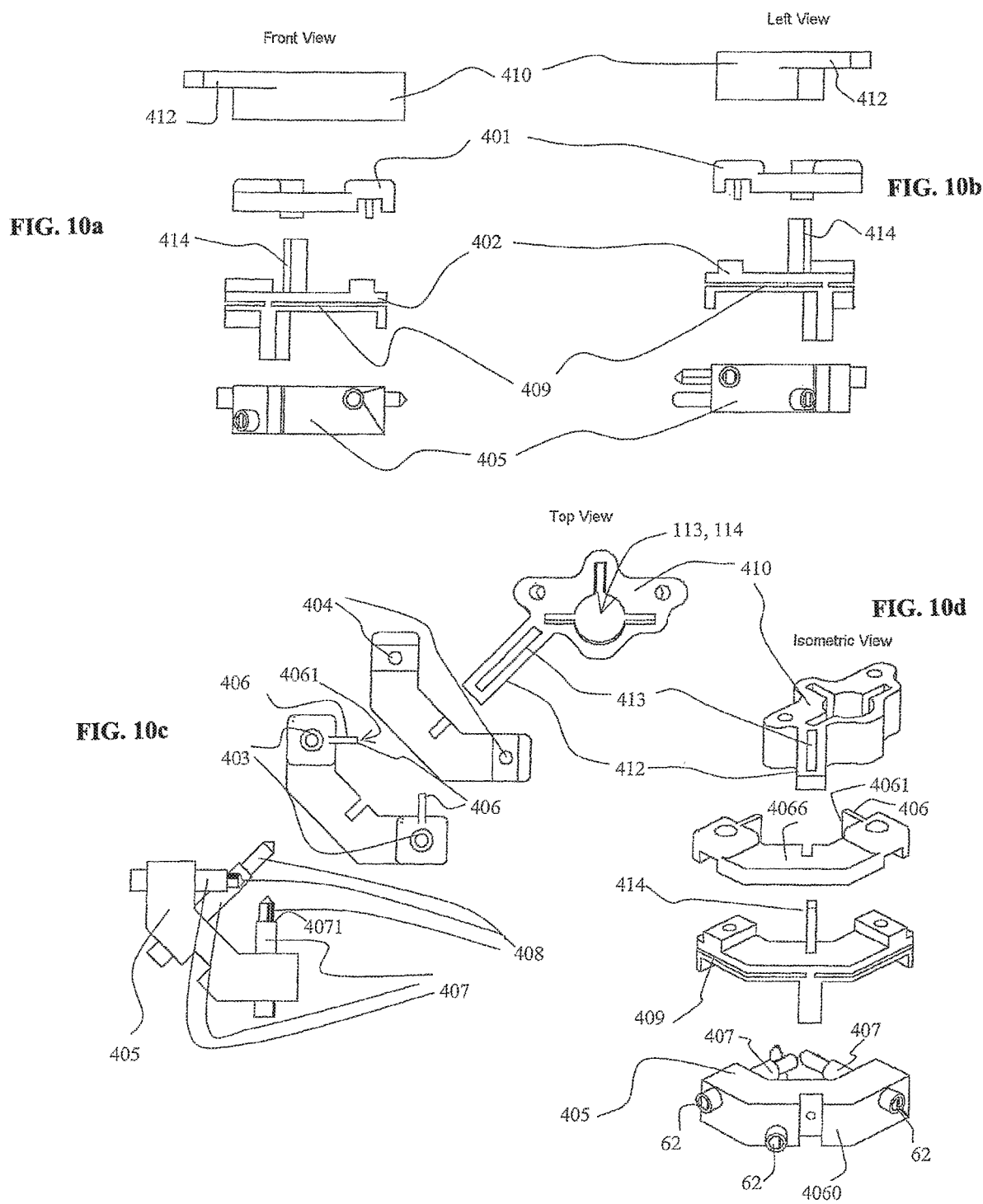

Tibia with finished tibial cut

Front View

Left View

Top View

Isometric View

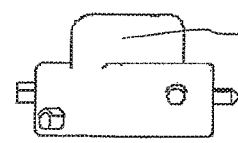
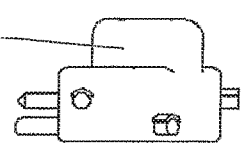
FIG. 15a
FIG. 15b
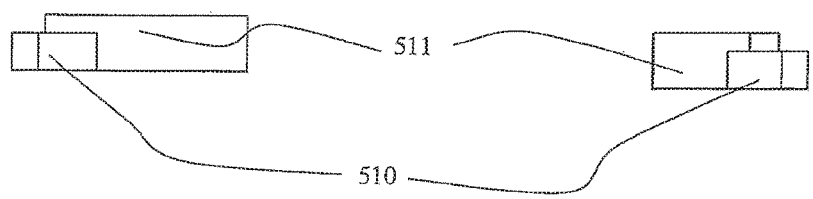
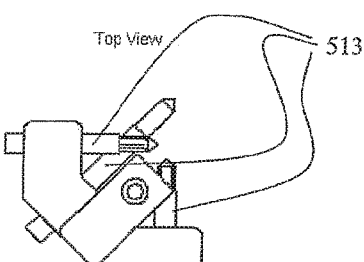
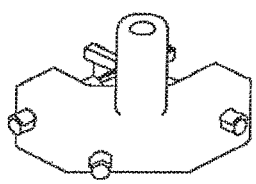
FIG. 15c
FIG. 15d
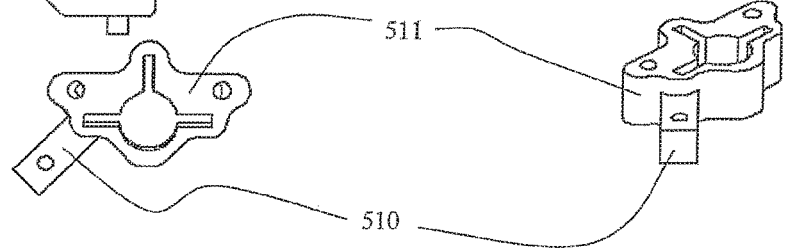

Figure 17: Summary of required steps
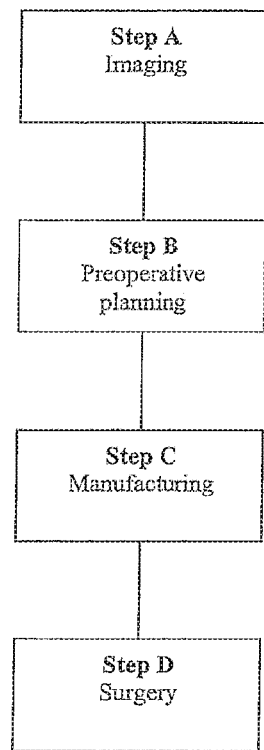

Step B: Preoperative planning

Step C: Manufacturing

Step D: Surgery

FIG. 21a
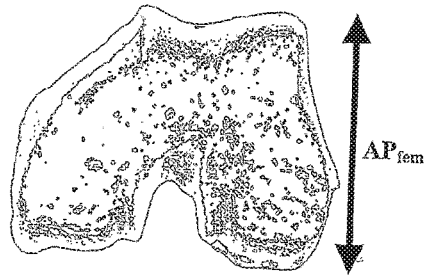
FIG. 21b
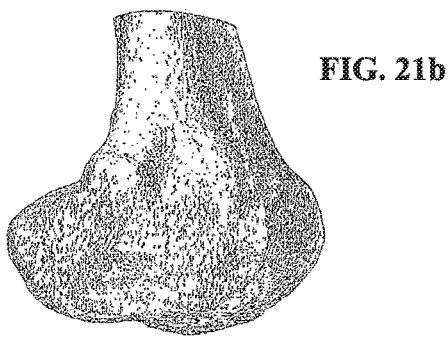
FIG. 21c
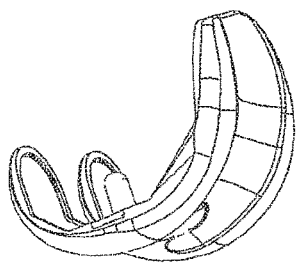
FIG. 21d
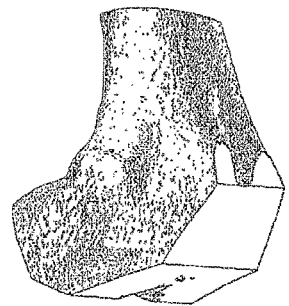
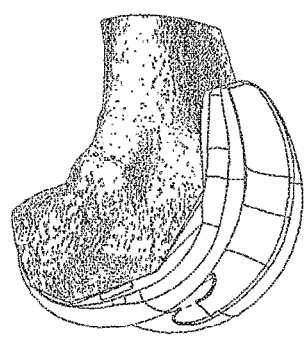
FIG. 21e FIG. 23a
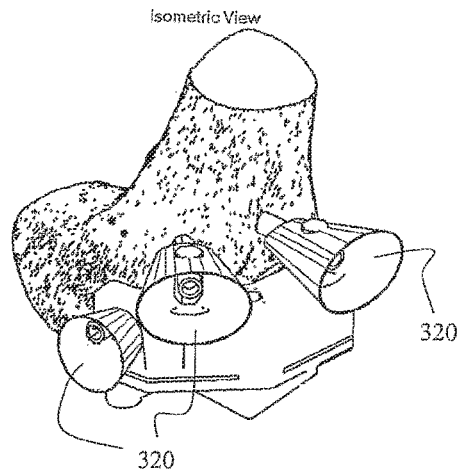
FIG. 23b
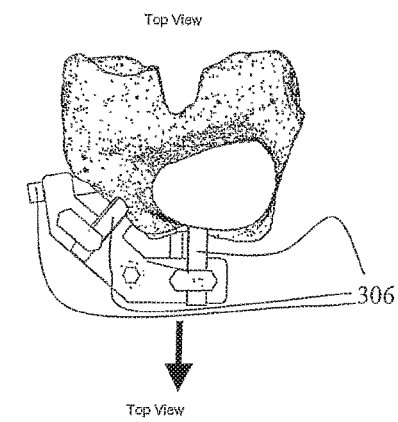
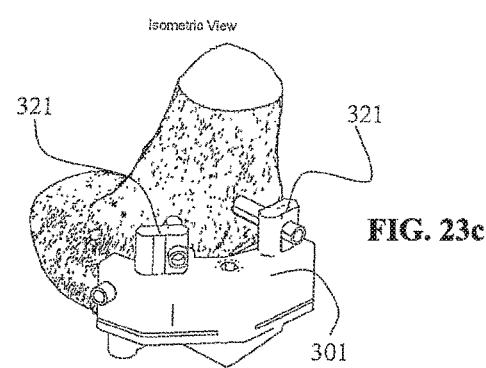
FIG. 23c
FIG. 23d
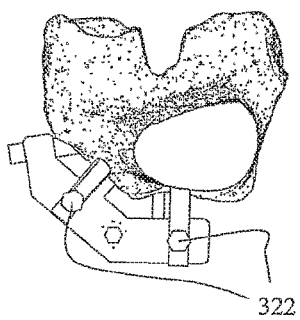
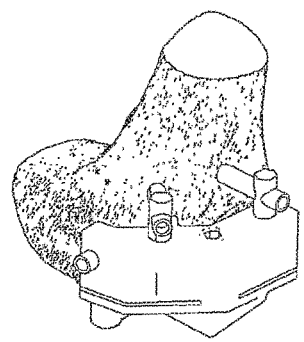
FIG. 23e

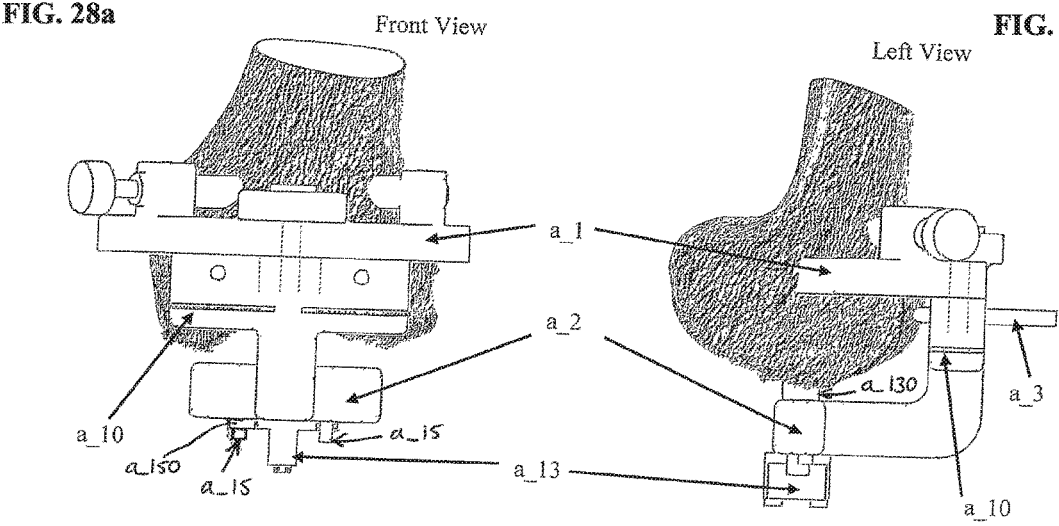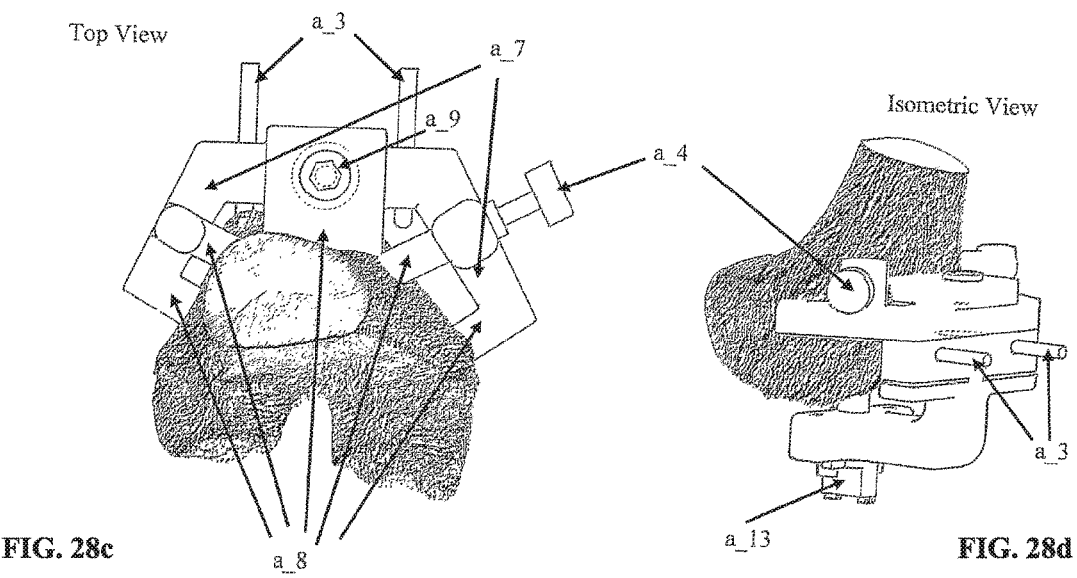
FIG. 28a Front View
FIG. 28b Left View
FIG. 28c Top View
FIG. 28d Isometric View

FIG. 29c FIG. 29d

FIG. 30a
Bottom View
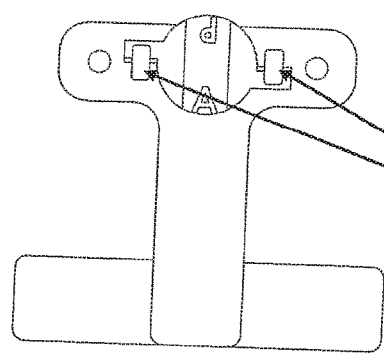
FIG. 30b
Left View
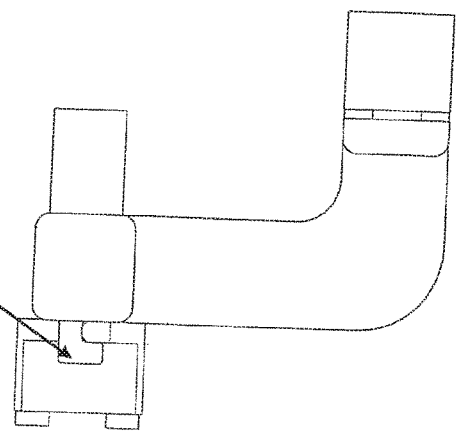
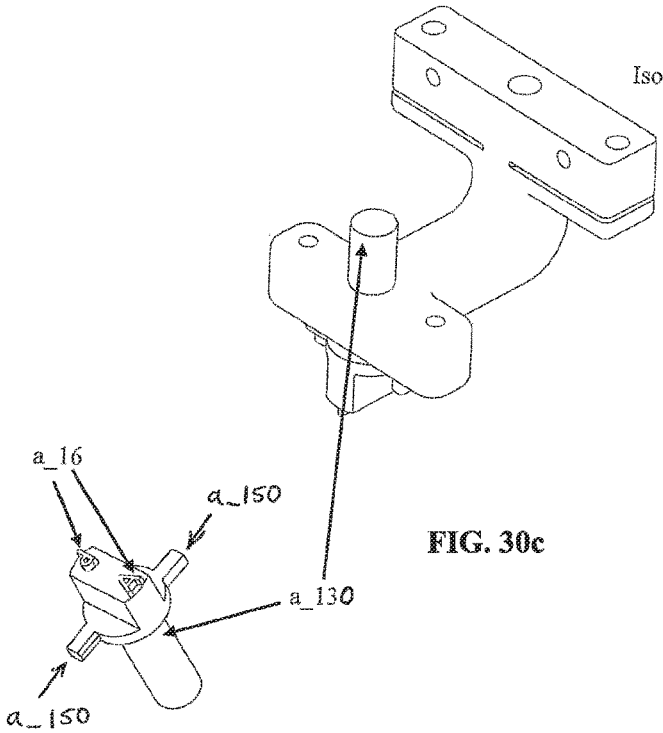
Isometric View
FIG. 30c

FIG. 35a
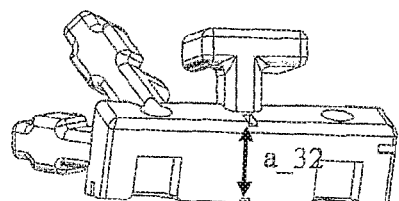
FIG. 35b
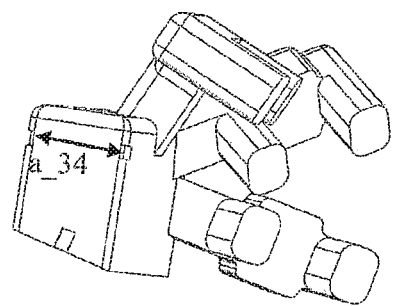
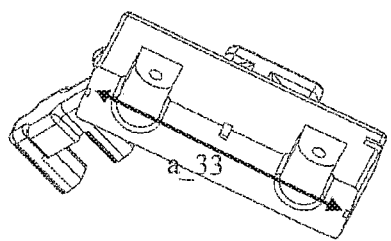
FIG 35c

SURGICAL TEMPLATES

CROSS REFERENCE TO RELATED APPLICATIONS

The present application is a continuation of U.S. patent application Ser. No. 15/491,853, filed Apr. 19, 2017, which is a continuation of U.S. patent application Ser. No. 15/012,550, filed Feb. 1, 2016, now abandoned, which is a continuation of U.S. patent application Ser. No. 14/531,825, filed Nov. 3, 2014, now U.S. Pat. No. 9,265,511, which is continuation of U.S. patent application Ser. No. 13/937,079, which was filed Jul. 8, 2013, now U.S. Pat. No. 9,125,675, which is a continuation of U.S. patent application Ser. No. 12/532,817, filed Mar. 11, 2010, now U.S. Pat. No. 8,496,663, which is the U.S. National Stage Application of International Application No. PCT/GB2008/000988, filed Mar. 20, 2008, which in turn claims the benefit of Great Britain Application No. GB0705613.8, filed Mar. 23, 2007. The prior applications are incorporated herein by reference.

FIELD OF THE INVENTION

The present invention relates to surgical template systems for use in working on bones, and in particular, although not exclusively, to surgical template systems for use in total knee replacement surgery.

BACKGROUND TO THE INVENTION

Surgical template systems for use in working on bones, and for preparing bones to receive prosthetics are known.

WO 2004/017842 A2 discloses template systems for use in total knee replacement surgery. The template systems comprise an adjustable positioning block and a surgical tool guide. The systems are designed to allow further adjustment after placement on the bone and have mechanisms which allow this to occur. Disclosed positioning blocks sit on articular surfaces of bones, and this may lead to inaccuracies in placement. A disclosed adjustable positioning block comprises a tracker member which, in use, is tracked by a camera-based optical computer assisted surgery (CAS) system to assist the surgeon in correctly positioning the template system. Thus, use of the template systems entails adjustments of at least the positioning block in the operating theatre. This is disadvantageous because it is likely to increase both the complexity and time of the implantation procedure and adds to the number of intra-operative decisions to be made by the surgeon. Furthermore, the apparatus of the template system itself and the associated tracking equipment is complex and costly. Adjustable mechanisms are more expensive to manufacture than fixed, non-adjustable systems, are more prone to failure, and are harder to clean after use.

WO 2006/060795 A1 discloses a surgical template comprising an alignment guide, in the form of a mold having a surface for engaging a joint surface, and an instrument guide, comprising one or more tool-guiding apertures, that communicates with the mold. The mold (alignment guide) may be designed specifically for a given patient and is used to help orientate an instrument guide relative to the patient's anatomy. For knee surgery, each mold is adapted to conform to an articular surface of the femur or tibia. The instrument guide may be manufactured from a hard material and may be re-usable, whereas the alignment guide may be formed from a relatively soft material. Optional adjustment between the alignment device and the instrument guide during the surgical procedure is disclosed. Optional use of a metal insert in an opening in a plastic mold to accept a reamer or saw is disclosed. Where the instrument guide is positioned over the mold, such that a tool guided by the instrument guide needs to pass through the mold to reach the bone beneath, the document discloses the option of arranging for openings in the plastic mold (alignment guide), corresponding to the instrument guide opening positions, to be oversized to avoid introducing plastic debris into the joint being worked on.

Disadvantages of the disclosed templates include the following. The custom (patient-specific) mold parts of both the femoral and tibial devices are adapted to conform with and sit on their articular surfaces. This can lead to inaccuracies in placement. During knee surgery the oscillating saw blade causes any device in contact with the joint to vibrate. In the disclosed systems in which the instrument guide blocks sit directly on top of the moulded parts, a problem is how to fasten the guide block to the mold so as not to come apart whilst the bone cuts are made. Positioning the instrument guide block on top of (over) a custom mold can move a guide aperture away from the bone surface, and can thus result in reduced accuracy when using that aperture to guide a cut. Furthermore, relatively thin (in terms of the depth of guide aperture provided) instrument guide blocks are disclosed, and by providing relatively shallow guide apertures, the accuracy of the bone cuts that can be made using those guide apertures if reduced. This is also exacerbated when the instrument guide block is located over the mold, such that a guided tool must also pass through the mold to reach the bone as the saw blade passes through the slits in them. The tibial and femoral devices sitting over the articular surfaces restrict the visibility of the surgeon whilst performing the bone cuts. A disclosed femoral mold, adapted to conform to the femoral articular surface, would appear to have to be made from flexible material to fit onto the end of the femur (which is, as a rough approximation, bell shaped). A flexible mold cannot be used to provide rigid location for an instrument guide block, and hence further inaccuracies in cutting the bone are introduced.

The paper "Computer-assisted Total Knee Arthroplasty Using Patient-specific Templating", M. A. Hafez et al, Clinical Orthopaedics and Related Research, No. 444, pp. 184-192 discloses femoral and tibial templates for total knee replacement surgery. This paper discloses one femoral and one tibial template, each customized to an individual bone by a process comprising scanning, and each then manufactured by a rapid prototyping technique. Each template is a one-piece block, comprising locators having surfaces adapted to seat the template in a unique position on the respective bone, and also comprising guide slots and holes to guide saw blades and drill bits to work on the bone. Each template is designed for single use (i.e. after that use it is disposed of). The paper discloses use of the templates to perform total knee arthroplasties on cadaveric and plastic knees only. The templates are produced from a Polyamide (nylon) composite material (DuraForm™, 3D Systems), which is a durable material for creating functional (tooling) prototypes. This material is licensed for in vivo exposure, i.e. coming into contact with tissue when used as an instrument, but not as an implant. Once manufactured, the templates are sterilized and ready for use. The paper demonstrates the usefulness and some of the advantages of patient specific templates. However, disadvantages of the disclosed templates include the following. The relatively soft material used to form each of the single unit templates, and which therefore forms the walls of the guide apertures, readily sheds particulate material when in contact with moving tool bits (e.g. saw blades, drill bits), which is unacceptable as it might in the long term have an undesirable toxic effect on the tissues of a patient. Further, the particulate matter might cause damage to the plastic prosthetic component if trapped between the two prosthetic components while they are in use. Friction between the moving surgical tools and the device can cause further shedding of particulate material from the device and would generate sufficient heat that can melt DuraForm™ under normal operating conditions. This melting of the device material can cause seizure of the cutting tool. DuraForm™ is porous. The inclusions in the material may be 'opened up' during surgery by the movement of powered surgical tools over its surface resulting in the release of more particulate material with the consequences stated above. It is now possible to rapid prototype customized devices using stainless steel resulting in non-porous devices. However, constructing each device as a single unit, for the purpose of single use is extremely expensive and this option is therefore not likely to be cost effective. Lastly, the templates disclosed in the paper are relatively bulky, and substantially reduce visibility of the femur and tibia being worked on.

Embodiments of the present invention aim to obviate or mitigate at least one of the problems associated with the prior art.

SUMMARY OF THE INVENTION

According to a first aspect of the present invention there is provided a surgical template system for use in working on a bone, comprising:
  a tool guide block comprising at least one guide aperture for receiving and guiding a tool to work on a bone;
  locating means comprising a plurality of locating members, each member having a respective end surface for positioning against a surface of the bone; and
  attachment means for non-adjustably (and, preferably, releasably) attaching the tool guide block to the locating means such that, when attached, the member end surfaces are secured in fixed position with respect to each other, for engaging different respective portions of the surface of the bone, and the at least one guide aperture is secured in a fixed position with respect to the end surfaces.

As the locating means and tool guide block are separate from one another (and must be assembled and attached together to use the template) they can be manufactured separately and this provides a number of advantages. Firstly the tool guide block may be manufactured as a hardwearing, reusable component that is not patient-specific. It can, for example, be manufactured from a metal, such that the guide apertures have hard metal surfaces which can guide a moving tool (such as a vibrating or reciprocating saw blade or rotating drill bit) without shedding material. The locating means can be made separately, by different techniques and, for example, using different material. For example, the locating means may be manufactured using rapid prototyping techniques so as to be patient-specific, based on a predetermined bone shape, that is a bone shape, topography or geometry that has been determined by a suitable technique on the patient, such as by scanning (which may also be referred to as imaging). Thus, a patient-specific system can be produced by rapid prototyping of just the locating means, and not the tool guide block. This helps speed up the process and also reduces costs. In other words, embodiments of the invention offer the advantage that just some parts of the template system need be patient-specific, with other parts being "standard" i.e. predetermined and possibly reusable components. Advantageously, as the guide aperture or apertures are provided in the tool guide block and not in the patient-specific "custom" locating means, material can be used for the locating means that is suited to the patient-specific manufacturing technique (for example it may be a relatively soft plastic) whilst avoiding the problem of locating means material shedding during use, as the tools are guided by the guide block apertures.

It will be appreciated that the locating members of the locating means are rigid such that the assembled guide block and locating means seats securely on a bone to be worked on in a predetermined, defined position.

In certain embodiments the attachment means is adapted to releasably and non-adjustably attach the tool guide block to the locating means.

In certain embodiments the locating means is adapted such that when attached to the tool guide block the locating member end surfaces conform to different respective portions of a predetermined bone surface and enable the attached locating means and tool guide block to be seated in a defined position with respect to said predetermined bone surface, with each member end surface in contact with its respective portion of the bone surface.

In certain embodiments the locating means has been manufactured using a method comprising:
  determining a surface shape (topography, geometry) of a bone to be worked on;
  manufacturing the locating means according to the determined shape such that when the locating means is attached to the tool guide block the locating member end surfaces conform to different respective portions of the bone surface and enable the attached locating means and tool guide block to be seated in a defined position with respect to the bone, with each member end surface in contact with its respective portion of the bone surface.

In certain embodiments the locating means is patient specific, in that the end surfaces of the locating members are adapted to conform to a predetermined surface of a specific bone of a patient when the locating means is attached to the tool guide block, so as to enable the attached locating means and tool guide block to be seated in a defined position with respect to the specific bone, with each member end surface in contact with a respective portion of the bone surface.

A plurality of the member end surfaces may be adapted to be in contact with respective portions of a non-articular surface of the bone when the attached locating means and tool guide block are seated in said defined position. In certain embodiments all of the locating members are arranged to seat against non-articular surfaces of the bone. This is advantageous, because in general the non-articular surface can be more precisely determined from scanning, and thus enables the template to be manufactured such that it locates on the bone in a substantially unique position. However, in certain other embodiments, at least one of the locating member end surfaces is adapted to seat against an articular surface of the bone.

In certain embodiments the tool guide block is formed from a first material and the locating means is formed from a second, different material, and the first material may be harder than the second material. For example, the tool guide block may be formed from a metal, and the locating means may be formed from a non-metallic material, such as a plastic.

The locating means may have been formed by a rapid prototyping technique, e.g. from a non-metallic or a metallic material. Although rapid prototyping in metal is currently expensive, only the patient-specific locating means would need to be formed in this way, not the tool guide block as well. Thus, rapid prototyping of just the locating means in metal could be performed, at lower cost than if a unitary guide block and locating means were produced with such a technique. However, in many embodiments, the locating means is rapidly prototyped in non-metallic material.

In certain embodiments at least one of the locating members is generally cylindrical and/generally elongate. At least one of the locating members may be a locating finger.

In certain embodiments the locating means and guide block are arranged such that, when attached together, the/or each guide aperture is arranged to guide a tool so as to avoid the locating means. This avoids the shedding problem, even if the locating means is formed from a plastic or other relatively soft material.

The system may further comprise securing means for securing the attached locating means and tool guide block to a bone to be worked on. For example, at least one said member may comprise a bore extending through the member to the member's end surface, and the securing means may comprise a pin adapted to extend through the bore so as to be drivable into a bone surface to pin the member to the bone. Certain embodiments further comprise a sleeve arranged to line said bore, wherein the pin is adapted to extend through the sleeve. A plurality of said members (some or all) may comprise bores, and the securing means then comprises a corresponding plurality of pins.

In certain embodiments, the securing means comprises a bore extending through the tool guide block, and the system further comprises a pin adapted to extend through the guide block bore so as to be insertable into a bone surface to pin the guide block to the bone. The pin may be adapted so that it can be driven into the bone (for example with blows from a hammer or mallet). However, in alternative embodiments, the pin may be adapted to screw into the bone. As the tool guide block can be manufactured from material which does not pose any shedding problems when in contact with a moving (e.g. rotating) pin such embodiments of the invention can provide clear advantages.

The use of one or more securing bores and corresponding pins in the tool guide block itself can be in addition to bores and pins on the locating means, or an alternative. Thus, in certain embodiments the tool guide block may be secured to the bone independently of the locating means. In certain examples, having secured the tool guide block in this way at a position determined initially by the locating means, the locating means may be removed.

In certain embodiments the tool guide block comprises a plurality of securing bores and corresponding pins. In certain examples, this plurality of bores comprises a pair of parallel bores arranged such that when their respective pins are inserted into the bone they constrain the tool guide block in directions transverse to the bores but not in a direction along those bores. In certain cases, if the locating means is detached from the tool guide block the tool guide block may then be slid off the parallel attachment pins, and if desired could be replaced by another tool guide block with one or more tool guide apertures arranged to provide cutting or drilling (or otherwise working) on the bone at a modified position.

In certain embodiments each bore extending through a member is arranged so as to be generally perpendicular to a respective portion of the surface of a predetermined bone against which the respective end surface is adapted to seat. This helps the pins to be driven into the bone without skidding, so maintaining the accurate placement of the template system on the bone.

In certain embodiments the locating means and guide block are arranged such that, when attached together, the/or each guide aperture is arranged to guide a tool so as to avoid the locating means and the or each pin when driven into a bone surface. In other words, the system is designed so that the locating members and pins driven through the bores avoid any of the cut surfaces and holes that are produced when the guide apertures are used.

In certain embodiments, at least one guide aperture comprises at least one slot for guiding a saw blade. The slot may be an open-ended slot. This facilitates insertion of a saw blade into the slot and also enables the overall size of the guide block to be reduced as slot-closing material at at least one end of the slot is dispensed with. It also allows completion of the bone cuts without the need to remove the attached template.

At least one guide aperture may be a hole for guiding a drill bit, and in certain embodiments the tool guide block comprises a plurality of guide apertures.

The locating members may be separate components, and the relative positions of their end surfaces may only be defined when they are attached to the tool guide block. However, in certain other embodiments the locating means comprises a body portion with a plurality of the locating members attached to that body portion and extending from it to their respective end surfaces. The attachment means may then be adapted to attach the body portion to the tool guide block. The body portion and the locating members extending from it may be integral.

By manufacturing this body portion and plurality of locating members as a single unit, this provides the advantage that the relative positions of the end surfaces of those members extending from the body portion are completely fixed, even before the body portion is attached to the tool guide block. Thus, their relative positions cannot be affected by any tolerances involved in attachment of the body portion to the guide block, and hence the integral body portion and locating members help seat the assembled template system in the desired, substantially unique position on the bone.

Achieving placement of a customised template component on its respective bone requires careful consideration of the number and position of the locators. The following applies to the component customised for the femoral bone, but it will be appreciated that the general features may be applicable to other bones. The customised template component may have four locators, two on the medial side and two on the lateral side. While the template component might be placed such that the four locators are simultaneously in contact with the bone, there is still the possibility that the template may be incorrectly placed; because of the presence of a slippery soft tissue layer (albeit thin) on the bone surfaces, this may render the contact between the locators and bone surfaces to be soft and consequently the template may be pushed further in the posterior and inferior directions, thus resulting in inaccuracies in cutting the bone. This can have serious consequences, especially if the movement in the posterior direction is large, as it could result in violating the anterior cortex of the femur. For this reason, in another embodiment of the invention there may be included two additional locators, each of which may be arranged to limit the movement of the template in one of the two directions mentioned above. During surgery, should either of these additional locators be in contact with soft tissue, the latter could be removed so that the locator is in contact with bone. This concept is also applicable to the tibial template, and of course to other templates for working on other bones. Thus, during surgery, if it is determined that a locator would be seated on relatively soft material, the surgeon may remove the soft material with a scalpel so as to properly seat the locator on a hard bone surface.

In certain embodiments the locating means further comprises an additional locating member having an end surface for positioning against a bone surface, and means for releasably attaching the additional locating member to the body portion such that the additional locating member extends from the body portion to its end surface, whereby the additional locating member may be attached to the body portion to assist in seating the attached locating means and guide block against a bone to be worked on, and then removed to facilitate working on the bone. Whereas the other locating members may be arranged so that they are avoided by tools guided by the guide aperture or apertures in the tool guide block, the additional locating member may not be avoided, for example it may be in line with a guide slot such that a saw blade guided by that slot would intersect the additional locating member. However, as the additional locating member is releasably attached, it can be removed after locating the assembled template system on the bone and securing it in place. In this manner it can assist a surgeon in positively locating the template system on the bone in the required position and yet, by being removable, still avoids the potential shedding and contamination problems.

In certain embodiments the body portion and guide block are adapted to key together in a defined position, so as to assist in fixing the relative positions of locator end surfaces and guide apertures.

The attachment means may, for example, comprise at least one screw or bolt.

In certain embodiments the attachment means comprises a snap-fit mechanism. This may be arranged to allow the custom and re-usable parts to be securely and quickly attached to one another without the use of bolts or screws (or alternatively could be used in addition to bolts or screws). In certain examples, the snap-fit mechanism may be such that additional devices may be required to separate the two components once attached (or to bring the components together). In certain embodiments, in order to separate the custom part (locating means) from the re-useable part (tool guide block) it may be necessary to break the custom part (or at least some component, element or part of the snap-fit mechanism). It is conceivable that in further alternative embodiments, the locating means may be removable from the tool guide block in alternative ways, for example by dissolving the locating means material.

In certain embodiments the tool guide block comprises a first portion including at least one guide aperture and a second portion including at least one guide aperture. The tool guide block may then further comprise a connecting portion, connecting said first portion to the second portion, and this connecting portion may be adapted to improve visibility of the joint being worked on. For example, it could be perforated, transparent, or have reduced width and/or thickness compared with the first and second portions. It could have a depth greater than its width, said depth being in a direction generally toward the bone to be worked on, and said width being in a direction generally transverse to the bone. It may, for example be provided by a single web.

Thus, the connecting portion may comprise a web. This web may also be described as an arm.

By connecting the first and second portions using a single web or arm, the surgeon is provided with improved access and visibility of the bone being worked on. It will be appreciated that the web or arm must provide rigid connection of the first and second portions so that the relative positions of the respective guide apertures are fixed and well defined. The separate guide block and locating means of embodiments of the invention makes this possible because suitable materials for forming a rigid connecting web can be used in the manufacture of the guide block and which would be unsuited to the manufacture of the patient-specific locating means. In particular, the first, second, and connecting web portions of the guide block may be manufactured from a metal, and may indeed be manufactured as a single, integral unit. At least one of the guide apertures may be a slot having a length, and the web may have a thickness substantially smaller than that length.

In certain embodiments first portion comprises at least one slot for guiding a saw blade to make a cut in a plane, and said second portion comprises at least one slot or guide hole for guiding a saw blade or drill bit respectively to make a cut or hole in a direction substantially perpendicular to said plane.

The first portion may include a guide slot for guiding a saw blade to cut off an end portion of a bone against which the assembled locating means and guide block are positioned and said second portion includes a plurality of guide holes to guide a drill bit to drill into the sawn end surface.

In certain embodiments the system is a femoral system (i.e. for working on a femur), in which the locating means is arranged such that, when attached to the tool guide block, the member end surfaces are positioned to seat the locating means and guide block in a predetermined position on a specific femur by engaging non-articular surface portions of the femur. The tool guide block may then comprise a first portion including a guide slot for guiding a saw blade to cut off an end portion of the femur to leave a sawn end surface when the block and locating means are seated in the predetermined position, and a second portion including a plurality of guide holes to guide a drill bit to drill into the sawn end surface. The second portion may further comprise at least one guide slot for guiding a saw blade to make at least one further cut in the femur. The locating means may comprise an additional locating member having an end surface for positioning against a non-articular anterior surface (i.e. the cortical bone surface just above the trochlea; this may be more accurate than just seating against the trochlea, as this may well have cartilage residues, as thick as 2-4 mm, that would affect the accuracy) of the femur. Advantageously, this additional locating member adapted to sit on the above mentioned anterior cortical bone surface of the femur may be arranged so that it extends through a cut plane defined by one of the guide slots in the guide block. By positioning the end of the additional locating member against the said anterior surface of the femur to locate the assembled template system in the required position, this then ensures that the above-mentioned cut plane is away from the anterior surface (ensuring that the saw blade when guided by that aperture does not violate the anterior cortex of the bone). The additional locating member can then be removed after the template system has been secured in place. Thus, the system may further comprise means for releasably securing the additional locating member with respect to the guide block and locating member end surfaces, whereby the additional locating member may be secured in place to assist in seating the attached locating means and guide block against the femur, and then removed to facilitate working on the femur.

Other embodiments provide a tibial template system, in which the locating means is arranged such that, when attached to the tool guide block, a plurality of said member end surfaces are positioned to seat the locating means and guide block in a predetermined position on a specific tibia by engaging non-articular surface portions of the tibia. It may employ further locators to seat on articular surface portions as well.

In certain embodiments the locating means comprises a first body portion and a first plurality of said locating members extending from the first body portion to their respective end surfaces, and a separate second body portion and a second plurality of said locating members extending from the second body portion to their respective end surfaces, and the attachment means is adapted to attach said first body portion to the tool guide block and said second body portion to the tool guide block. The first body portion and the first plurality of said locating members may be integral, as may the second body portion and the second plurality of locating members.

In certain embodiments the tool guide block comprises a first portion including at least one guide aperture and a second portion including at least one guide aperture, the tool guide block further comprises a connecting portion connecting said first portion to the second portion, and the attachment means is adapted to attach said first body portion to the first portion of the tool guide block and said second body portion to the second portion of the tool guide block. The first portion of the guide block may be adapted to extend around an arc of less than 100 degrees and/or may be generally arcuate. The connecting portion may comprise a web portion connected at or proximal one end of the first portion. Thus, the guide block may be asymmetrical, being suited to use in surgery on the bone requiring access to the bone from essentially just one quadrant.

In certain embodiments the second portion of the guide block comprises a composite guide aperture comprising a hole portion for guiding a drill bit to drill a hole in a bone, and at least one slot portion for guiding a saw blade to make a cut extending from said hole.

Certain embodiments are adapted for working on a tibia, wherein the end surfaces of the first plurality of locating members are adapted to seat on respective portions of a non-articular surface of a specific tibia and the end surfaces of the second plurality of locating members are adapted to seat on respective portions of an articular surface of the specific tibia.

In certain embodiments the tool guide block is a first tool guide block, the system further comprising a second tool guide block including at least one additional guide aperture. Such an arrangement is particularly suited to the requirements of minimally invasive surgery because the total number of guide apertures required to guide tools to prepare the bone in a desired manner to receive a prosthesis can be split between the first and the second blocks, thus enabling each block to be made substantially smaller than the single block that would otherwise be required to define all of the necessary guide apertures. It also provides the advantage that, as the first guide block provides only one or some of the guide apertures, rather than all of them, it gives greater freedom in the locating means manufacturing process to provide a plurality of locating members to securely seat the template system in the required position whilst keeping those locating members out of the way of tools guided by the guide aperture or apertures. In other words, the two-block template system provides a greater degree of flexibility during the custom locating means design process.

The first tool guide block may comprise at least one guide slot for guiding a saw blade to cut a bone to provide a flat surface and at least one guide hole to guide a drill bit to drill at least one hole in the flat surface, and the second tool guide block has a flat surface adapted to sit on the bone flat surface prepared using the first tool guide block and comprises at least one protruding member extending from the block flat surface to locate in the at least one hole, to locate the second guide block on the bone flat surface.

In certain embodiments the first tool guide block further comprises mounting means for mounting the second guide block on the first guide block after the first guide block has been used to guide at least one tool to work on the bone.

In certain embodiments the locating means comprises an additional body portion and at least one additional locating protrusion extending from the additional body portion and having an additional end surface for locating against an additional bone surface portion to help seat the locating means and attached guide block on the bone, and wherein the attachment means is adapted to releasably and non-adjustably attach the additional body portion to the guide block.

In certain embodiments the locating means further comprises at least one feature having a dimension measurable to check a manufacturing accuracy of the locating means.

In certain embodiments, the locating means further comprises at least one paid of indicia having a separation measurable to check the manufacturing accuracy of the locating means.

In certain embodiments, the system further comprises a gauge adapted to engage the locating means to provide a check on a manufacturing accuracy of the locating means. The locating means may comprise at least one feature adapted to mate with the gauge to provide this check.

Another aspect of the present invention provides a method of manufacturing a surgical template system for use in working on a bone, the template system comprising a tool guide block comprising at least one guide aperture for receiving and guiding a tool to work on a bone, locating means comprising a plurality of locating members, each member having a respective end surface for positioning against a surface of the bone, and attachment means for non-adjustably (and, preferably releasably) attaching the tool guide block to the locating means such that, when attached, the member end surfaces are secured in fixed position with respect to each other, for engaging different respective portions of the surface of the bone, and the at least one guide aperture is secured in a fixed position with respect to the end surfaces, the manufacturing method comprising:

determining a surface shape of a bone to be worked on;

manufacturing the locating means according to the determined shape such that when the locating means is attached to the tool guide block the locating member end surfaces conform to different respective portions of the bone surface and enable the attached locating means and tool guide block to be seated in a defined position with respect to the bone, with each member end surface in contact with its respective portion of the bone surface.

In certain embodiments, the manufacturing of the locating means further comprises manufacturing the locating means according to the determined shape such that a plurality of said member end surfaces are adapted to be in contact with respective portions of a non-articular surface of the bone when the attached locating means and tool guide block are seated in said defined position.

At least one member end surface may be adapted to be in contact with a portion of an articular surface of the bone when the attached locating means and tool guide block are seated in said defined position.

The method may comprise manufacturing the tool guide block from a first material (e.g. a metal) and manufacturing the locating means from a second, different material (e.g. using a rapid prototyping technique).

In certain embodiments the method further comprises manufacturing the locating means and guide block such that, when attached together, the/or each guide aperture is arranged to guide a tool so as to avoid the locating means. At least one member may be manufactured to comprise a bore, such that a pin can be driven through the bore into the bone surface to secure the locating means to the bone, and each guide aperture may then be arranged to guide a tool so as to avoid the or each pin driven into the bone through a respective bore. In certain embodiments each bore is arranged so as to be generally perpendicular to a respective portion of the surface of said bone against which the respective end surface is adapted to seat.

In certain embodiments, manufacturing the locating means comprises manufacturing a body portion and a plurality of said locating members attached to and extending from the body portion to their respective end surfaces, for example as an integral unit.

In certain embodiments, manufacturing the locating means further comprises manufacturing an additional locating member according to the determined shape, the additional locating member having an end surface for positioning against the bone surface, and the method further comprises providing means for releasably attaching the additional locating member to the body portion such that the additional locating member extends from the body portion to its end surface, whereby the additional locating member may be attached to the body portion to assist in seating the attached locating means and guide block against the bone to be worked on, and then removed to facilitate working on the bone.

In certain embodiments the tool guide block comprises a first portion, comprising at least one guide aperture, a second portion, comprising at least one guide aperture, and a connecting portion connecting said first portion to the second portion, the method comprising manufacturing the first, second, and connecting portions as an integral unit.

In certain embodiments the bone is a femur. The additional locating member end surface may then be arranged for positioning against an anterior surface of the femur.

In certain other embodiments the bone is a tibia.

The locating means may be manufactured such that, when attached to the tool guide block, a plurality of said member end surfaces are positioned to seat the locating means and guide block in a predetermined position on the bone by engaging non-articular surface portions of the bone, and optionally such that another plurality of said member end surfaces are positioned to seat the locating means and guide block in a predetermined position by engaging articular surface portions of the bone.

In certain embodiments manufacturing the locating means comprises manufacturing a first body portion and an integral first plurality of said locating members extending from the first body portion to their respective end surfaces, and a separate second body portion and an integral second plurality of said locating members extending from the second body portion to their respective end surfaces.

In certain embodiments, said step of determining a surface shape of the bone comprises non-invasive scanning of a patient.

Another aspect of the invention provides a method of manufacturing locating means for a surgical template system for use in working on a bone, the template system comprising a tool guide block comprising at least one guide aperture for receiving and guiding a tool to work on a bone, locating means comprising a plurality of locating members, each member having a respective end surface for positioning against a surface of the bone, and attachment means for non-adjustably (and, preferably, releasably) attaching the tool guide block to the locating means such that, when attached, the member end surfaces are secured in fixed position with respect to each other, for engaging different respective portions of the surface of the bone, and the at least one guide aperture is secured in a fixed position with respect to the end surfaces, the manufacturing method comprising:

determining a surface shape of a bone to be worked on;
manufacturing the locating means according to the determined shape such that when the locating means is attached to the tool guide block the locating member end surfaces conform to different respective portions of the bone surface and enable the attached locating means and tool guide block to be seated in a defined position with respect to the bone, with each member end surface in contact with its respective portion of the bone surface.

In certain embodiments of these methods, manufacturing the locating means comprises manufacturing at least one feature having a dimension, or at least one pair of indicia having a separation, measurable to determine a manufacturing accuracy of the locating means.

In certain embodiments, this at least one feature or pair of indicia is provided on the locating means itself. In alternative embodiments, the feature or pair of indicia may be provided on a portion of material attached to the locating means and manufactured integrally with the locating means. This portion of material may thus be described as an indicator, manufactured together with the locating means, and before the locating means is used in surgery this indicator may be detached from the locating means.

Another aspect of the invention provides a method of fitting a prosthesis to a bone, the method comprising:

manufacturing a surgical template system using a method in accordance with another aspect of the invention;
using the attachment means to attach the locating means to the tool guide block;
arranging the attached locating means and tool guide block such that they are seated in the defined position with respect to the bone;
using the at least one guide aperture to guide a tool to work on the bone to prepare the bone for receiving the prosthesis; and
fitting the prosthesis to the prepared bone.

The method may further comprise scanning a patient to determine the surface shape of the bone, and selecting the prosthesis from a plurality of prostheses. This plurality of prostheses may include prostheses having a variety of different sizes.

The method may further comprise selecting a desired position for the prosthesis relative to the bone.

In certain embodiments the method further comprises forming a virtual model of the bone and manipulating a virtual model of the selected prosthesis relative to the bone virtual model to determine the desired position. The selected prosthesis in certain embodiments has a defined interior surface shape, and the method further comprises using the selected desired position and the defined interior surface shape to determine the position of each guide aperture when the assembled template is seated in the defined position on the bone.

The method may further comprise selecting the tool guide block from a plurality of tool guide blocks, the selected block comprising a plurality of guide apertures corresponding to said defined interior surface shape.

Another aspect of the invention provides a surgical method comprising:
  manufacturing a surgical template system using a method in accordance with another aspect of the invention;
  using the attachment means to attach the locating means to the tool guide block;
  arranging the attached locating means and tool guide block such that they are seated in the defined position with respect to the bone;
  using the at least one guide aperture to guide a tool to work on the bone.

In certain embodiments the method further comprises using the tool guide block to guide a saw blade to cut a flat surface on the bone and to guide a drill bit to drill at least one locating hole in the cut flat surface, locating a second guide block on the cut flat surface and at least one locating hole, and using the second guide block to guide a tool to perform further work on the bone.

In certain embodiments the method further comprises mounting a second tool guide block comprising at least one guide aperture on the first guide block and using the second guide block to guide a tool to perform farther work on the bone.

Another aspect of the invention provides surgical apparatus comprising:
  locating means for a surgical template system in accordance with another aspect of the invention; and
  patient identification means providing an indication of the patient to whom said bone to be worked on belongs.

In certain embodiments, the patient identification means may be provided on the locating means, but in alternative embodiments the identification means may be linked to the locating means by linking means.

In certain embodiments the locating means comprises locating means for a template system for a femur and for a template system for a tibia for a specific knee joint of a particular patient.

In certain embodiments the locating means, patient identification means, and linking means have been manufactured together using a rapid prototyping technique.

In certain embodiments the surgical apparatus further comprises an indicator, manufactured together and integrally with the locating means, the indicator comprising at least one feature having a dimension measurable to check a manufacturing accuracy of the locating means. This indicator may, for example, be separable from the locating means before the locating means is used in surgery.

In certain embodiments, the apparatus further comprises a gauge adapted to engage the indicator and thus provide a quick check of the indicator dimensions and hence the accuracy of manufacture of the integrally formed locating means before use.

From the above summary, and the following description, it will be appreciated that embodiments of the invention provide a number of advantages, as follows. In certain embodiments, a template is essentially split into two components; a "standard" (i.e. non-patient specific) cutting block (guide block), which may be made of a biocompatible metal, is attached to a "customized" locating means (which may be a block), thus forming a unitary template. The customized component is designed so as to locate in the unique position for the bone cuts and holes to be made. By making the cutting (guide) block from a biocompatible metal the problem of shedding of potentially harmful particulate matter that is associated with DuraForm does not arise. Stainless steel may be used to manufacture the cutting block and is also robust enough so as to allow the use of the metallic component repeatedly. The locating means (which in certain examples may be described as orientating blocks) can be manufactured with rapid prototyping technologies and are intended for single use. This approach not only avoids the problems associated with the porosity of structures manufactured using rapid prototyping but is more cost effective. The optimal position of the prosthesis is determined precisely during the preoperative planning procedure. The preoperative position of the prosthesis determines the positing of the device relative to the patient's anatomy. Thus the operative procedure is less complex and may be achieved in a shorter time. Embodiments of the invention do not need, and so do not include, adjustable mechanisms, and so are less complex to manufacture, are user friendly and more cost effective. Locators with a relatively small cross sectional area may be used, located upon the tibial plateau with certain tibial device. However, the small cross-sectional area of these cylinders reduces the errors. Certain minimally invasive tibial devices embodying the invention avoid the articular surface of the tibia altogether. The separate components of certain femoral and tibial devices embodying the invention are securely fastened by means of a screw so as to form a single unitary device which will not vibrate apart during use. Convergent pins securely fasten the relevant device to the appropriate bone. Care can be taken during the preoperative planning procedure to place the locators perpendicular to the bone surface. In doing so any possible collisions with the saw blade/drill/adjacent pins are identified and rectified when it is appropriate to do so. In embodiments of the invention, the custom locating means does not sit between the guide block apertures and the bone, so it is possible to design the cutting to be of the required depth to ensure accurate cutting of the bone whilst keeping the overall size of the cutting blocks small. Template systems embodying the invention are designed to be fitted with both ease and accuracy in a unique position on the appropriate bone. The positioning of each template system can be tested in the laboratory, before surgery, e.g. virtually tested during the pro-operative planning procedure. Certain embodiments are designed specifically to increase the visibility the surgeon has of the knee whilst performing the bone cuts. This will not only increase the appeal of each device to the surgeon but also the safety of its use.

BRIEF DESCRIPTION OF THE DRAWINGS

Embodiments of the invention will now be described, by way of example only, with reference to the accompanying figures, of which:

FIGS. 1a-1f are views of a surgical template system for use in working on a femur;

FIGS. 2a-2e are views of the surgical template system from FIG. 1 in use in a surgical method embodying the invention;

FIGS. 3a-3e are views of another surgical template system embodying the invention for use in working on a tibia;

FIGS. 4a-4e are views of the tibial template system of FIG. 3 in use in a surgical method embodying the invention;

FIGS. 5a-5d are views of surgical apparatus embodying the invention (that apparatus including patient-specific locators for use in surgical template systems embodying the invention);

FIGS. 6a-6e are views of part of another surgical template system embodying the invention and for use in working on a femur;

FIGS. 8a-8f are views of further components of the surgical template system including the apparatus of FIG. 6;

FIGS. 9a-9e are views of the apparatus of FIG. 8 in use in a surgical method embodying the invention for preparing a femur to receive a prosthesis;

FIGS. 10a-10d are views of another surgical template system embodying the invention and for use in working on a tibia;

FIGS. 15a-15d are views of another surgical template system embodying the invention and for use on a tibia;

FIG. 17 is a flow chart illustrating steps in a surgical method embodying the present invention;

FIGS. 21a-21e are an end view of a femur end surface, a perspective view of the femur end surface before preparation, a perspective view of a prosthesis, a perspective view of the femur prepared to receive the prosthesis, and a perspective view of the prosthesis fitted to the prepared femur respectively;

FIGS. 23a-23e are views of a bone surface and components of a surgical template system illustrating steps in the design of customised locator elements and methods embodying the present invention;

FIGS. 28a-28d are front, left, top, and isometric views respectively of a template system embodying the invention positioned on a femur;

FIGS. 29a-29d are front, left, top, and isometric views respectively of parts of the template system shown in FIG. 28;

FIGS. 30a-30c are bottom, left, and isometric views respectively of a tool guide block of a template system embodying the invention together with a removable locator;

FIGS. 35a-35c are different views of the locating means of another embodiment of the invention, the locating means incorporating pairs of indicia having separations measurable to check a manufacturing accuracy of the locating means before use in surgery.

DETAILED DESCRIPTION OF THE PREFERRED EMBODIMENTS

Figure 7A:
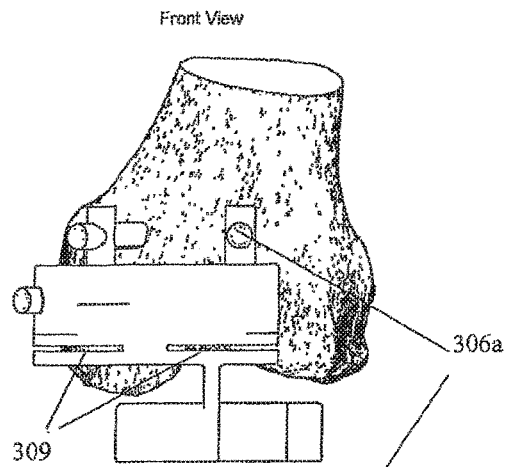
FIGS. 7a-7e are views of the apparatus of FIG. 6 in use in a surgical method embodying the invention to prepare a femur for receiving a prosthesis.
Figure 7B:
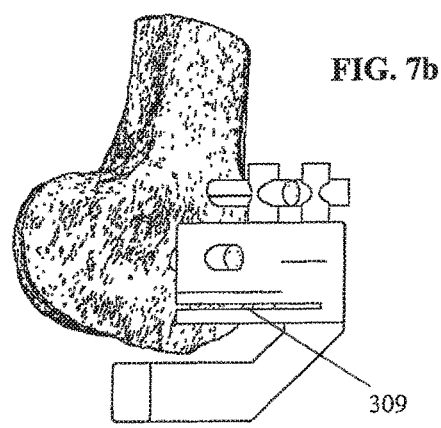
Figure 7C:
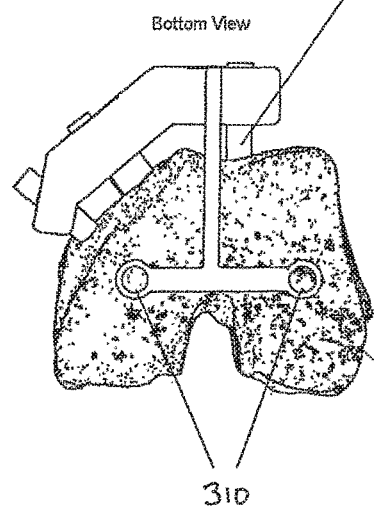
Figure 7D:
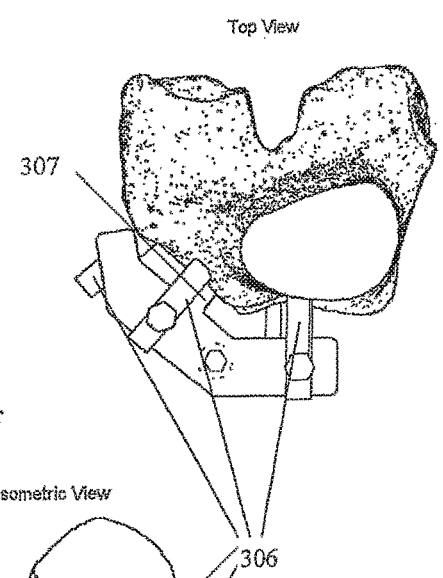
Figure 7E:
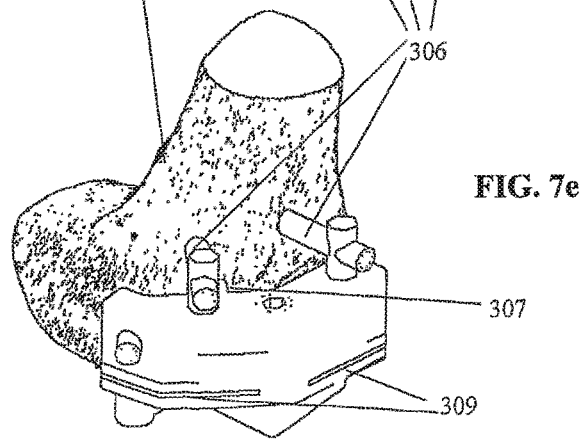

Certain embodiments of the invention may be used in the field of total knee replacement (TKR) surgery. In one example of TKR surgery, two different assemblies each embodying the invention are used, one for use with the femur the other with the tibia, to aid the surgeon in cutting both of these bones to receive prosthetic knee components.

Each assembly comprises a patient specific orienting, block (locating means) and a cutting block (tool guide block), the latter having the appropriate number of slits and holes for guiding moving surgical tools to make the cuts in the relevant bone accurately and in the correct orientation so as to receive the relevant prosthetic component in the position that has been determined through the preoperative planning procedure. Prior to being used in surgery, the orienting and cutting blocks for each bone are assembled and firmly attached with screws to form rigid unitary guides that locate each in a unique position onto the relevant bone and is firmly pinned to the bone at a number of sites on the bone to maintain that position during the process of bone cutting. The sites where the pins engage the bone are carefully chosen such that they avoid the paths of the saw blade when making the bone cuts.

Detailed views of the femoral and tibial assemblies are provided in FIGS. 1-5. FIG. 1 illustrates exploded views of the femoral device from the front, top, bottom, and side, along with an isometric view. FIG. 2 illustrates views of the same device assembled and pinned to the femur. FIG. 3 illustrates exploded views of the tibial device from the front, top, bottom, and sides, along with an isometric view. FIG. 4 illustrates views of the same device assembled and pinned to the tibia. FIG. 5 illustrates front, side, top and isometric views of the customised components immediately after manufacturing, and the figures shows these components kept together as a group, with an additional thin elongate rod that is attached at both ends to a plate containing a unique identification string of alphanumeric characters for each patient. Each component within the group will have inscribed on it means of identification as belonging to this group.

Referring to the labelled views in FIGS. 1 & 2, the customised orienting component 1, is located into a protrusion 24 in the reusable metallic cutting block 2 and firmly attached to it with two screws 3. Countersunk holes 4 on the upper surface of the orientating component align precisely with screw threads 5 in the reusable metallic cutting block.

Although the customised component 1 is currently constructed from DuraForm (PA) it is envisaged that it may be constructed from any of a number of materials that will become available over time. The customised component includes four locators 6 all of which are intended to simultaneously contact the bone of the particular patient, and sit on it in a unique position, thus orienting the cutting block in the appropriate position that has been determined in the preoperative planning stage so as to achieve with precision the appropriate bone cuts and alignment of the prosthetic component within the bone.

The orienting block is firmly attached to the relevant bone with pins 7 through the locators 6. These are positioned during the preoperative planning so as to be perpendicular to the bone surface they are in contact with. This ensures the pins 7 do not skid as they are driven through the bone surface thus firmly securing the orienting block in place while the bone is being cut with oscillating saw blades that are guided by the slits 12 in the cutting block.

A removable locator 8 fits onto a protrusion 9 in the orienting block and is held in place by a square metal peg 10. This removable locator is designed so as to come into contact with a non-articular anterior surface (i.e. the cortical bone surface just above the trochlea) of the femur and in doing so insures that the anterior cortex of the femur will not be violated when making the anterior, since that locator's length is adjusted (during the preoperative planning procedure) so that its tip falls posterior to the slit in the cutting block through which the anterior cut of the femoral bone is made. The removable locator 8 has a hole 11 close to its top surface. This allows it to be grouped with all of the customized components for a given patient during their manufacture (see FIG. 5).

The removable locator 8 has to be removed once the saw blade has advanced sufficiently into the bone when making the anterior cut in order to complete that cut.

The bone cuts are accurately made by passing the saw blade through slits 12. These slits are aligned with precision to the internal surfaces of the relevant femoral prosthesis.

Besides slits for making the bone cuts, the metallic cutting block 2 has two holes 13 to guide a drill bit for making holes into both the medial and the lateral condyles of the femur to receive the fixation lugs of the prosthesis.

Components of the template system thus include: custom component 1; Standard metallic component 2; Protrusion 24; Metallic screws 3; Countersunk holes in custom component 4.

Screw threads 5; Pins 7; Locators 6; Removable locator 8; Protrusion 9 to receive locator 8; Square metal peg 10 to hold 8 to 9; Hole 11 in removable locator; Slits 12 to guide saw bade; and Holes 13 to guide drill.

Thus, from the above description of FIGS. 1 and 2, it will be appreciated that a first surgical template system embodying the present invention comprises a tool guide block 2 comprising a plurality of guide apertures 200 for receiving and guiding the tool or tools to work on a bone. The system further comprises locating means 1 comprising a plurality of locating members in the form of locating fingers 6, each finger having a respective end surface 61 for positioning against a surface of the bone. The template system also includes attachment means 3 for releasably and non-adjustably attaching the tool guide block 2 to the locating means 1. In other words, the securing means 3 secures the locating means 1 and tool guide block 2 when they are assembled together. When the locating means 1 and tool guide block 2 are attached together by the attachment means 3 the finger end surfaces 61 are secured in fixed position with respect to each other, for engaging different portions of the surface of the bone, and the guide apertures 200 are also secured in fixed position with respect to those locating end surfaces 61. In this first embodiment, the locating means 1 has been manufactured using rapid prototyping technique from plastic material. The manufacturing technique has included the step of determining the shape of a femur to be worked on, and the locating finger end surfaces 61 are adapted to conform to the particular femur surface and enable the assembled template to be seated in a defined, substantially unique position on that particular femur with the guide apertures 200 then positioned so that when cuts and holes are made in the femur the resultant prepared surface conforms to the interior surface of a prosthesis.

In this first example, the locating means 1 comprises a body portion 60 and the four fixed locating fingers 6 extend from that body 60 to their bone-engaging end surfaces 61. In fact, in this example the locating fingers 6 and body 60 are integral. Thus, as the fingers 6 and body 60 are substantially rigid, the positions of the end surfaces 61 are in a defined, fixed relationship to one another even before the attachment means secures the guide block 2 to the locating means 1. However, it will be appreciated that in alternative embodiments, at least some of the locating fingers 6 may be separate from one another, such that their end surfaces 61 are only in fixed positions with respect to each other when these separate locators 6 have been secured to the guide block 2.

Each of the four rigid locating fingers 6 is substantially cylindrical and elongate, and includes a bore extending through the finger 6 to its end surface 61. The template system further comprises a plurality of pins 7, each pin being arranged so as to extend through the bore of a respective locating finger 6 so that it can be driven into the bone surface against which a template system is positioned to secure the template system to the bone to be worked on. The orientation of the bores has been determined during the template system manufacturing method so that each bore is substantially perpendicular to the portion of the bone surface against which its respective locator end surface 61 is seated. This helps to ensure that when the pins are driven into the bone they do not skid. An advantage of securing the locating means to the bone in this way is that the tool guide block of the system is then rigidly and securely held in place, and will not become unseated even when cutting operations using saws and or drills are being used on the bone.

The locating means 1 and tool guide block 2 in this example are adapted to key together by means of a block-like protrusion 24 on the guide block 2 and a corresponding recess 624 in the body 60 of the locating means. The attachment means takes the form of two machine screws or bolts which pass through countersunk holes 4 in the locator body 60 and which are then received in a pair of threaded holes 5 in the tool guide block 2. The machine screws 3 thus releasably and non-adjustably attach the tool guide block 2 to the locating means 1.

In addition to the four fixed locating fingers 6, the locating means comprises an additional, removable locating member 8 having an end surface 81 for engaging another portion of the femur surface when the template system is in the defined position. In this example, the removable locator end surface 81 is adapted to sit on an anterior non-articular surface of the femur. The removable locator 8 is removably mounted on a mount or protrusion 9 extending from the locator body 60 and is secured in place by means of a square peg 10. The protrusion 9 is received in a corresponding slot on the removable locator 8, and the square peg 10 then passes through an end surface of the removable locator 8 to effectively pin it to the portion of the protrusion 9 received in the slot of the locator 8. The removable locator 8 also has a hole or bore 11 by means of which it can be linked to the other patient-specific components during manufacture.

It will be appreciated from the above that, as the locating members (fingers or cylinders) 6 are provided with bores 62 (in other words they are cannulated for driving pins 7 through them) their end surfaces 61, which are adapted to conform to respective portions of the predetermined femur, are annular.

Turning now to the details of the guide block 2 in this first example the guide block 2 is metallic. It comprises a first portion 21 which comprises a guide aperture in the form of a slot 201 for receiving and guiding a reciprocating saw blade to perform a cutting operation on the femur against which the template is positioned and secured. This first portion 21 is the portion of the guide block 2 to which the attachment means 3 attaches the locating means 1. The guide block 2 comprises a second portion 22 which comprises a plurality of guide slots 12 and a plurality of guide holes 13. The guide slot 201 in the first portion 21 enables a saw blade to be guided and used to cut a flat surface on the end of a femur, substantially from a side direction relative to the longitudinal axis of the bone. The guide slots and holes 12, 13 provided in the second portion 22 of the block then enable guided holes to be drilled in the sawn end femur surface and for the end of the femur to be further shaped. The guide slots intersecting the guide holes 13 are inclined with respect to each other and the other two slots in the second portion 22 of the guide block are substantially parallel to one another. The first portion 21 and second portion 22 of the guide block are rigidly connected together by a connecting portion 23 which in this example is in the form of a relatively thin web 23. The first, second and connecting portions 21, 22, 23 have in fact been formed by suitable machining of a single metallic block. The connecting portion 23 can be made so thin, i.e. having a thickness substantially smaller than the lengths of the guide slots 12 (e.g. between 2-20 mm, 3-12 mm, or even 4-6 mm thick), and yet hold the first and second portions 21, 22 securely and rigidly together as a result of being formed from a metal, and it will be appreciated that this enables the template system as a whole to provide improved visibility of the bone being worked on to the surgeon. In other words, as a strong, rigid material can be used for the guide block 21, the connecting portion 23 can be small, and hence obscures only a small part of the bone being worked on.

The locating means body 60 and integral locating fingers 6 in FIGS. 1 and 2 may also be described as a customised orienting component, in that it has been manufactured so as to be patient specific. In contrast, the guide block 2 is not patient specific. Its array of guide apertures 200 (i.e. slots 12 and holes 13) are in a predetermined relationship with respect to each other and are not influenced by the geometry of a specific patient's bone. Instead, they are arranged so that when used to prepare the surface of a femur, the prepared surface then conforms to the interior surface of a predetermined prosthesis.

The method by which the template system of FIG. 1 has been manufactured, in addition to taking into account the specific bone shape to determine the locations, and indeed shapes, of the locator end surfaces 61, 81, has also been arranged to ensure that the positions and orientations of the guide slots 12 and holes 13 are such that tools guided by them avoid the locator body 60, the fixed locators 6 extending from it and the pins 7. The removable locator 8 and in particular its tip with end surface 81, is, however, in the line of a cut made by the saw guided by slot 121. Thus, in use, the removable locator 8 is secured to the locator body 60 during the step of positioning the assembled template system on the femur and remains there until the pins 7 have been driven into the bone to secure the template. The removable locator 8 is then detached and removed from the locator body 60 before the cut guided by slot 121 is made. In this way, cutting of locating means material is avoided.

In certain embodiments, plastic material is used to manufacture the locating means 1 comprising cannulated locators 6. Suitably sized metallic pins 7 may then be received directly in the bores of those cannulated members 6, i.e. with the pin surface in direct contact with the plastic interior surface of the bore 62. However, in alternative embodiments cylindrical sleeves of relatively hard material (e.g. metal) may be provided in these bores 62, with the pins 7 then being received inside the sleeves. This can further help prevent contamination of a surgical site with particles of the locating means material, as all locating means surfaces are kept away from any moving component (pin or tool).

In the embodiment shown in FIG. 1 it will be appreciated that the first portion 21 of the cutting block 2 is generally curved, and the connecting web 23 extends generally from a midpoint of the first portion 21 to the midpoint of an end surface of the second portion 22 of the block 2. In other embodiments, however, the web may be connected at a different position with respect to the first portion, i.e. not necessarily at a midpoint. Looking at FIG. 2, FIG. 2a shows the template system from FIG. 1 assembled, and arranged in the predetermined, defined position with respect to the surface of the patient's femur. Positioning the template against the femur in this way is part of the process of preparing the bone to receive a selected prosthesis. The extent would be to drive pins 7 into the bone surface through the bores 62 to secure the template in the illustrated position. Then, a lateral cut would be made by inserting a reciprocating saw blade in the guide slot 201 to remove an end portion of the femur. The removable locator 8 could then be detached, and further cuts would then be made using the guide slot 12 in the second portion 22 of the block 2 and holes would be drilled through guide holes 13.

Although the first portion 21 of the cutting block 2 in FIG. 1 has just one guide slot 210, in alternative embodiments a plurality of adjacent parallel slots may be provided (e.g. two or more, separated by relatively small distances, such as 0.5-2 mm). These can give the surgeon a choice and provide some flexibility during surgery as to the position of a cut. The surgeon can thus adapt to circumstances revealed only after surgery has begun. The plurality of slots may, of course, be provided elsewhere on the template block; they are not necessarily on a first portion.

Referring now to the labelled views of the tibial system in FIGS. 3 & 4, the customised orienting component 101, is located into the top of standard cutting block 102 from its underside and firmly attached to it with a metallic screw 103. Countersunk holes 104 on the under surface of the orientating component 101 align precisely with the screw threads 105 in the standard cutting block. The customised component 101 has two locators 106 both of which simultaneously contact the tibial plateau of the particular patient, and sit on it in a unique position, thus (along with the locators 107 orienting the reusable metallic cutting block in the appropriate position that has been determined in the preoperative planning stage so as to achieve with precision the appropriate bone cuts and alignment of the prosthetic component within the bone.

Although the custom components 101 and 108 are constructed from DuraForm (PA) it is envisaged that they may be constructed from a number of materials that will become available over time.

The customised orientating component 108 is located into protrusions in the front of the reusable metallic component 102 and firmly attached to it with a metallic screw 109.

Countersunk holes 110 on the back surface of the orientating component 108 align precisely with the screw threads 111 in the reusable metallic cutting block. The custom component 108 has two locators 107 both of which simultaneously contact an anteromedial region of the tibia of the particular patient, and sit on it in a unique position, thus (along with the locators 106) orienting the cutting block in the appropriate position that has been determined in the preoperative planning stage so as to achieve with precision the appropriate bone cuts and alignment of the prosthetic component within the bone.

The orienting blocks are firmly attached to the relevant bone with pins through locators 106 and 107. These are positioned during the preoperative planning so as to be perpendicular to the bone surface they are in contact with. This ensures the pins do not skid as they are driven through the bone surface thus firmly securing the orienting block in place while the bone is being cut The 'tibial' bone cut is accurately made by passing the saw blade through the slit 112 on the cutting block 102. This slit is aligned with precision to the internal surfaces of the relevant tibial prosthesis.

The reusable metallic cutting block 102 has a hole 113 aligned with the axis of the tibial component fixation stem and serves to guide with precision a drill bit through the tibial plateau. Slits 114 in the shape of a 'T' which are aligned to the keels of the relevant tibial prosthesis guide the passage of a saw blade into the tibial plateau with precision. The resulting hole and cuts in the bone receive the lug and keel of the prosthesis. For prostheses with different internal surface formations, the guide apertures in the cutting block are of course adapted to facilitate cutting/drilling of an appropriate "receiving" structure on the bone.

Components of the tibial system thus include: Custom component 101; Standard metallic component 102; Metallic screw 103 to fix 101 to 102; Counter sunk hole 104 in custom component 101; Screw thread 105 in 102; Locators 106 associated with 101; Locators 107 associated with 108; Custom component 108; Metallic screw 109 to fix 108 to 102; Counter sunk hole 110 in custom component 108; Screw thread 111 in 102; Slit 112 to guide saw blade; Hole 113 to guide drill; and Slits 114 to guide saw blade.

From the above description of FIGS. 3 and 4, it will be appreciated that these show another surgical template system embodying the invention and its use in a surgical method to prepare a tibia to receive a prosthesis. The template system of FIGS. 3 and 4 can thus be used in conjunction with template system of FIGS. 1 and 2 in total knee replacement surgery. It will be appreciated, however, that although the system of FIGS. 1 and 2 was described in connection with work on a femur and the system of FIGS. 3 and 4 will be described with reference to work on a tibia, the features of the described systems may also be employed in template systems for working on other bones.

Returning to FIGS. 3 and 4, in the illustrated embodiment the template system again comprises a metal tool guide block 102 which is steralisable and reusable and is not patient-specific. This metal guide block (which may also be referred to as a standard cutting block) comprises a first portion 1021, which provides a saw guide slot 112, and a second portion 1022 which provides a guide aperture comprising both a guide hole portion 113 and guide slots 114. A connecting portion 1023 in the form of a rigid arm or web of uniform thickness connects' the first and second portions 1021, 1022. The first portion 1021 extends around an arc and in this example is curved (i.e. is generally arcuate), providing the guide slot 112 within which an oscillating saw blade can be moved through a defined arc to produce a cut on the bone (in this case a tibia) being worked on. The connecting arm 1023 is connected to one end of the generally arcuate first portion 1021. As can be seen from the figures, this arrangement provides the advantage that it gives improved visibility of the bone surface being worked on and by reducing the overall size of the guide block 102 makes the system particularly suited for minimally invasive surgery, in that it can be inserted and positioned on the bone surface through a smaller incision and would be necessary if the first portion of the guide block extended also from the other side of the connecting arm or web 1023. Plus, in contrast to the guide block 2 of the system from FIGS. 1 and 2 which was generally symmetrical about a plane through the connecting web 23, the guide block 102 of this second template system is asymmetric.

In the example shown in FIGS. 3 and 4, the locating means comprises a first component 101 (which may be described as a first customised orienting component) and a second component 108 (which may be described as a second customised orientating component). The first orienting component 101 comprises a first body portion 1060 and two integral locators 106 (in this example generally cylindrical locating fingers). These locators 106 extend from the body portion 1060 to their respective end surfaces 1061. These locators 106 are again cannulated, having respective bores 62 to receive securing pins. The first component 101 has been produced by a method involving determining a shape of part of the articular surface of tibia, and using the determined shape to determine the positions and shapes of the end surfaces 1061 of the locators 106 such that they help seat the assembled template system on the specific tibia in a well defined position. The second portion of the guide block 1022 is adapted to receive the body portion 1060 of the first component 101 from below, such that the guide block then prevents any further upwards movement of the component 101. When assembled in this manner, a screw or bolt 103 is inserted through a hole 104 in the first component 101 and is received in a threaded hole 1030 in the second portion of 1022 of the guide block 102. This screw 103 is then tightened to releasably and non-adjustably attach the first component 101 to the guide block so that its locating surfaces 1061 are in fixed position with respect to the plurality of tool guiding apertures.

Similarly, the second customised locating component 108 comprises a body portion 1060 from which two locating fingers 107 extend to their respective bone-engaging surfaces 1071. Again, this second locating component 101 has been produced by a method involving determination of a shape of the tibia surface and rapid prototyping to produce the component 108 such that the end surfaces 1071 conform to and are seated on non-articular portions of the tibia surface when the template system is in the desired, defined position. The second component 108 is adapted to slot into the nominal base of the first portion 1021 of the cutting block and is then secured and attached in this assembled position by means of another screw or bolt 109 passing through a hole 110 into a threaded hole 111 in the first portion 1021 of the guide block 102.

Referring in particular to FIG. 4, these views show the assembled template system of FIG. 3 arranged in the predetermined, defined (and substantially unique) position on a tibia, with the locators 106 engaging portions of the articular surface of the tibia, and the end surfaces 1071 of the other locators 107 engaging portions of the non-articular surface of the tibia. As can be seen from the figures, the first portion 1021 of the cutting block extends around less than a quarter of the circumference of the tibia when looking generally along the longitudinal axis of the tibia, and in FIG. 4c). However, the curved guide slot 112 it provides enables a saw blade guided by that slot to reach the entire tibia surface. Plus, the arrangement is particularly suited to minimally invasive techniques. Although not shown in FIG. 4, with the template arranged in the shown position, pins will then be driven through the bores 62 to secure the assembled template system to the bone. The slot 112 can then be used to guide a saw blade to produce a cut across the end of the tibia. The composite guide aperture (comprising guide hole 113 and slot 114) in the second portion of 1022 of the guide block can also be used to cut a correspondingly shaped recess in the end surface of the tibia to receive a correspondingly shaped formation (which may also be referred to as a keel) on an underside of a tibial prosthesis for fitting to the prepared bone.

Again, the two-part locating means 101, 108 of the template system in FIGS. 3 and 4 has been manufactured according to a determined shape of the bone to be worked on and such that the locating means is avoided by tools guided by the plurality of guide apertures in the reusable guide block 102. By doing this, small particles of locating means material are not produced when working on the bone and hence contamination of the surgical site by such particles is also avoided.

Referring now to FIG. 5, this shows views of surgical apparatus in accordance with another aspect of the present invention. As mentioned above, the two template systems of FIGS. 1-4 can be used in total knee replacement surgery for fitting prostheses to both the femur and tibia. Those template systems comprise reusable metal cutting blocks and a plurality of patient-specific custom-made components forming the locating means. The apparatus of FIG. 5 comprises the plurality of components of the custom-made locating means for the femoral and tibial template systems corresponding to a particular patient's knee joint, together with patient identification means, providing an indication of the particular patient to whom the knee belongs, and linking means linking the locating means to the patient identification means.

In this example the linking means is in the form of a rod 201, which passes through holes in each of the individual components of the locating means of the femoral and tibial template systems and connecting them to an identification plate 202 which carries information 2020 identifying the patient. Both ends of the rod 201 are connected to the plate 202 so that the locating means components cannot become separated from it. As further security, the plate 202 carries a unique identifier 9 and each component of the locating means also carry this identifier. Thus, the surgical apparatus, which can also be regarded as a pack of patient-specific components, can be provided to the surgeon. A linking means (rod 201) can then be broken or cut to separate the locator components, which can then be assembled together with the sterilised, reusable cutting blocks.

Thus, FIG. 5 shows surgical apparatus embodying the invention and comprising customised components, immediately after manufacturing. The customised orientating components 1, 8, 101 and 108 have been manufactured with rapid prototyping technology, threaded together as a group, with an additional thin elongate rod 201 that is attached at both of its ends to a plate 202 containing a unique identification string of alphanumeric characters for each patient. Each component within the group will have inscribed on it means of identification as belonging to this group. This mode of manufacturing is adopted to prevent mixing components manufactured for different patients. The apparatus (which can be described as a custom part holder) thus includes: Custom femoral part 1; Custom removable locator 8 for femoral part; Unique code 9 which corresponds exactly to the code given by 202; 101 Custom tibial part for tibial plateau; Custom tibial part 108 for anteromedial tibia; Elongated rod 201; and plate 202 carrying unique identification string of alphanumeric characters for each patient Certain embodiments of the invention are modified so as to facilitate achieving bone cuts in TKR surgery that adopts a minimally invasive (MI) approach. In this approach it is aimed to perform the bone cuts and implantation procedure through the smallest possible incision into the joint. This reduces the trauma to the surrounding tissues, and speeds up the recovery of the patient.

In certain examples of MI surgery two different template systems embodying the invention are used, one for use with the femur the other with the tibia, to aid the surgeon in cutting the knee bone. Each assembly comprises a patient specific orienting block(s) and two separate cutting blocks with the appropriate number of slits and holes guiding moving surgical tools to make the cuts in the relevant bone accurately and correctly oriented so as to receive the relevant prosthetic component in the position determined by the preoperative planning procedure. The orienting and cutting blocks are assembled and firmly attached with screws to form a rigid unitary guide that locates in a unique position onto the relevant bone and is pinned to the bone at a number of carefully chosen sites on the bone such that the pins avoid the path of the saw blade used for making the bone cuts. Using the results of the first cutting block a second cutting block is then guided into position and the preparation of each bone completed so as to receive the relevant prosthetic component.

Detailed views of the minimally invasive femoral and tibial assemblies embodying the invention are given in FIGS. 6-9.

FIG. 6 illustrates exploded views of Part A of the femoral device from the front, top, bottom, and side, along with an isometric view. FIG. 7 illustrates views of the same device assembled and pinned to the femur. FIG. 8 illustrates exploded views of Part B of the femoral device from the front, top, bottom, along with an isometric view. FIG. 9 illustrates views of the same device pinned to the femur after the distal cut has been made.

Referring to the labelled views of the MI femoral system in FIGS. 6 & 7, the customised orienting component 301, is located into a protrusion in the reusable metallic cutting block 302 and firmly attaches to it with a metallic screw 303. Countersunk holes 304 on the upper surface of the orientating component align precisely with screw threads 305 in the standard cutting block.

Although the custom component 301 is constructed from DuraForm (PA) it is envisaged that it may be constructed from a number of materials that will become available over time. The customised component includes three locators 306 all of which simultaneously contact the bone of the particular patient, and sit on it in a unique position, thus orienting the cutting block in the appropriate position that has been determined in the preoperative planning stage so as to achieve with precision the appropriate bone cuts and alignment of the prosthetic component within the bone. In addition to the three locators the customised component also has a protrusion 307 which also sits on the bone of the particular patient in a unique position, thus also assisting in the orientation of the cutting block. It may be appropriate to vary the size of this protrusion. An alternate approach is this protrusion as a guide, which, although close to the bone surface of the particular patient it will not come into contact with it.

The orienting block is firmly attached to the relevant bone with pins 308 through locators 306. These are positioned during the preoperative planning so as to be perpendicular to the bone surface they are in contact with. This ensures the pins 308 do not skid as they are driven through the bone surface thus firmly securing the orienting block in place while the bone is being cut. The locator 306a sits in the trochlea of the femur and so acts as an additional reference with regard to placement of the device.

The distal bone cut is accurately made by passing the saw blade through slit 309. This slit is aligned with precision to the internal distal surface of the relevant femoral prosthesis. The size of both the slit 309 and the standard cutting block. 302 is determined prior to manufacturing based upon the thickness of saw blade to be used and the permitted deviation of the saw blade in the slit 309. The standard cutting block 302 has two holes 310 to guide a drill bit into both the medial and the lateral condyles of the femur. The resulting holes in the bone ultimately receive the fixation lugs of the prosthesis.

The resulting flat bone surface created by performing the distal cut along with the holes in the medial and lateral condyle are also used to locate Part B of the femoral device.

Referring now to part B of the MI femoral template system, the lugs 311 are located in the drilled holes in the medial and lateral condyles and the flat surface 312 of the cutting block 313 placed precisely onto the cut flat surface created by performing the distal cut. The flat surface 312 is aligned with precision to the internal distal surface of the relevant femoral prosthesis. The cutting block 313 is securely fastened to the flat bone surface by pins 314. These pins pass through lugs 315 which each have a hole of precise dimensions to guide the pin into the bone whilst avoiding both the lugs 311 and the saw blade.

In order to prevent the pins 314 from loosening by vibration during the bone cutting procedure a means of locking the pins into lugs 315 is provided. Such means (not shown) would by the way of example be a spring washer to be fitted in a groove in the pin 314 which would come into view, once the pin has been driven into the bone, at the side of the lug 315 nearer to the bone.

The four slits 319 are aligned with precision to the remaining four internal surfaces of the relevant femoral prosthesis. The size of both the slits 319 and the standard cutting block 313 is determined prior to manufacturing based upon the thickness of saw blade to be used and the permitted deviation of the saw blade in the slits 319.

From the above description of FIGS. 6-9 it will be appreciated that the illustrated surgical template system comprises a first tool guide block, patient-specific locating means 301, attachment means 303 for releasably and non-adjustably attaching the locating means 301 to the tool guide block 302, and a second tool guide block 313 having a flat surface 312 adapted to sit on a bone flat surface prepared using the first tool guide block 302. The first tool guide block 302 again comprises a first portion 3021 to which the locating means 301 is securely fastened (i.e. clamped) by the attachment bolt 303. This locating means 301 again comprises a body portion 3060 and three integrally formed locating fingers 306. In addition, the locating means includes an additional integral locator 307 in the form of a protrusion extending from the body 3060. The three locating fingers 306 are cannulated, whereas the additional locating protrusion 307 is solid. The locating means 301 is arranged to key with the guide block 302 and to this end the locating means body 3060 is provided with a pair of slots or mortises 3065 adapted to receive correspondingly shaped tongues or tenons 3056 on the first portion 3021 of the guide block. This first portion 3021 of the guide block provides a tool guiding slot 309 which is open at both ends of the first portion 3021. This facilitates insertion of a-saw blade into the slot. Furthermore, by not requiring material to close the slot at both ends, it enables the size of this first portion 3021 to be made smaller than would otherwise be the case and so makes the template system more suitable for minimally evasive surgery. The first guide block 302 again comprises a connecting portion 3023 in the form of a web or connecting arm, connecting the first portion 3021 to the second portion 3022 which in this example comprises a pair of guide holes 310. Again, the first guide block 302 is asymmetrical, with the connecting web 3023 being connected to the first portion 3021 towards one end of the open ended guide slot 309. In use, the assembled first guide block 302 and customised locator component 301 are positioned against the femur as shown in FIG. 7, and pins 308 are driven through the bores 62 in the cylindrical locators 306 to attach the template to the bone. The saw blade is then inserted in guide slot 309 and appropriately manipulated to cut a flat end surface of the femur. Then, guide holes 310 are used to guide a drill to drill two locating holes in the sawn end surface of the femur. The assembly is then detached from the femur and the second guide block 313 is then positioned on the sawn femur surface, with its flat surface 312 in contact with the sawn surface of the bone and with locating protrusions 311 located in the locating holes previously drilled using guide apertures 310. The second guide block 313 is then secured in place and the guide slots 319 are used to guide the saw blade to perform further work on the femur.

It will be appreciated that the first and second guide blocks 302 and 313 of the template system showing FIGS. 6-9 are individually smaller than a guide block that would be required if that guide block were to provide all of the guide apertures to prepare the femur surface in the manner shown. Thus, by effectively splitting the guide block into two, with each component being relatively small, the template system of FIG. 6-9 is particularly suited for minimally invasive surgery.

A minimally invasive two-part tibial template system embodying the invention will now be described. Referring to the labelled views in FIGS. 10 & 11, the customised orientating block 401 is located onto the standard cutting block 402 with protrusions in the latter. Metallic screws pass through countersunk holes 403 on the upper surface of the orientating component 401 and fasten with precisely aligned screw threads 404 in the standard cutting block 402.

The customised orientating component 405 is located into the front of the standard component 402 with protrusions in the latter and firmly attached to it with a metallic screw. Countersunk holes on the back surface of the orientating component align precisely with the screw threads in the standard cutting block. In doing so the customised orientating blocks and the standard cutting block are firmly fixed together.

The customized orientating block 401 has protrusions 406 and the customized orientating block 405 has locating cylinders 407 all of which simultaneously contact the bone of the particular patient and sit on it in a unique position thus orientating the cutting block in the appropriate position which is determined during the preoperative planning stage so as to achieve with precision the appropriate bone cuts and alignment of the appropriate prosthesis within the bone.

The orienting block is firmly attached to the relevant bone (see FIG. 11) with pins 408 through locators 407. These are positioned during the preoperative planning so as to be perpendicular to the bone surface they are in contact with. This ensures the pins 408 do not skid as they are driven through the bone surface thus firmly securing the orienting block in place while the bone is being cut. Attention is paid to the position of the pins relative to one another during the preoperative planning procedure to ensure they do not collide with one another when driven into the bone. The tibial bone cut is made by passing a saw blade through slit 409. This slit can be open at either end so as to allow greater movement of the saw blade whilst making the tibial cut.

With regard to the second part (part B), referring to the labelled views in FIGS. 10 & 12, after making the tibial cut the waste bone is removed and the standard cutting block 410 is positioned onto the cut bone surface 411. This cutting block has an arm 412 with a rectangular section 413 of precise dimensions removed from it. This allows the cutting block 410 to be guided into the position determined during the preoperative planning procedure by the rectangular post 414 which has precise dimensions and forms part of the cutting block 402. The cutting block 410 is then pinned to the bone through holes 415. These may be inclined slightly so as to offer a more secure placement of the block 410. It may be necessary to remove one or more of the pins 408 so that tools can be passed through the guide 416 and into the bone unhindered as the tibia is prepared to receive the appropriately sized prosthesis.

Figures 11A, 11B, 11C, 11D:
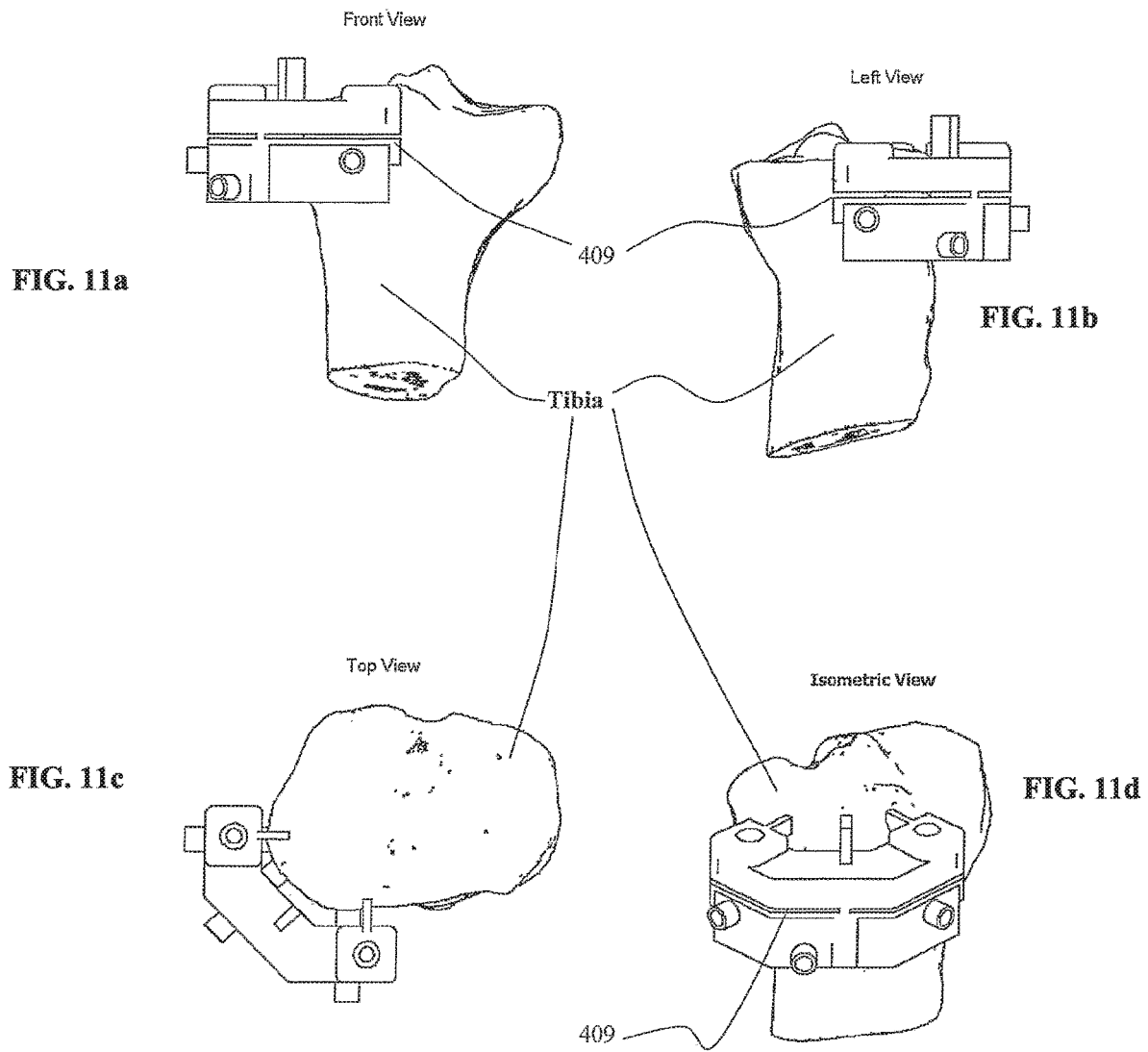
FIGS. 11a-11d are views of the template system from FIG. 10 in use in a method embodying the invention.
Figure 12A:
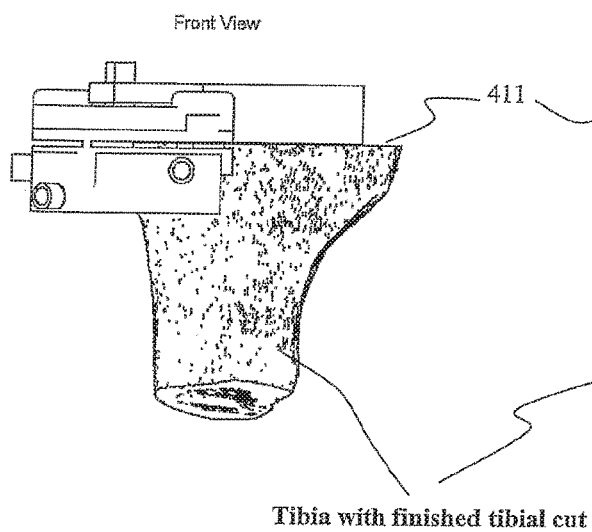
FIGS. 12a-12d are further views of the apparatus from FIG. 10 in use in a tibial preparation method embodying the invention.
Figure 12B:
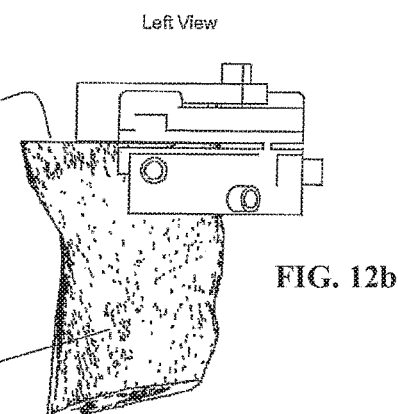
Figure 12C:
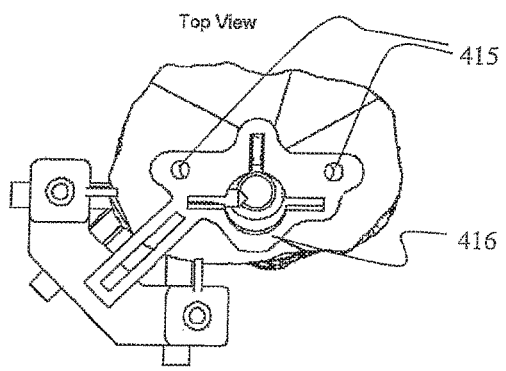
Figure 12D:
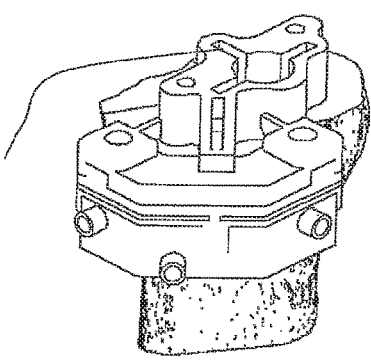
Figures 13A, 13B:
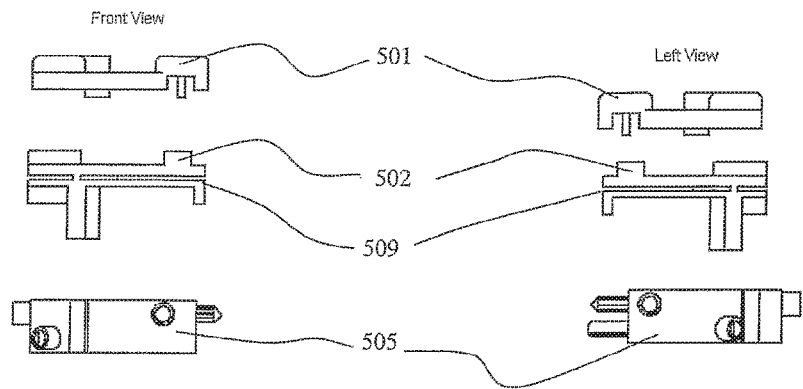
FIGS. 13a-13d are views of another surgical template system embodying the invention and for use in working on a tibia.
Figures 13C, 13D:
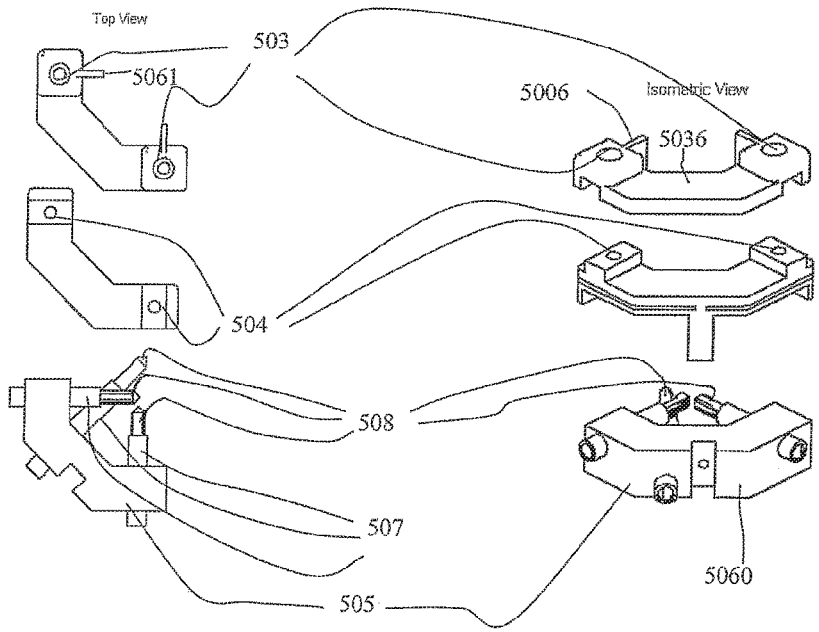
Figure 14A:
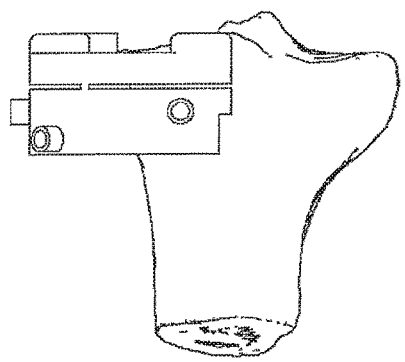
FIGS. 14a-14d are views of the apparatus of FIG. 13 in use in a method embodying the invention.
Figure 14B:
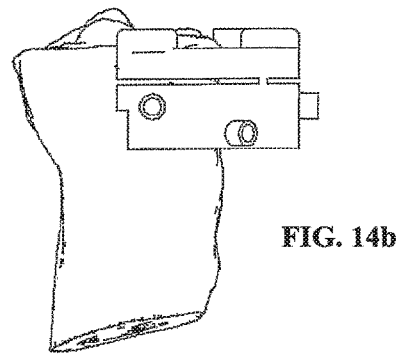
Figure 14C:
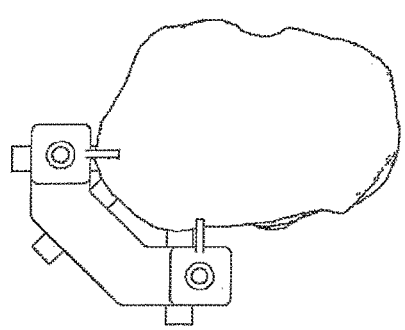
Figure 14D:
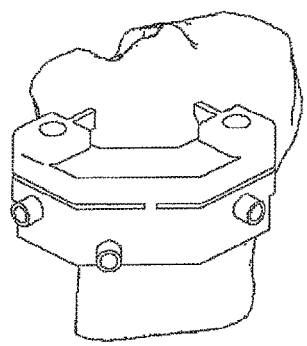
Figure 16A:
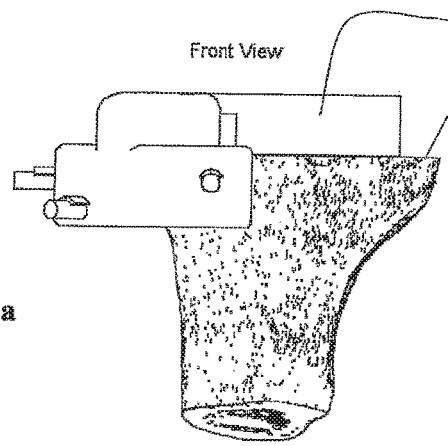
FIGS. 16a-16d are views of the apparatus from FIG. 15 in use in a method embodying the invention.
Figure 16B:
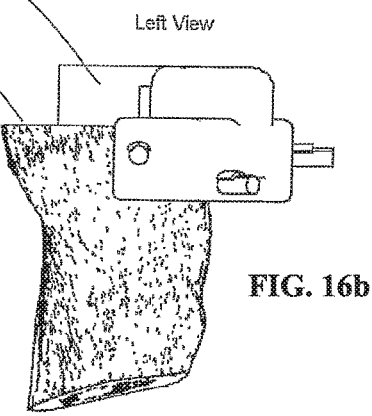
Figure 16C:
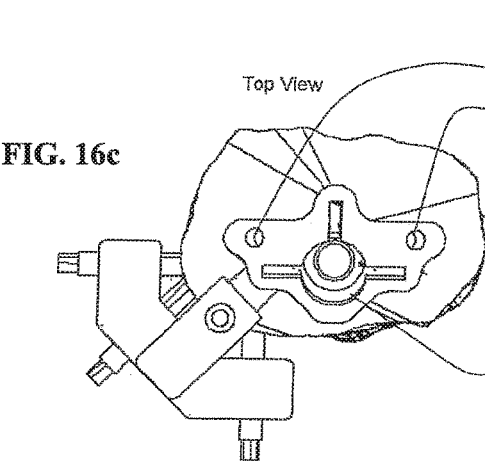
Figure 16D:
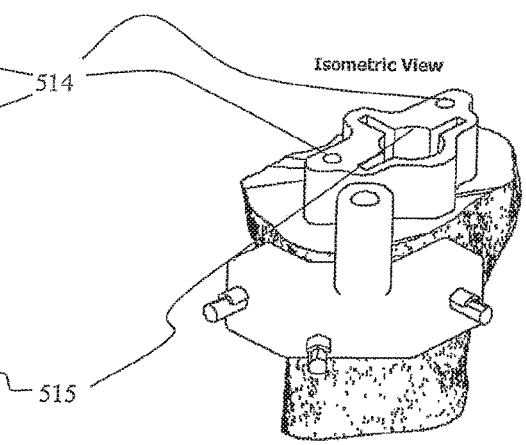

From the above description of FIGS. 10-12 it will be appreciated that the template system again comprises a first tool guide block 402 and a second tool guide block 410. Also, in that system the locating means comprises a first body portion 4060 and a plurality of locating fingers 407 formed integrally with the body portion 4060 and extending from it to respective bone engaging end surfaces 4071. Attachment means in the form of a screw (not shown in the figure) can be used to attach the first body portion 4060 to the first guide block 402. The locating means also comprises an additional body portion 4066. A pair of additional locating members 406 in a form of fifths is integrally formed with the second body portion 4066, and extend from it to their respective end surfaces 4061 which have been manufactured to conform with and engage respective portions of the surface of a bone to be worked on. The attachment means comprises additional screws or bolts to attach the additional body portion 4066 to the first guide block 402 by means of holes 403 in the additional body portion and threaded holes in the first guide block 402.

The first guide block 402 comprises mounting means in the form of mounting post 414 for mounting the second guide block 410 on the first guide block 402 after the first guide block and locating means assembly has been used to guide a saw, using guide slot 409 to produce a cut surface on the end of the tibia. When the second guide block 410 has been mounted in place of first guide block the second guide block 410 can be used to guide a drill and then a saw blade using composite guide aperture 113, 114. Again, by employing a template comprising two separate guide blocks, the individual guide blocks can be made smaller than would be the case of a single guide block providing all guide apertures were used, and hence the system is particularly suited to minimally invasive surgery.

Another two-part minimally invasive tibial template system embodying the invention will now be described with reference to FIGS. 13 to 16. Referring to the labelled views in FIGS. 13 & 14, the customised orientating block 501 is located onto the standard cutting block 502 with protrusions in the latter. Metallic screws pass through countersunk holes 503 on the upper surface of the orientating component 501 and fasten through precisely aligned screw threads 504 in the standard cutting block 502. The customized orientating component 505 is located into the front of the standard component 502 with protrusions in the latter and firmly attached to it with a metallic screw. Countersunk holes on the back surface of the orientating component align precisely with the screw threads in the standard cutting block. In doing so the customised orientating blocks and the standard cutting block are firmly fixed together.

The customized orientating block 501 has protrusions 506 and the customized orientating block 505 has locating cylinders 507 all of which simultaneously contact the bone of the particular patient and sit on it in a unique position thus orientating the cutting block in the appropriate position which is determined during the preoperative planning stage so as to achieve with precision the appropriate bone cuts and alignment of the appropriate prosthesis within the bone.

The orienting block is firmly attached to the relevant bone (see FIG. 14) with pins 508 through locators 507. These are positioned during the preoperative planning so as to be perpendicular to the bone surface they are in contact with. This ensures the pins 508 do not skid as they are driven through the bone surface thus firmly securing the orienting block in place while the bone is being cut. Attention is paid to the position of the pins relative to one another during the preoperative planning procedure to ensure they do not collide with one another when driven into the bone. The tibial bone cut is made by passing a saw blade through slit 509. This slit can be open at either end so as to allow greater movement of the saw blade whilst making the tibial cut.

Referring to the labelled views in FIGS. 15 & 16, after making the tibial cut the waste bone is removed, along with Part A of the tibial device. The customized orientating block 509 is located onto the arm 510 of the standard cutting block 511 and may be firmly attached to it by means of a metallic screw. The standard cutting block 511 is positioned onto the cut bone surface 512. Locating cylinders 513 all of which are sectioned along their long axis simultaneously contact the bone of the particular patient and sit on it in a unique position thus orientating the cutting block 511 in the appropriate position which is determined during the preoperative planning stage so as to achieve with precision the appropriate bone cuts and alignment of the appropriate prosthesis within the bone. These sectioned cylinders align precisely with the cylinders 507 from Part A of the tibial device. Thus after removing Part A the pins 508 may be replaced and the sectioned cylinders 513 located upon them so as to increase the accuracy of placement.

The cutting block 511 is then pinned to the bone through holes 514. These may be inclined slightly so as to offer a more secure placement of the block 511. It may be necessary to remove one or more of the pins 508 so that tools can be passed through the guide 515 and into the bone unhindered as the tibia is prepared to receive the appropriately sized prosthesis.

It will be appreciated from the above description of FIGS. 13-16 that the template system comprises a first guide block, providing a single, open ended guide slot 509, and locating means comprising a first body portion 5060 from which a plurality of locating members 507 extend, and a second body portion 5036, from which a further plurality of locating members 5061 extend. The attached assembly of the first guide block 502 and first locating means 501, 505 is positioned on the bone surface, secured in place using pins through the locators 507, and the guide slot 509 is used to guide a saw to produce a cut in the tibia end surface. The assembly is then removed from the tibia. The template system comprises a separate, second tool guide block 511 and a separate, second locating means 509 which comprises an integral body and plurality of locating fingers 513. This second locating means 509 is adapted to receive the second guide block 511 and holds that second guide block in the desired, correct position on the tibial sawn surface when the second locating means 509 is pinned in place.

Manufacturing methods, surgical methods, and methods of fitting prostheses embodying the invention will now be described.

Figure 18:
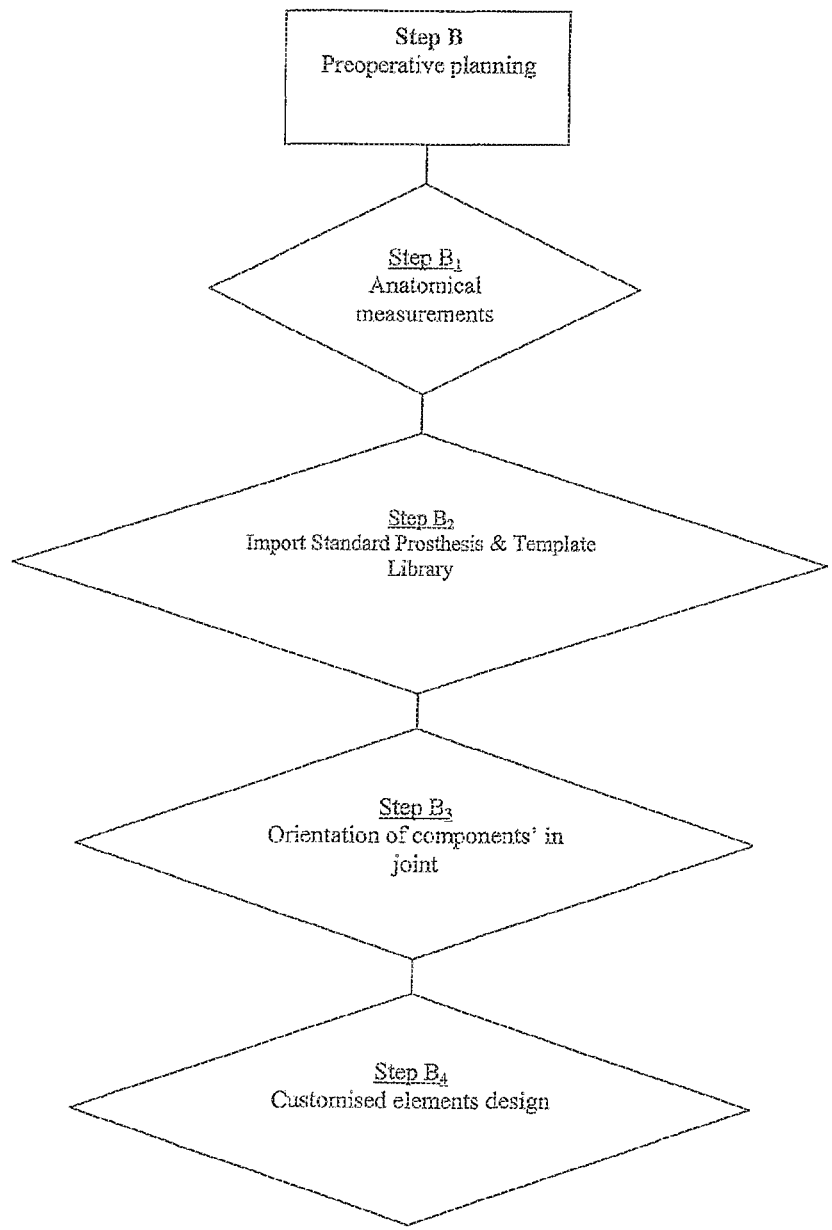
FIG. 18 is a flow chart illustrating further detail of the preoperative planning step from FIG. 17.
Figure 19:
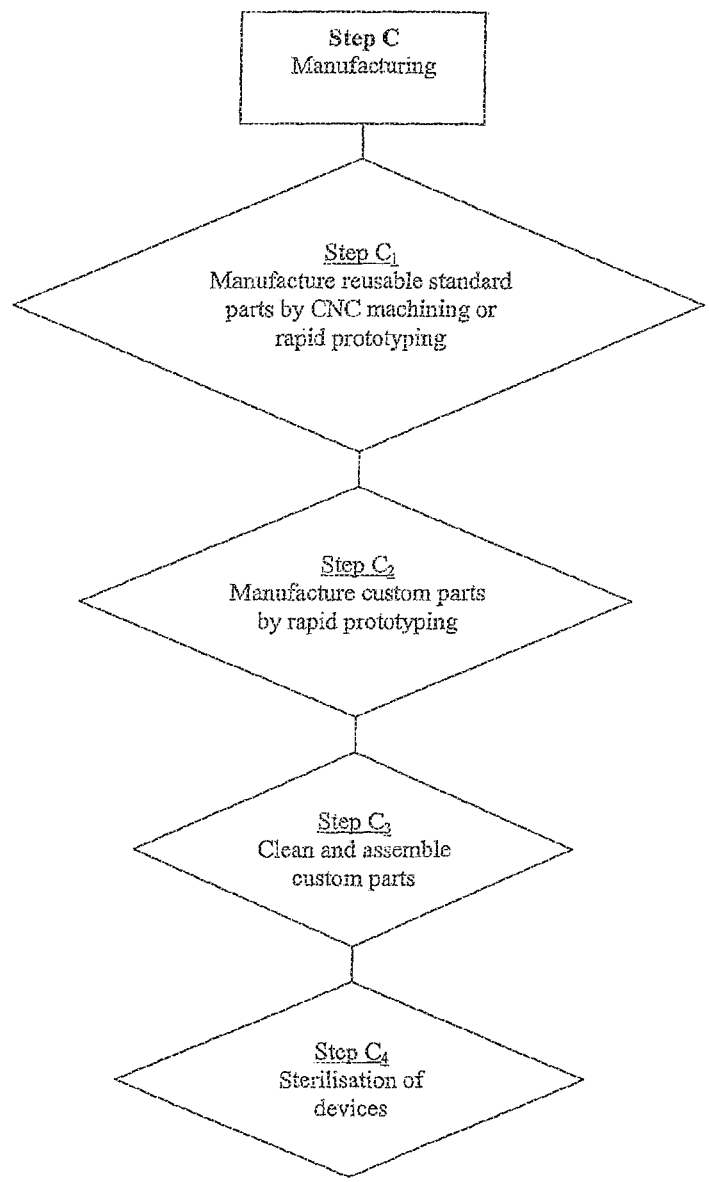
FIG. 19 is a flow-chart illustrating further detail of the manufacturing step of a method from FIG. 17.
Figure 20:
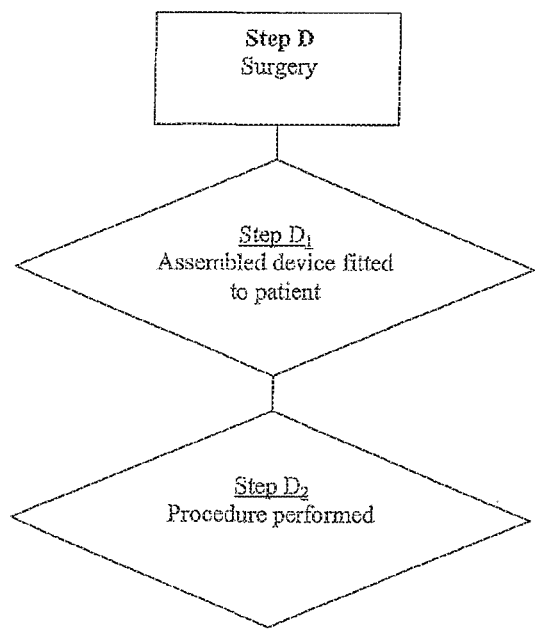
FIG. 20 is a flow chart illustrating further detail of the surgery step of the method from FIG. 17.
Figure 22A:
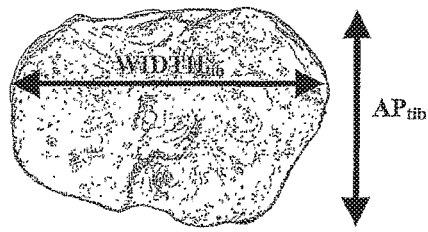
FIGS. 22a-22e are an end view of the knee joint articular surface of a tibia, a perspective view of the end of the tibia, a perspective view of a tibial prosthesis, a perspective view of the end of the tibia prepared to receive the prosthesis, and a perspective, view of the tibial prosthesis fitted to the prepared tibia respectively.
Figure 22B:
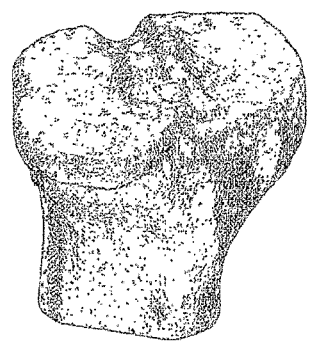
Figure 22C:
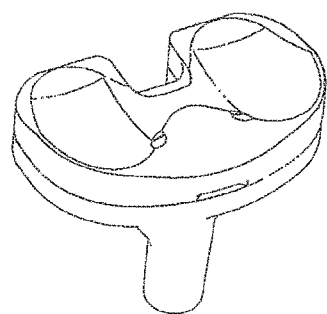
Figure 22D:
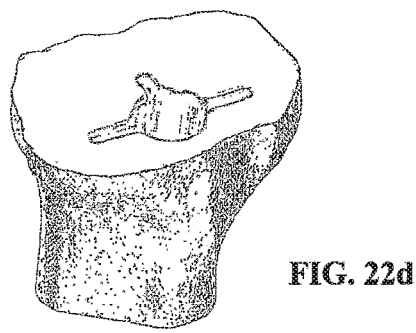
Figure 22E:
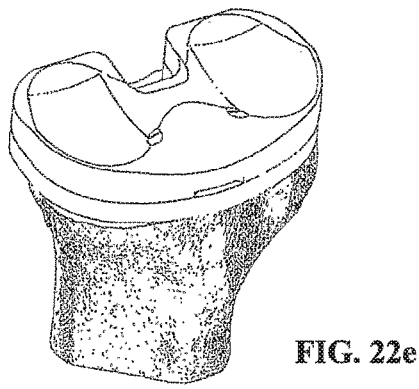

With regard to the application of this invention in the field of total knee replacement (TKR) surgery a number of steps need to be followed which are unique to the device itself. These are summarised in the flowcharts in FIG. 17. FIG. 18-20 identify the decisions and processes involved in Steps B-D which are discussed in more detail below. FIG. 21 illustrates a view of the femur from below along with isometric views of the femur, femoral prosthesis, femur with all bone cuts performed and the prosthetic component aligned to the cut femoral bone. FIG. 22 illustrates a view of the tibia from above along with similar isometric views of the tibia.

Step A—Imaging Images of the patient's joint under consideration may be acquired using CT, MRI or any other appropriate imaging modality. These are used to generate 2D/3D digital models of the joint bones from which it is possible to make accurate anatomical measurements, which will determine the size of prosthetic components for the recipient. These 2D/3D models will also allow accurate placement of virtual prosthetic components and their corresponding templates.

Step B—Preoperative Planning
Overview

Proper treatment planning is essential for the long-term success of the surgical procedure. Reconstruction of the CT data (for example) provides 3-D images, of the femur and tibia, without details of the surrounding soft tissues (Step A). Determining the correct size of the prosthetic femoral component can be achieved by measuring the antero-posterior (AP) dimension $AP_{fem}$ of the distal femur (FIG. 21). Similarly measurements of the width $WIDTH_{tib}$ and antero-posterior $AP_{tib}$ dimensions of the proximal tibia (FIG. 22) will determine the appropriate size of the prosthetic tibial component. From these measurements selection can be made of the exact (or a closely matched) size of prosthetic component for the relevant bone (FIG. 21c and FIG. 22c), from the electronic library of prosthetic components' files containing their exact geometries and dimensions. Sizing accuracy is confirmed when the selected component is superimposed (i.e. virtually implanted) over the bone and observed on the 3-D models or the 2-D projections obtained from the CT data. For instance the correct size when placed optimally will avoid violating the anterior cortex of the femur and exclude overhanging of the tibial component beyond the tibial bone. The interactive 3-D manipulation of images allows adjustment of rotation, translation, and inclination of the prosthetic components until the optimum alignment of the prosthesis within the joint is achieved. Thus in place (FIG. 21e and FIG. 22e), the final shape of the bone (FIG. 21d and FIG. 22d) after all the cuts are made is defined by the prosthesis internal surfaces (these will be in direct contact with the bone). The position of the metallic reusable cutting block referred to earlier is then aligned so that its slits and guide holes coincide with the planes defining the final shape of the bone (these are the planes defining the internal surface of the prosthesis). The design of the single use component (the standard part of which will be already attached to the reusable metallic block) is then finalised by adjusting the positions and orientations of its locators so that these are perpendicular to the surfaces of the bone where they come into contact with it. Once the locators are positioned the single use component is ready for manufacturing using rapid prototyping technologies.

Step $B_1$—Anatomical Measurements:

Anatomical measurements are taken using the images acquired in Step A. These are used to help select the most appropriately sized prosthetic components for a given patient. The decision at this stage is not critical as it is possible to try simultaneously a range of prosthetic components of different sizes on the relevant bone, as described in Step $B_2$ and finalise the decision on selecting the best size in step $B_3$.

Step $B_2$—Importing of Standard Prosthesis & Template Library:

As will be appreciated, the assembly of the guide for a given prosthetic size is the same except that the locators of the customised components are the only aspect that needs to be adjusted (customised) for the recipient. It is possible to construct a library of electronic assemblies, each pertaining to one of the different sizes of the prosthetic components. Such an electronic assembly would comprise the virtual prosthetic component aligned to the assembled guide components for that prosthetic size such that the slits and holes guiding the cutting instruments coincide with the inner surfaces of the prosthetic implant and fixation lugs.

Step $B_3$—Sizing of the Prosthetic Components and Determining their Orientation in the Joint When the electronic assembly is imported on the screen and oriented with respect to the relevant bone such that the prosthetic component is optimally placed on the bone (as described above), the standard assembly of the guide is automatically placed in the correct orientation so that the bone cuts made during surgery would be identical to that in the preoperative planning procedure. Only the locators' positions on the single use component, their lengths and orientations with respect to the bone remain to be finalised in Step $B_4$.

If the prosthetic size first determined from the anatomical measurements (Step $B_1$) is slightly larger or slightly smaller, a prosthesis of a different size together with its guide assembly could be imported and used instead. However, to save time it is proposed to import all the electronic files of these assemblies of prosthetic components and associated guide assemblies simultaneously and once the correct size has been identified all the others can be discarded.

Step $B_4$—Customised Elements Design

Whilst positioning the customisable parts it is vital to superimpose images which highlight the paths of the saw blade, drill bits and pins (used to firmly attach the guide to the bone while it is being cut) so as to avoid any obstructions by these during the preparation of the bone. Each locator therefore has a locus of points 320 relative to each template within which it must be placed. Each locus can be represented visually and therefore forms an integral part of the template library. It is anticipated that the locus of each locator can be used to fully automate Step $B_4$.

The locus of points for each locator has to be of sufficient size so as to account for the variability of the anatomy between patients. This is achieved by ensuring each custom part can accommodate the locators in a number of positions. For example with the custom part 301 the locators 306 can be united with a number of different locator arms 321. By uniting the locators 306 with single arms 322 the visibility the surgeon has of the joint whilst performing the bone cuts is kept to a maximum.

After the optimal position for each locator has been decided and fixed a number of Boolean operations are performed on the template. These are used (i) to unify the customizable components of the relevant template so that a single part is formed which can then be fixed to the relevant standard metallic component, and (ii) to ensure the custom parts match with precision the bone surface upon which they will eventually sit.

Step C—Manufacturing

Step $C_2$—Manufacture Reusable Standard Parts by CNC Machining or Rapid Prototyping Reusable standard parts are manufactured by CNC machining or rapid prototyping.

Step $C_2$—Manufacture Custom Parts by Rapid Prototyping

The custom parts for a given patient are manufactured together as separate parts held together by a rod using rapid prototyping. Although each part is free to move on the rod it cannot be removed unless the rod is broken. Each part has a unique identifier which corresponds to the patient for which they are intended.

Step $C_3$-Clean and Assemble Custom Parts

The custom parts are removed from the rod and cleaned prior to assembling them on their corresponding standard metallic parts.

Step $C_4$—Sterilisation of Devices

The assembled components are sterilized and packaged ready for shipping.

Step D—Surgery

Step $D_1$—Assembled Device Fitted to Patient

The assembled device is fitted to the patient so as to conform to the unique position relative the patient's anatomy as identified in Step B.

Step $D_2$—Procedure Performed

The template is used to guide the necessary bone cutting for the relevant prosthesis to be received.

As will be appreciated, certain embodiments of the invention provide template systems for knee surgery. The knee joint comprises two cruciate ligaments: the anterior cruciate ligament and the posterior cruciate ligament. The anterior cruciate ligament is not ordinarily preserved during total knee replacement surgery; indeed very few of the prior art total knee replacement systems allow the preservation of this ligament after surgery. However, using embodiments of the present invention it may be possible to preserve the posterior cruciate ligament during total knee replacement surgery, and in many cases this is desirable. The surgeon is able to make this decision whilst in the operating theatre and no additional instruments are required to ensure its preservation. Certain minimally invasive tibial template systems embodying the invention avoid the tibial plateau; they can be located on the appropriate bone whilst avoiding damage to the cruciate ligament. Similarly, the femoral template system can be placed on the femur without the need to cut the cruciate ligaments. Additionally, to aid accurate template placement the locators of certain template systems embodying the invention have minimal contact between the bone and themselves. The contact surfaces used in the prior art have to be large because of the local geometry of the bones upon which they sit, reducing the surface area that contacts the bone may significantly reduce their accuracy. Adapting the templates described in the prior art for unicondylar knee surgery appears not to be possible.

Unicondylar knee arthroplasty is minimally invasive and requires both cruciate ligaments to be preserved. Therefore embodiments of the present invention can be used to achieve this: the unicondylar templates would be very similar to the minimally invasive femoral and tibial templates described above, in all respects but size: they would be smaller. The adoption of CAS in unicondylar knee replacement allows placement of the femoral component such that the surface of the implant merges with that of the femoral condyle to form a smooth contour. This is very difficult to achieve with conventional instrumentation and the result is that the implant either protrudes above or locates below the surface of the condyle forming a step onto which the patella comes into contact with. This is undesirable as it might cause wear of the patella and might cause pain to the patient. Embodiments of the invention are able to solve this problem.

Figure 24:
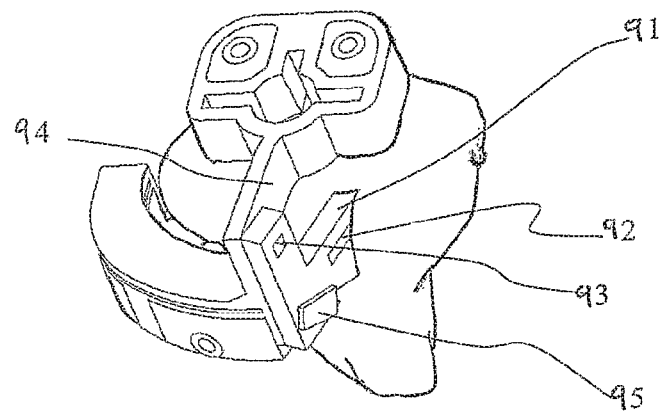
FIG. 24 is a perspective view of another template system embodying the invention and positioned on a tibia to work on that bone.

Referring now to FIGS. 24 to 27, these show tibial template systems embodying the invention and incorporating removable locators. In FIG. 24 the removable locator 91 is shown sitting is shown in the intended position. The locator helps the surgeon correctly position the device prior to fixing it upon the bone. It need not be removed as it is possible to include a slit 92 during its manufacture which allows unhindered movement of the saw blade during the preparation of the bone for the prosthesis. There is a hole 93 in the removable locator 91. This hole is aligned precisely to a hole which passes through the arm 94 of the standard tibial device. This allows a removable metal pin to be passed through 93 and into the standard metallic component. This pin along with the metal lug 95 of the standard tibial device locks the locator into position. The lug 95 is so designed that once the pin is removed the locator 91 can be removed without dislodging the fixed device.

Figure 25:
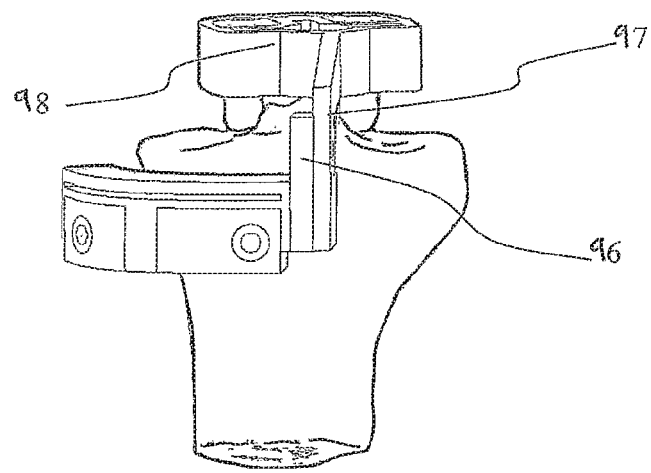
FIG. 25 is another view of the template system of FIG. 24 in position on a tibia.
Figure 26:
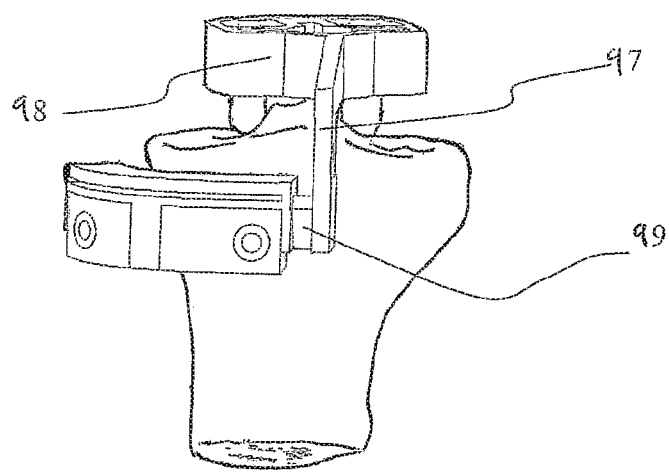
FIG. 26 is a view of another template system embodying the invention and positioned to work on a tibia.

FIG. 25 shows a tibial device similar to that shown in FIG. 1. However the removable locator 96 is inside the arm 97 of the standard part 98. This reduces the size of the device in FIG. 25 compared to that in FIG. 24. FIG. 26 shows the same standard metallic part 97 as that shown in FIG. 25 but with the removable locator 96 no longer in place. The metal lug 99 holds the removable locator in position along with a metal pin similar in nature to the pin described above.

Figure 27:
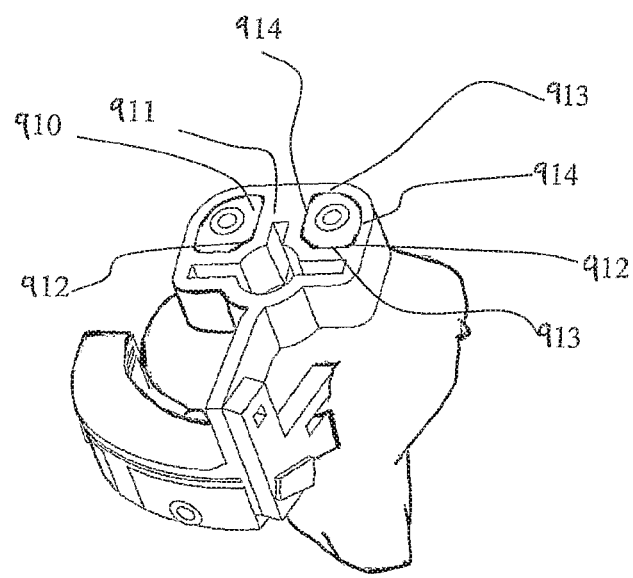
FIG. 27 is a view of another surgical template system embodying the invention and positioned to work on a bone.

FIG. 27 shows the same tibial device as FIG. 24. The custom part 910 is located into the metallic part 911 and the two parts secured with a bolt or screw. Attention has to be paid to the tolerances of each part otherwise they will not fit together. Where there is a curved region gaps 912 exist between the custom part 910 and the metallic part 911. By reducing the area of contact between 910 and 911 in the vertical direction to two orthogonal regions 913 and 914 the preciseness of fit between 910 and 911 is maintained whilst the risk of the custom part 910 being too large for the standard part 911 is reduced.

Figure 29A:
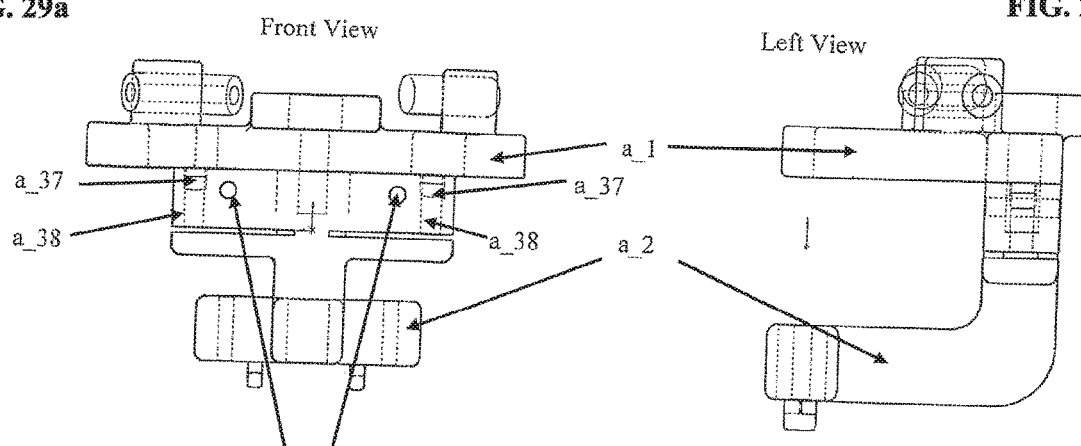
Figure 29B:
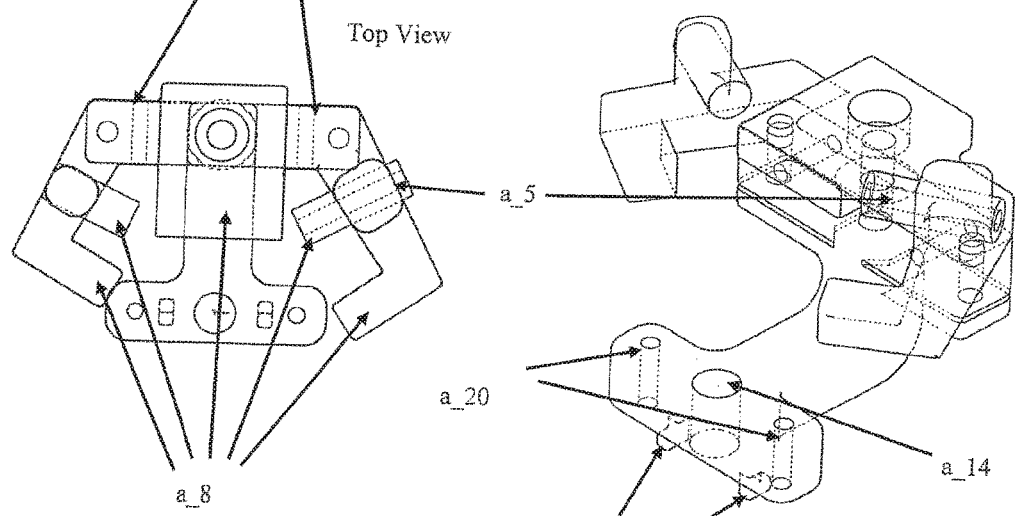

In certain embodiments the orienting block 1 (or locating means) is firmly attached to the relevant bone with pins through locators 6. These are positioned during the preoperative planning so as to be perpendicular to the bone surface they are in contact with. This ensures the pins do not skid as they are driven through the bone surface thus firmly securing the orienting block in place while the bone is being cut. However there are instances when it may be advantageous to fix both the orientating block and its standard cutting block (tool guide block 2) to the relevant bone with pins. Such an example is shown in FIGS. 28 and 29. In certain alternative embodiments, just the tool guide block may be attached to the bone. To enable the tool guide block to be attached to the bone it is provided, in certain embodiments, with one or more bores (which may also be described as pin holes or guides). Thus, in certain embodiments, the system comprises pin holes passing through a metallic cutting block.

The example shown in FIGS. 28-29 is that of a femoral template, but the majority of features that will be described in detail are also applicable in principle to the tibial template and indeed any-other template system for use on a bone. An asymmetrical custom part (in this instance) [a_1] (or locating means 1) is firmly attached to a standard, re-usable cutting block [a_2] (or tool guide block 2). The arms [a_7] of the locating means are therefore close to the appropriate bone, so reducing the intra-operative displacement of a number of tissues whilst increasing the strength of the custom part. The customised part [a_1] is guided into the correct position (for attachment to the cutting block) by pegs [a_37] (see FIG. 29) on the under surface of the locating means [a_1]. These pegs sit in holes [a_38] that originate on the upper surface of the guide block [a_2]. Once in position, the custom part [a_1] is firmly and securely attached to the standard cutting block [a_2] by means of a hexagonal fixing bolt [a_9] in this example (alternative embodiments may of course employ alternative attachments means. The pegs [a_37] may be positioned in a manner that ensures the customised parts can only be secured to the correct sized cutting block [a_2] as determined by the preoperative plan.

The standard cutting block [a_2] is located on the bone as determined by the orientating block (custom part) [a_1]. The locating fingers [a_8] (which may also be described as locators 6) of the orientating block simultaneously contact the bone of the particular patient and sit on it in a unique position, thus orientating the cutting block in the appropriate position. Once this unique position has been achieved it can be fixed securely in place with a number of pins. Two of the pins [a_3] pass through the standard block in this example (in other words, they pass through bores [a_12] in the tool guide block. These pins are parallel to one another and the slit [a_10]. The pins [a_3] are almost perpendicular to the anterior bone surface. In this instance slit [a_10] allows the distal bone cut to be made by accurately guiding the saw blade. By having the pins [a_3] parallel to one another it is possible to remove the template whilst keeping the pins [a_3] in situ (provided or course that any other pins that would otherwise prevent this removal have been removed or are not yet fitted, or the locating means has been detached from the tool guide block). Thus, the tool guide block may be separated from the bone by sliding it off the parallel fixing pins. This allows additional parts to be readily fitted to the standard part [a_2] or, the custom part [a_1] intra-operatively without the potential for interference from the patients surgically exposed tissues.

In FIG. 29 the holes [a_12] that allow the passage of pins [a_3] are shown. Although only two holes are shown it is possible to have a series of holes whose axes are all parallel to one another; the two most convenient holes may be then selected by the surgeon intra-operatively. By having the holes [a_12] in the standard metal part it is possible to drill the pins into place without the danger associated with the shedding of material into the patient's tissues. Pin [a_4] passes through the custom part [a_1]. This is guided by the bore [a_5] (through a locator [a_8]) whose orientation is adjusted pre-operatively so that its orientation is perpendicular to the surface of the patient's bone (to prevent skidding as it is driven into the bone). Pin [a_4] is approximately perpendicular to the pins [a_3], so it serves to 'lock the template' in place. The surgeon has greater access to the patient's knee bones from the medial side hence the bore [a_5] is located on the medial side of the operated joint.

Although only one pin [a_4] is shown through bore [a_5], additional, similar pins and bores that pass through the custom part [a_1] may be required to fix the template firmly in place and prevent it from loosening as the bone is cut with the oscillating blade. These pins and bores may be in positions that are anterior or lateral to the patient's knee bone. It is also feasible for the standard part [a_2] to be modified so that a pin serving the same function as [a_4] passes through the standard part in addition to, or instead of, those passing through the custom part. Any pin passing through the standard part may be driven or drilled into the bone without the danger of shedding particulate material into the patient's bone.

Achieving placement of a customised template component on its respective bone requires careful consideration of the number and positions of the locators. The following applies to the component customised for the femoral bone. The customised template component might have five locators (for example), two on the medial side, one anterior and two on the lateral as illustrated in FIG. 28. While the template component might be placed such that the five locators are simultaneously in contact with the bone there is still the possibility that the template can be incorrectly placed: because of the presence of a slippery soft tissue layer (albeit thin) on the bone surfaces, this renders the contact between the locators and bone surfaces to be soft and consequently the template may easily be pushed further in an inferior direction thus resulting in inaccuracies in cutting the bone. For this reason, in another template system embodying the invention, an additional locator is included and which is arranged to limit movement of the template in the direction mentioned above.

In certain examples, this additional locator is a removable locator [a_13], and is shown in FIG. 28 and FIG. 30. This sits inferiorly to the patient's femoral condyles and simultaneously contacts the patient's knee bone along with the locating fingers [a_8]. To ensure all of the locators contact the bone simultaneously the surgeon may have to remove some cartilage from the surface of the condyles. The removable locator is locked into the standard part [a_2] within of the bore [a_14] and constrained by the arms [a_15]. To fit the removable locator its shaft [a_130] is inserted into bore [a_14] from below, and twisted such that the arms [a_15]

capture its lugs [a_150]. It may be necessary to include a series of bores similar to [a_14] or a slit within the standard part so that the most suitable position for the removable locator can be determined during the pre-operative planning stage. The inclusion of appropriate lettering [a_16] (A for anterior, a P for posterior in this instance) or symbols ensures the removable locator is correctly orientated with the standard part.

Figure 31:
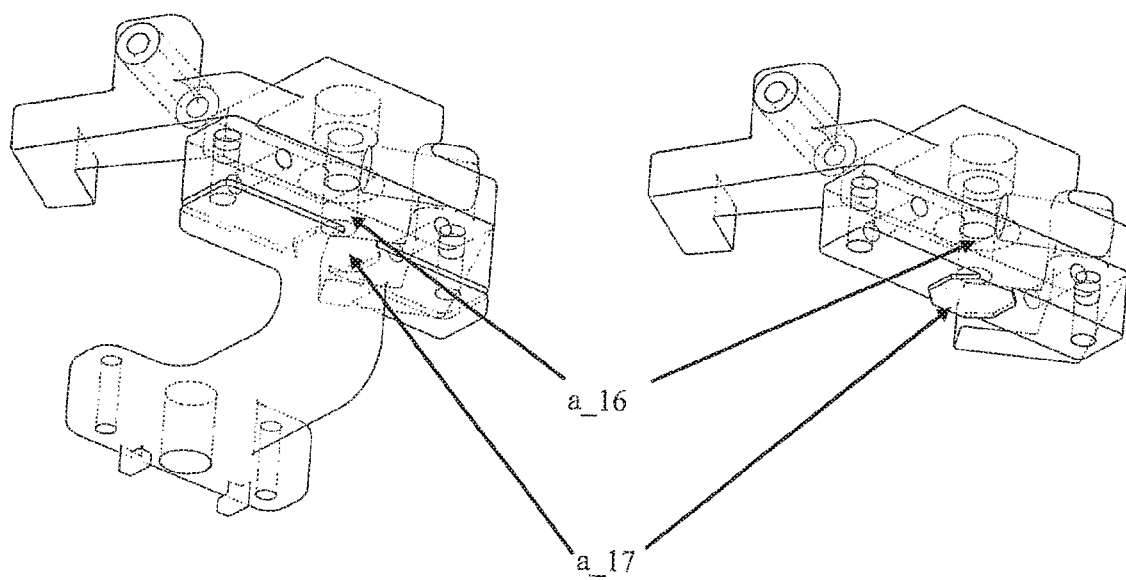
FIG. 31 illustrates another template system embodying the invention.

The slit [a_10] extends laterally and medially (see FIG. 28) but is closed centrally so that the sawblade can make the intended bone cut though it (see FIG. 31). The central solid section within the said slit allows the thread of the hexagonal fixing bolt [a_9] to pass through the body of the standard part. The central portion [a_17] is angled to permit a greater range of movement for the saw blade.

Figure 32:
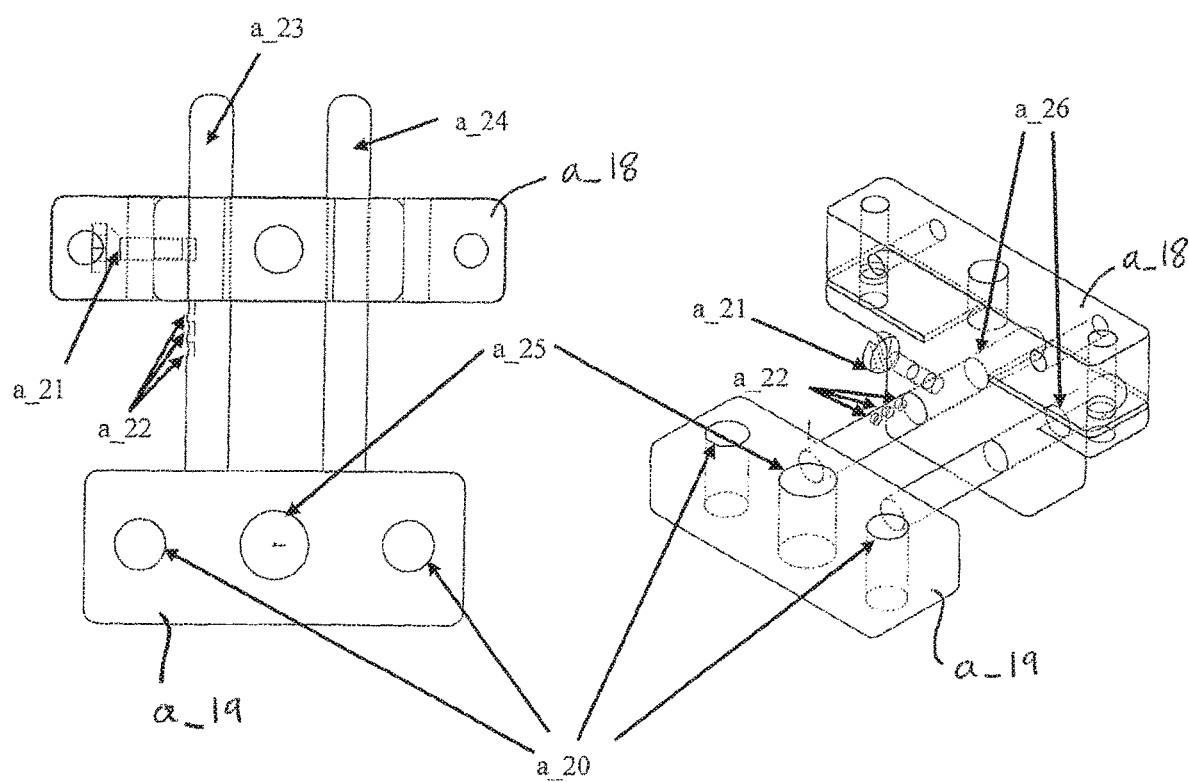
FIG. 32 illustrates another template system embodying the invention.
Figure 33A:
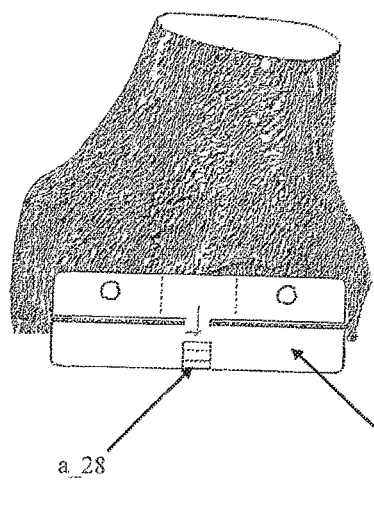
FIGS. 33a-33d illustrate components of another template system embodying the invention and positioned with respect to a femur.
Figure 33B:
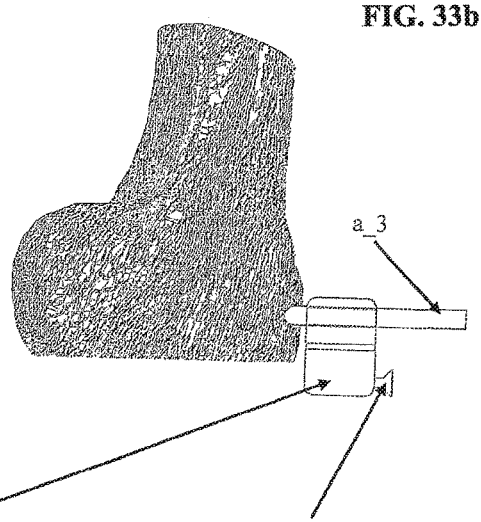
Figure 33C:
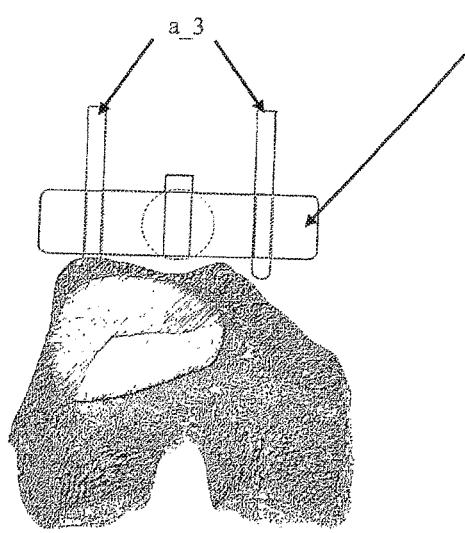
Figure 33D:
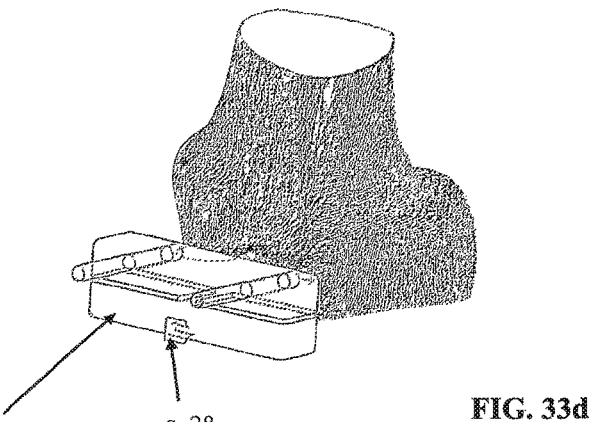

Implants of the same type are available in a number of different sizes. The most appropriate implant size for the patient is determined from appropriate measurements taken from the patient's bones preoperatively. Different implant sizes may require standard cutting blocks such as [a_2] shown in FIG. 28 to be of different sizes. Thus implants of the same type may require an inventory of a plurality of cuttings blocks (e.g. six), each a different size but all similar to [a_2]. The correct size of cutting block for a given patient is determined during the preoperative plan. However, by allowing the relative positions of the distal cut block and the lug block to be changed it may be possible to reduce the number of standard blocks [a_2] required (typically from 6 to 2) for a given implant type:

FIG. 32 shows a standard cutting block comprising of two main parts (in this instance) [a_18] and [a_19]. The position of [a_18] relative to [a_19] may be adjusted and fixed rigidly with a screw or screws (for example) such as that shown [a_21] according to the size of implant required. The screw locates in depressions [a_22] on the arm [a_23]. A custom part similar to [a_1] (shown in FIG. 28 and FIG. 29) is securely fastened to the distal cut block [a_18] and serves to orientate both the distal cut block and the lug block [a_19] simultaneously according to the preoperative plan. The lug block [a_19] has two holes [a_20] passing through it. The purpose of the holes [a_20] in both FIG. 29 and FIG. 32 is to guide a drill in preparing holes that will allow a cutting block similar to the one shown in FIG. 8 to be positioned on the bone as indicated in FIG. 9. These holes align exactly with the lugs [311] as shown in FIG. 8. They may also coincide with lugs on the femoral implant.

It is also possible for the lug block to hold a removable locator similar to [a_13] (see FIG. 28) within a bore [a_25] (see FIG. 32) which is similar to [a_14] (FIG. 29). Although not shown in FIG. 32, this removable locator may be locked into place with similar means to that described previously. Also, if the removable locator is deemed unnecessary it is possible for the distal cut block to hold a lug block similar to [a_19] that sits exactly on the femur after the distal cut has been made in a position that has been determined during the preoperative plan. Additional holes in the body of the distal cut block similar to [a_26] may be necessary to hold the arms similar to [a_23] and [a_24] in the correct position before locking them by a screw(s) similar to [a_21].

On occasions it may be necessary to revise the distal cut (for example) of the femur for patients with a flexion contracture of the knee (for example). In such cases a revised distal cut parallel but superior to the first is performed. In all other respects the preparation of the patients bone is likely to remain as planned preoperatively. FIG. 33 shows a distal cutting block [a_27] that has been guided into place by the pins [a_3] (see FIG. 28 also). Although both pins are not shown contacting the bone, the intention is for them to be located sufficiently deep in the bone tissue to provide (in conjunction with pin [a_4]) a means of securely fixing a template such as the one shown in FIG. 28 onto the bone. As indicated previously, the pins [a_3] are parallel to one another and the distal cut. This makes it possible to position an additional distal cutting block [a_27] in a precise position relative to the patient's bone without removing the pins [a_3]. In other words, a first cutting block may be attached to the bone using parallel pins [a_3], and a cut may be made using the first block as a tool guide. Then, if it is decided to perform a cut at a revised position, the first block may be removed by sliding it off the parallel pins, and a second block may be slid onto the pins, that second block providing the guide means necessary to perform the cut at the revised position. In doing so the surgeon is able to address the problem of patients with a flexion contracture intraoperatively. A feature such as that indicated by [a_28] may be used to lock a handle onto the distal cutting block [a_27] which the surgeon or assistant may use to steady the cutting block as the distal cut is revised.

With rapid prototyping techniques, objects are typically built in a series of layers between 0.01 and 1.0 mm thick. This allows for the precise construction of complex geometries. If there is sufficient space within a build chamber a number of different objects can be built up simultaneously by rapid prototyping. In certain embodiments of the invention the custom parts of the patient specific templates are manufactured with a rapid prototyping machine. With rapid prototyping (for example) it is possible that the manufactured custom parts may be distorted and dimensionally inaccurate in any or all of the x, y, z directions: these inaccuracies resulting from the manufacturing process alone. The inaccuracies may not be uniform, they may occur in a particular direction (x, y, z) in space and even within a confined region of the build. FIGS. 34 and 35 illustrate locating means manufactured to include features enabling checks to be made easily on the accuracy of the manufacturing process. By including a number of features such as those shown in FIG. 34 and FIG. 35 within the template designs (for example) it is possible to quickly assess the dimensional accuracy of the custom parts for a given patient.

Figure 34A:
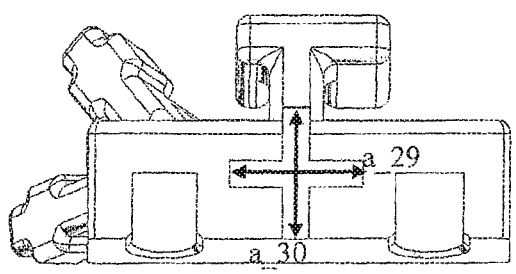
FIGS. 34a-34c illustrate the locating means of a template system embodying the invention, the locating means comprising an indicator measurable with a gauge or other means to provide a check on the manufacturing accuracy of the locating means.
Figure 34B:
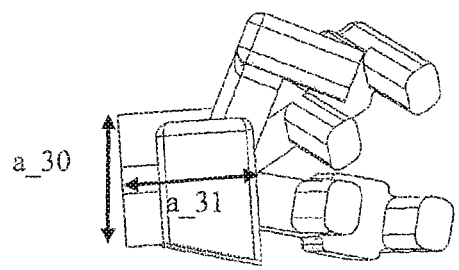
Figure 34C:
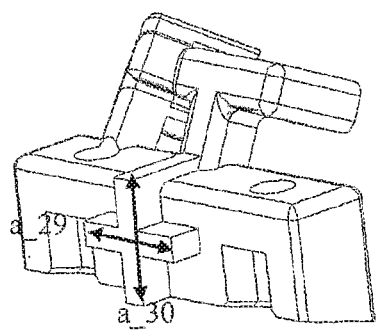

In FIG. 34 identical and prominent features are incorporated into the custom, locating part of the template. The locating means shown in FIGS. 34a-34c includes a generally cruciform indicator having distinct and easily measurable dimensions. The three dimensions [a_29], [a_30] and [a_31] of the indicator structure are mutually orthogonal and should be of identical length if the manufacture has taken place properly. This facilitates checking of the indicator dimensions with a go/no-go gauge. Such a gauge is adapted to engage the indicator to provide the dimensional check. It is also possible to include on certain locating means features such as those shown in FIG. 35. These features comprise pairs of indicia having separations measurable with suitable gauges or other means. In the example shown in FIGS. 35a-35c, the dimensions [a_32], [a_33] and [a_34] (each corresponding to a separation between a respective pair of indicia) are orthogonal to one another, enabling the accuracy of manufacturing to be determined in all three dimensions.

Figure 36:
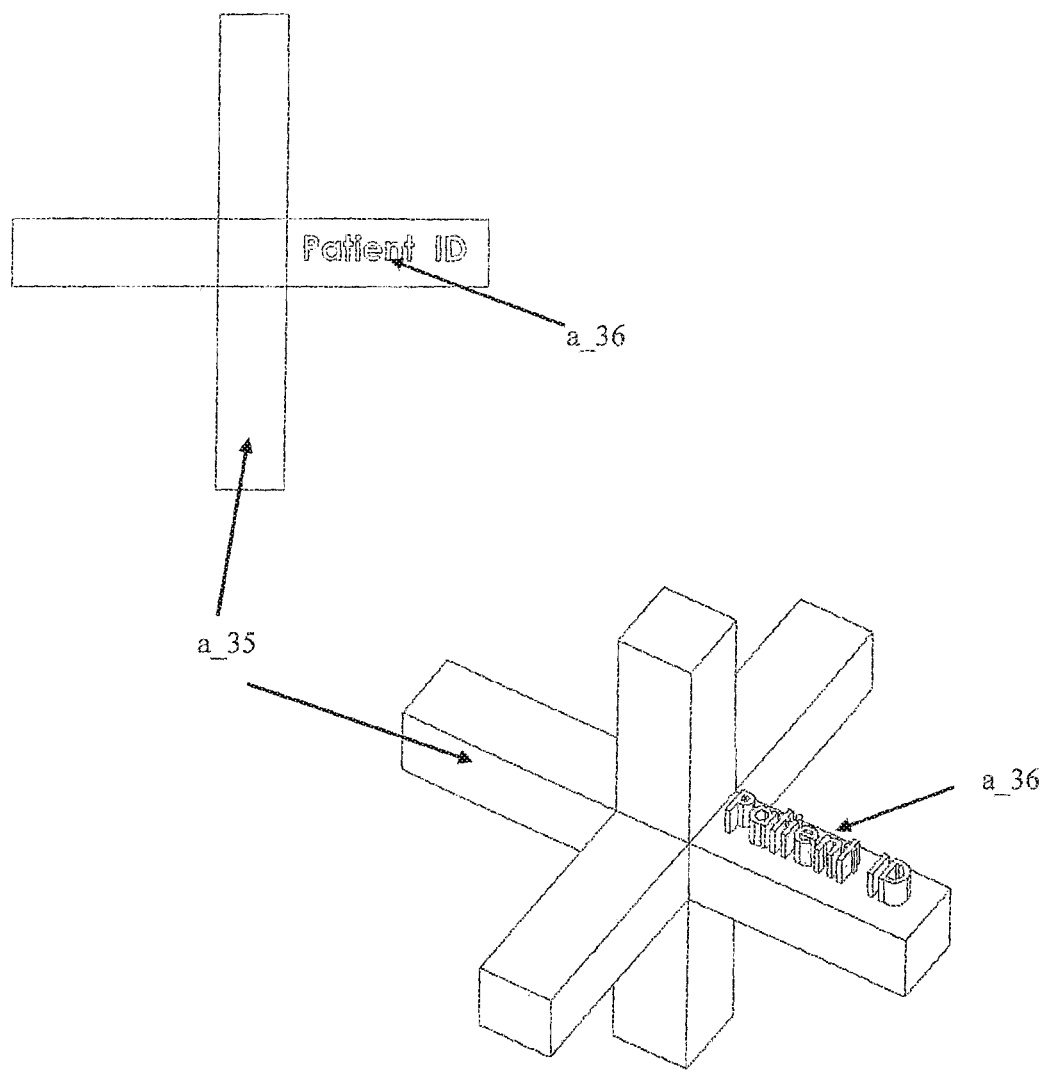
FIG. 36 illustrates an indicator manufactured together and integrally with the locating means of certain embodiments and measurable with a gauge or other measurement means to provide a check in three dimensions on the manufacturing accuracy of the locating means before use in surgery.

When manufacturing the locating means it is also possible to include an indicator or indicator structure, separate but attached to the locating means, and having features such as those shown in FIG. 36. The part or indicator [a_35] consists of fingers of nominally identical length which are orthogonal to one another. The lengths of these fingers can easily be checked before the locating means is used in a surgical procedure. If the fingers are all the same, correct length, then the co-manufactured locating means will also be dimensionally correct in three dimensions. This allows a means of checking the dimensional accuracy of the custom parts similar to that already described. In certain embodiments indicator [a_35] may be joined to the custom locating parts by a thin rod (formed during the rapid prototyping process). This would also allow the dimensional accuracy of the manufactured parts to be checked. Once checked the component can be detached by breaking the rod. It may also be appropriate to include a unique identifier [a_36] on such parts which relates it uniquely to the given custom parts. With such an identifier it may not be necessary to physically link the custom parts with parts such as [a_35]. However it may be appropriate for a known spatial relationship to exists between the custom parts and the parts that allow their dimensional accuracy to be checked.

With regard to surgical methods and prosthesis fitting methods embodying the invention, it will be appreciated that because the locators in certain embodiments are designed on the basis of CT scans, to sit on bone, during the operation if there is any cartilage residue at the site of these locators then that cartilage residue should be removed before locating and securing the template system, otherwise the accuracy of the cut(s) and/or hole(s) using the template would be affected.

From the above description it will be appreciated that certain embodiments of the present invention relate to methods, systems and devices for facilitating total knee replacement surgery, particularly in respect of making the bone cuts in the knee bones so these are made to allow the prosthetic components to be implanted accurately and in the correct orientation within the joint of the recipient. Certain embodiments of the present invention comprise template systems that are customised for total knee replacement surgery via large incisions as well as those for minimally invasive surgery in which it is aimed to prepare the bone cuts and implant the prosthetic components through the smallest possible incisions in the joint. This reduces the trauma to the surrounding tissues, and speeds up the recovery of the patient.

We claim:

1. A system comprising:
a metal saw guide that has a slot to receive and guide a saw;
a plastic body; and
a plurality of plastic locating members that extend from the plastic body,
wherein at least one plastic locating member of the plurality of plastic locating members is patient-specific,
wherein each plastic locating member has a respective bone-engaging surface that conforms to a corresponding surface of a femur,
wherein each plastic locating member has a bore extending through the plastic locating member,
wherein the metal saw guide is non-adjustably attached to the plastic body, and
wherein each plastic locating member conforms against the corresponding surface of the femur to place the metal saw guide in a fixed position relative to the femur.

2. The system of claim 1, further comprising a plurality of metal sleeves, each sleeve lining a respective bore of each plastic locating member.

3. The system of claim 2, further comprising a plurality of pins to extend through the plurality of metal sleeves and into the femur.

4. The system of claim 1, wherein at least two plastic locating members of the plurality of plastic locating members are spaced apart from each other.

5. The system of claim 1, wherein at least one of the plastic locating members of the plurality of plastic locating members is adapted to engage an articular surface of the femur.

6. The system of claim 1, wherein at least one of the plastic locating members of the plurality of plastic locating members is adapted to engage a non-articular surface of the femur.

7. The system of claim 1, wherein the metal saw guide accepts a saw blade.

8. The system of claim 1, wherein the plastic body has an additional bore extending through the plastic body.

9. The system of claim 8, further comprising a metal sleeve lining the additional bore of the plastic body.

10. The system of claim 9, wherein the metal sleeve is a drill guide.

11. A system comprising:
a metal saw guide that has a slot to receive and guide a saw;
a plastic body; and
a plurality of plastic locating members that extend from the plastic body,
wherein at least one plastic locating member of the plurality of plastic locating members is patient-specific,
wherein each plastic locating member has a respective bone-engaging surface that conforms to a corresponding surface of a femur,
wherein the metal saw guide is non-adjustably attached to the plastic body, and
wherein each plastic locating member conforms against the corresponding surface of the femur to place the metal saw guide in a fixed position relative to the femur.

12. The system of claim 11, wherein each plastic locating member has a bore extending through the plastic locating member.

13. The system of claim 12, further comprising a plurality of metal sleeves, each sleeve lining a respective bore of each plastic locating member.

14. The system of claim 13, wherein at least two plastic locating members of the plurality of plastic locating members are spaced apart from each other.

15. The system of claim 14, wherein at least one of the plastic locating members of the plurality of plastic locating members is adapted to engage an articular surface of the femur.

16. The system of claim 14, wherein at least one of the plastic locating members of the plurality of plastic locating members is adapted to engage a non-articular surface of the femur.

17. The system of claim 14, wherein the metal saw guide accepts a saw blade.

18. The system of claim 14, wherein the plastic body has an additional bore extending through the plastic body.

19. The system of claim 18, further comprising a metal sleeve lining the additional bore of the plastic body.

20. The system of claim 19, wherein the metal sleeve is a drill guide.

21. The system of claim 12, further comprising a plurality of pins to extend through the plurality of metal sleeves and into the femur.

22. An orthopedic surgical template system for preparing a femur to receive a femoral component of prosthetic knee, the system comprising:

a metal saw guide comprising at least one slot to receive and guide a saw blade for cutting the femur;

a patient-specific orienting component comprising a polymeric body portion and a plurality of polymeric locating members that extend from and are integral with the body portion, each locating member having a respective bone-engaging surface that conforms to a corresponding portion of a predetermined surface of the femur, each locating member having a bore extending through the member;

a plurality of metal sleeves, each sleeve being disposed in a respective bore of a locating member; and a plurality of pins adapted to extend through the metal sleeves and into the femur to assist in securing the patient-specific orienting component relative to the femur;

wherein the saw guide is non-adjustably attached to the patient-specific orienting component such that the saw guide is secured in a fixed position with respect to the locating members and such that when the locating members are placed against different respective portions of the predetermined surface of the femur and secured in place by pins that are extended into the femur, the slot of the saw guide is located at a predetermined position for receiving and guiding the saw for cutting off a distal portion of the femur.

23. The system of claim 22, wherein the patient-specific orienting component further comprises a protrusion integral with and extending from the body portion, wherein the protrusion is adapted to engage a corresponding portion of the predetermined surface of the femur, wherein the protrusion does not have a bore.

24. The system of claim 22, wherein the locating members extend from the body portion a greater distance than the protrusion.

25. The system of claim 22, wherein the bone engaging surfaces are spaced apart from each other such that when the patient-specific orienting component is secured to the femur, portions of the predetermined surface of the femur between the bone engaging surfaces are not engaged by any portion of the patient-specific orienting component.

26. The system of claim 22, wherein the predetermined surface of the femur is an articular surface of the femur and the bone engaging surfaces are adapted to engage corresponding different portions of the articular surface of the femur.

27. The system of claim 22, wherein the body portion is adapted to face a non-articular surface of the femur when the patient-specific orienting component is secured to the femur.

28. An orthopedic surgical template system for preparing a femur to receive a femoral component of a prosthetic knee, the system comprising:

a metal saw guide comprising at least one slot to receive and guide a saw blade for cutting the femur;

a polymeric patient-specific orienting component comprising a plurality of polymeric locating members, each locating member having a respective bone-engaging surface that conforms to a corresponding portion of a predetermined surface of the femur;

a plurality of metal sleeves, each sleeve being disposed in a respective bore of the patient-specific orienting component; and a plurality of pins adapted to extend through the metal sleeves and into a non-articular surface of the femur to assist in securing the patient-specific orienting component relative to the femur;

wherein the saw guide is non-adjustably attached to the patient-specific orienting component such that the saw guide is secured in a fixed position with respect to the locating members and such that when the locating members are placed against different respective portions of the predetermined surface of the femur and secured in placed by extending the pins into the non-articular surface of the femur, the slot of the saw guide is located at a predetermined position for receiving and guiding the saw for cutting off a distal portion of the femur.

29. The system of claim 28, wherein the bores are formed in the locating members.

30. The system of claim 28, wherein the patient-specific orienting component further comprises a protrusion integral with and extending from the body portion, wherein the protrusion is adapted to engage a corresponding portion of the predetermined surface of the femur, wherein the protrusion does not have a bore.

31. The system of claim 28, wherein the locating members extend from the body portion a greater distance than the protrusion.

32. The system of claim 28, wherein the bone engaging surfaces are spaced apart from each other such that when the patient-specific orienting component is secured to the femur, portions of the predetermined surface of the femur between the bone engaging surfaces are not engaged by any portion of the patient-specific orienting component.

33. An orthopedic surgical template system for preparing a femur to receive a femoral component of a prosthetic knee, the system comprising:

a metal saw guide comprising at least one slot to receive and guide a saw blade for cutting the femur;

first and second metal drill guides to receive and guide a drill bit for drilling holes in the femur; and a polymeric, patient-specific orienting component comprising a plurality of locating members, each locating member having a respective bone-engaging surface that conforms to a corresponding portion of a predetermined surface of the femur;

wherein the saw guide and the first and second drill guides are non-adjustably attached to the patient-specific orienting component such that the saw guide and the first and second drill guides are secured in fixed positions with respect to the locating members and such that when the locating members are placed against different respective portions of the predetermined surface of the femur, the slot of the saw guide is located at a predetermined position for receiving and guiding the saw for cutting off a distal portion of the femur to form a flat surface on the end of femur and the first and second drill guides are located at predetermined positions for drilling first and second holes in an articular surface of the femur.

34. The system of claim 33, wherein the patient-specific orienting component comprises a plurality of bores and the assembly further comprises a plurality of pins adapted to be inserted through the bores and into the femur.

35. The system of claim 34, wherein the bores are located on the patient-specific orienting component at positions to direct the pins into a non-articular surface of the femur.

36. The system of claim 35, further comprising a plurality of metal sleeves, each sleeve being disposed in a respective bore.

37. The system of claim 33, wherein the saw guide comprises a first saw guide and the system further comprises a second metal saw guide comprising at least one slot and first and second locating protrusions, wherein second saw guide is adapted to be placed against the flat surface on the femur with the first and second locating protrusions inserted into the first and second holes when the patient-specific orienting component and the first saw guide are removed from the femur.

* * * * *